(12) United States Patent
Serhan et al.

(10) Patent No.: US 11,135,228 B2
(45) Date of Patent: Oct. 5, 2021

(54) CYSTEINYL-PRORESOLVING MEDIATORS THAT PROMOTE RESOLUTION OF INFECTION AND ORGAN PROTECTION

(71) Applicant: THE BRIGHAM AND WOMEN'S HOSPITAL, Boston, MA (US)

(72) Inventors: Charles N. Serhan, Needham, MA (US); Jesmond P. Dalli, Brookline, MA (US); Nan Chiang, Somerville, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/517,016

(22) PCT Filed: Oct. 7, 2015

(86) PCT No.: PCT/US2015/054536
§ 371 (c)(1),
(2) Date: Apr. 5, 2017

(87) PCT Pub. No.: WO2016/057700
PCT Pub. Date: Apr. 14, 2016

(65) Prior Publication Data
US 2017/0258806 A1    Sep. 14, 2017

Related U.S. Application Data

(60) Provisional application No. 62/061,393, filed on Oct. 8, 2014, provisional application No. 62/093,619, filed on Dec. 18, 2014.

(51) Int. Cl.
*A61K 31/557*  (2006.01)
*A61K 47/54*   (2017.01)
*A61K 47/64*   (2017.01)

(52) U.S. Cl.
CPC .......... *A61K 31/557* (2013.01); *A61K 47/542* (2017.08); *A61K 47/64* (2017.08)

(58) Field of Classification Search
CPC .................................................. A61K 31/557
USPC .......................................................... 514/72
See application file for complete search history.

(56) References Cited

U.S. PATENT DOCUMENTS

| | | | | |
|---|---|---|---|---|
| 7,544,714 B2 * | 6/2009 | Burstein | ............. | A61K 31/202 514/423 |
| 2006/0128804 A1* | 6/2006 | Serhan | ................. | A61K 31/202 514/560 |
| 2010/0104546 A1* | 4/2010 | Ferrante | ............... | A61K 31/201 424/93.71 |
| 2011/0190389 A1* | 8/2011 | Arterburn | ............. | A61K 8/361 514/475 |

FOREIGN PATENT DOCUMENTS

| WO | 2006010153 A1 | 1/2006 |
|---|---|---|
| WO | 2009006668 A1 | 1/2009 |
| WO | 2013167988 A1 | 11/2013 |

OTHER PUBLICATIONS

Tetrahedron Letters (2017), vol. 58, pp. 1662-1668 (Year: 2017).*
Rodriguez, Ana R., "Total synthesis of pro-resolving and tissue-regenerative Protectin sulfido-conjugates", Tetrahedron Letters, vol. 56, No. 42, Oct. 1, 2015, pp. 5811-5815.
Rodriguez, Ana R., "First total synthesis of pro-resolving and tissue-regenerative Maresin sulfido-conjugates", Tetrahedron Letters, vol. 56, No. 25, pp. 3936-3940.
Dalli, J., "Novel proresolving and tissue-regenerative resolvin and protectin sulfido-conjugated pathways", The Faseb Journal, vol. 29, No. 5, May 1, 2015, pp. 2120-2136.
PCT International Search Report and Written Opinion, PCT/US2015/054536, European Patent Office, dated Dec. 14, 2015.

* cited by examiner

*Primary Examiner* — Taina D Matos Negron
(74) *Attorney, Agent, or Firm* — Christensen, Fonder, Dardi & Herbert PLLC; Colin L. Fairman

(57) ABSTRACT

A family of bioactive compounds identified in self-resolving inflammatory exudates is disclosed. The compounds give UV chromophores characteristics of a conjugated triene double bond system coupled to an auxochrome allylic to the triene. Further elucidation of the compounds reveals that they have an oxylipin backbone conjugated to a peptide or amino acid moiety via an auxochrome. In some embodiments the auxochrome is sulfur. However, the auxochrome may be NH, CH2 or O. The compounds have potent bioactivity, in vitro, and, in vivo, including promoting resolution of infection, stimulating macrophage phagocytosis of bacteria; protecting tissues from neutrophil mediated damage, promoting tissue repair and regeneration and preventing or limiting second organ reflow/reperfusion damage.

4 Claims, 34 Drawing Sheets

Specification includes a Sequence Listing.

| SCII ions (m/z, Da) | d5-SCII ions (m/z, Da) | Dimethyl derivative ions (m/z, Da) |
|---|---|---|
| 521 | 526 | 549 |
| 504 | 509 | 532 |
| 503 | | |
| 477 | 482 | 505 |
| 459 | 464 | 487 |
| 343 | 348 | 357 |
| 329 | 334 | 343 |
| 325 | 330 | 339 |
| 281 | 286 | |
| 235 | 235 | 249 |
| 217 | 217 | 231 |
| 205 | 205 | 219 |
| 199 | 199 | 213 |
| 191 | 191 | 205 |
| 187 | 187 | |
| 179 | 179 | 193 |
| 173 | 173 | |
| 162 | 162 | 176 |
| 147 | 147 | 161 |
| 145 | 145 | 159 |
| 131 | 131 | 145 |
| 115 | 115 | 129 |
| 109 | 114 | 109 |

C

| SCII ions (m/z, Da) | d5-SCII ions (m/z, Da) | Dimethyl derivative ions (m/z, Da) |
|---|---|---|
| 521 | 526 | 549 |
| 504 | 509 | 532 |
| 503 | | |
| 477 | 482 | 505 |
| 459 | 464 | 487 |
| 343 | 348 | 357 |
| 329 | 334 | 343 |
| 325 | 330 | 339 |
| 281 | 286 | |
| 235 | 235 | 249 |
| 217 | 217 | 231 |
| 205 | 205 | 219 |
| 199 | 199 | 213 |
| 191 | 191 | 205 |
| 187 | 187 | 193 |
| 179 | 179 | 193 |
| 173 | 173 | 173 |
| 162 | 162 | 176 |
| 147 | 147 | 161 |
| 145 | 145 | 159 |
| 131 | 131 | 145 |
| 115 | 115 | 129 |
| 109 | 114 | 109 |

$R_1 = NH, CH_2, O$ $R_1 = NH, CH_2, O$

CYSTEINYL-PRORESOLVING MEDIATORS THAT PROMOTE RESOLUTION OF INFECTION AND ORGAN PROTECTION

CROSS-REFERENCE TO RELATED APPLICATIONS

This application represents the national stage entry of PCT International Application No. PCT/US2015/054536 filed Oct. 7, 2015, which claims priority of U.S. Provisional Patent Application No. 62/061,393 filed Oct. 8, 2014, and U.S. Provisional Patent Application No. 62/093,619 filed Dec. 18, 2014, the disclosures of which are incorporated by reference here in their entirety for all purposes.

STATEMENT REGARDING FEDERALLY SPONSORED RESEARCH

The work leading to this invention was supported, in part, by National Institutes of Health (NI H) grant P01GM095467. The United States Government may have certain rights in this invention.

FIELD OF THE DISCLOSURE

This invention relates generally to novel bioactive oxylipin derivatives conjugated to an amino acid or peptide by an auxochrome moiety. The compounds have beneficial effects in organ protection, tissue regeneration, and resolving inflammation.

BACKGROUND OF THE DISCLOSURE

Given the rise in antibiotic-resistant infections and the critical role that barrier breach plays in microbial invasion, identification of new endogenous signals that promote pathogen clearance and tissue repair/regeneration are of wide interest (1). When self-limited, acute inflammation is a host-protective response (2, 3) that is orchestrated by chemical mediators and is an active process generated by evolutionarily conserved biosynthetic pathways (3, 4). During initiation of inflammation, potent mediators are locally produced that promote vascular leakage, leukocyte recruitment and pain (5, 6). In disease, these pathways can be dysregulated leading to heightened inflammatory responses and perpetuation of the disease state (6-9). One approach to regulate exuberant inflammatory responses is inhibition of initiating mediators (e.g. eicosanoids including prostaglandins) via biosynthetic enzyme inhibitors (6, 10) and receptor antagonists (5). In the context of infection, this approach may be of limited clinical utility and can have potential drawbacks including immune suppression (7, 8).

Acute inflammation is a protective response mounted by the host following injury and/or infection (1-3). When this response becomes deregulated, it leads to unabated leukocyte activation and chronic inflammation. The acute response is coordinated by autacoids that include the arachidonic acid-derived prostaglandins (PGs), some of which (i.e., $PGE_2$ and $PGD_2$) regulate edema formation and leukotriene (LT) $B_4$ that mediate leukocyte recruitment to the site (1, 4, 5). Excessive production of these bioactive mediators is thought to be the cause of many chronic inflammatory conditions. Thus, an extensive effort was undertaken in recent decades to inhibit production of proinflammatory mediators (3-6) in conditions where their excessive production was associated with the underlying pathology. Although in the short term this approach yielded some clinical benefit in select conditions, in the long term, it was found to lead to immune suppression (1).

It is now appreciated that resolution of inflammation is an active cellular and biochemical process orchestrated by local acting mediators that include gaseous molecules such as hydrogen sulfide (7) and essential fatty acid (EFA)-derived signals, the latter constituting a new genus of specialized proresolving mediators [SPMs; recently reviewed in (8)]. This novel genus of mediators includes the arachidonic acid-derived lipoxins, the eicosapentaenoic acid-derived E-series resolvins, and the docosahexaenoic acid (DHA)-derived D-series resolvins (RvD), protectins (PD), and maresins (8⇓-10). These counterregulate proinflammatory mediator production, including PGs, LTs, and select cytokines (8, 10). They also stimulate leukocyte responses including bacterial phagocytosis and efferocytosis of apoptotic cells, key processes in the clearance of infections and return to homeostasis, without apparent immune suppression (1, 8). In addition to these actions that are shared by all proresolving mediators, each SPM displays characteristic roles. For example, resolvin D1 (7S,8R,17S-trihydroxy-docosa-4Z, 9E,11E,13Z,15E,19Z-hexaenoic acid; RvD1), resolvin D2 (7S,16R,17S-trihydroxy-docosa-4Z,8E,10Z,12E,14E,19Z-hexaenoic acid; RvD2), and resolvin D5 (7S,17S-dihydroxy-docosa-4Z,8E,10Z,13Z,15E,19Z-hexaenoic acid; RvD5) enhance clearance of bacterial infections (8, 11), and resolvin E1 (5S,12R,18R-trihydroxy-eicosa-6Z, 8E,10E, 14Z,16E-pentaenoic acid; RvE1) promotes clearance of viral infections (12) and neutrophil apoptosis (13). In addition, maresin 1 (7R,14S-dihydroxy-docosa-4Z,8E,10E,12Z, 16Z,19Z-hexaenoic acid; MaR1) and RvE1 promote tissue regeneration (8, 14).

In self-limited inflammation, endogenous programs are activated at the onset that regulate the amplitude of the inflammatory responses and stimulate resolution (3, 9). Central to these host protective responses are novel families of endogenous chemical mediators termed specialized proresolving mediators (SPM) (9).

In many cases, SPM include oxylipins, a group of bioactive, oxidized metabolites of fatty acids. Biosynthesis of oxylipins is initiated by dioxygenases, monooxygenases, lipoxegenases, cycloxygenases and cytochrome P450. The most well-known of the oxylipins are the prostaglandins and leukotrienes, which play roles in contraction and regulation of smooth muscle and are inflammatory promoters which act to recruit neutrophils to areas of tissue damage, promote bronchoconstriction and activate leukocytes. Together, these oxylipins act to stimulate and enhance the inflammatory response.

However, SPM include specialized classes of oxylipins which promote the resolution phase of inflammation. These classes of compounds include those commonly known as resolvins, protectins and maresins.

In sterile inflammation and injury, SPM actively limit further neutrophil recruitment and promote macrophage clearance of apoptotic cells and tissue debris (7-9). In self-resolving infections, endogenous resolution programs are also activated during the early stages of inflammatory responses, with the upregulation of select SPM (including Resolvin (Rv) D1, RvD5 and Protectin D1). These mediators enhance bacterial killing and clearance along with regulating phagocyte recruitment (11).

The levels of these potent leukocyte agonists decline during the later phase of the self-limited inflammatory response (11), opening the possibility that other signals may be produced that regulate leukocyte responses to promote tissue repair and regeneration. Given the pivotal roles of chemical signals in infections, the inventors investigated whether mediators within self-resolving infections could regulate tissue repair and regeneration without immunosuppression. Since maresin 1 (7R,14S-dihydroxydocosa-4Z,8E,10E,12Z,16Z,19Z-hexaenoic acid; MaR1) displays potent pro-resolving and tissue regenerative actions (12, 13), the inventors investigated whether previously undescribed signals are produced during self-limited infections that regulate tissue regeneration.

Given the desirability of identifying new compounds and methods to limit inflammation and infection, the present disclosure provides a new class of compounds acting as autacoids produced during the resolution of infections that signal innate host responses and accelerate repair.

SUMMARY OF THE DISCLOSURE

The inventors have recently identified a family of auxochrome-conjugated molecules having lipid and peptide moieties in self-resolving inflammatory exudates. The compounds have a lipid backbone and give UV chromophores characteristic of a conjugated triene double bond system coupled to an auxochrome allylic to the triene. Further elucidation of the compounds reveals that they have an oxylipin backbone conjugated to an amino acid or peptide moiety via an auxochrome. In some cases the auxochrome is sulfur. However, the auxochrome may be NH, $CH_2$ or O. The compounds have potent bioactivity, in vitro and, in vivo, including promoting resolution of infection, stimulating macrophage phagocytosis of bacteria; protecting tissues from neutrophil mediated damage and promoting tissue repair and preventing or limiting second organ reflow/reperfusion damage.

In various exemplary embodiments, the invention includes purified compounds comprising a docosahexaenoic acid (14-series and 17-series from DHA see FIG. 24) or eicosapentaenoic acid (EPA) 5(6), docosapentaenoic acid (DPAn-6) and its isomer DPAn-3, docosatetraenoic acid (DTAn-6); and arachidonic acid (C20:4n-6), epoxide derivatives conjugated at an epoxide carbon to an amino acid or peptide derivative via an auxochrome or a pharmaceutically acceptable salt thereof.

Therefore, in various exemplary embodiments, the invention includes, a purified compound comprising: an oxylipin or oxylipin derivative conjugated by an auxochrome to an amino acid or peptide derivative or a pharmaceutically acceptable salt of the compound. In some embodiments, the oxylipin is derived from eicosapentaenoic acid, docosahexaenoic acid, docosapentaenoic acid, docosatetraenoic acid or arachidonic acid. In some of these exemplary embodiments, the auxochrome is: S, NH, $CH_2$, or O.

In various other of these exemplary embodiments, the amino acid or peptide derivative is: glutathione cysteine, glycine, cysteinylglycinyl, methionine, homocysteine, taurine or S-adenosylmethionine, In still other exemplary embodiments, this disclosure provides a compound having a general formula I-X.

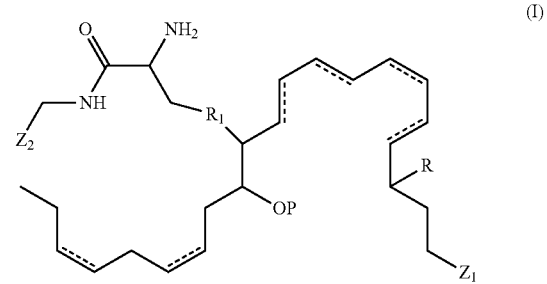

(I)

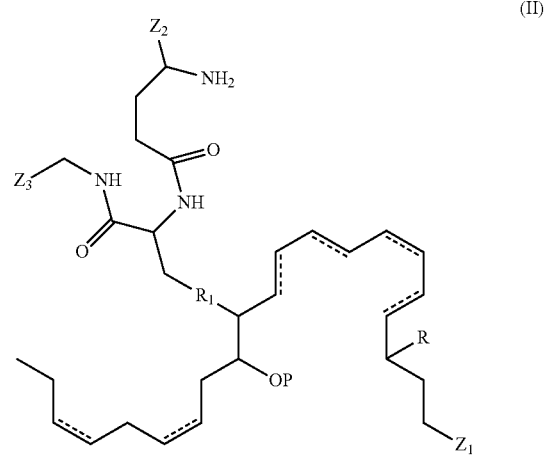

(II)

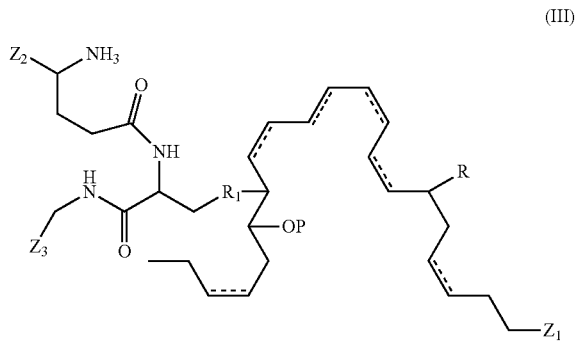

(III)

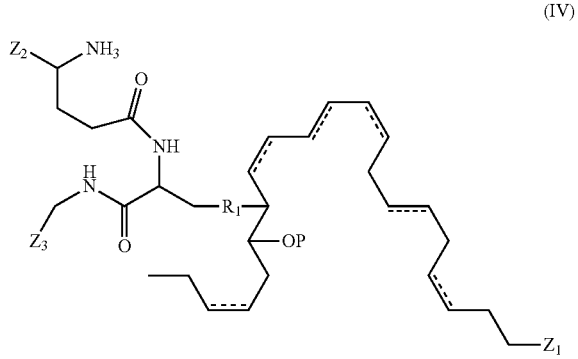

(IV)

-continued

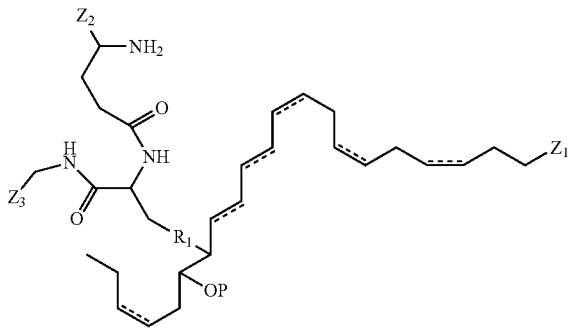
(V)

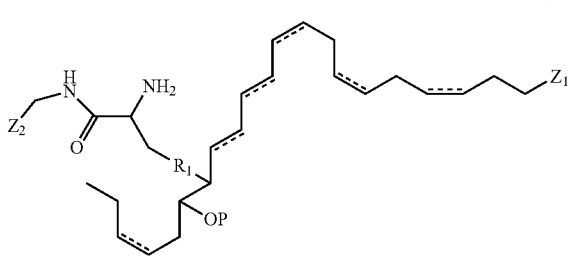
(VI)

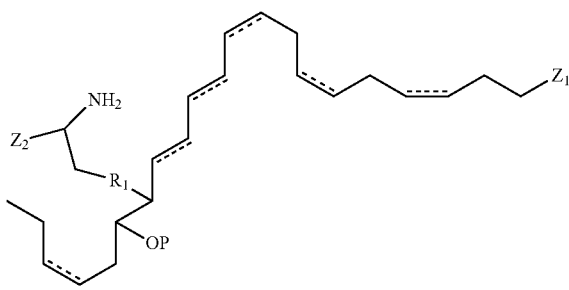
(VII)

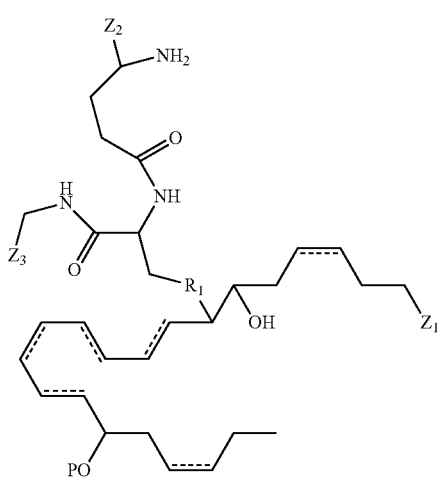
(VIII)

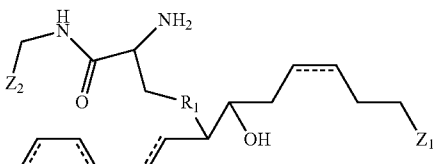
(IX)

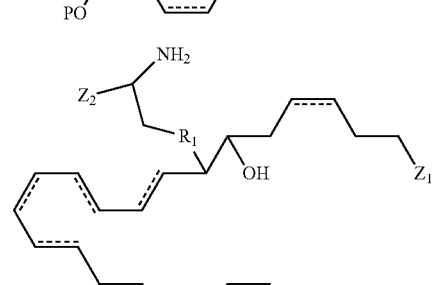
(X)

In these embodiments, each P, when present, individually is a protecting group or a hydrogen atom;

wherein ═══ is a double bond;

wherein each double bond is independently in the E or Z configuration;

wherein $Z_1$, $Z_2$ and $Z_3$, when present, individually is $C(O)OR^d$, —$C(O)NR^cR^c$, —$C(O)H$, —$C(NH)NR^cR^c$, —$C(S)H$, —$C(S)OR^d$, —$C(S)NR^cR^c$, or —CN; each $R^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each $R^c$, is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^b$ is independently selected from ═O, —$OR^d$, (C1-C3) haloalkyloxy, —$OCF_3$, ═S, —$SR^d$, ═$NR^d$, —$NOR^d$, —$NR^cR^c$, halogen, —$CF_3$, —CN, —NC, —OCN, —SCN, —NO, —$NO_2$, ═$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$C(NH)NR^cR^c$, —$OC(NR^a)N R^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ or —$[NR^aC(NR^a)]_nNR^cR^c$;

each n, independently is an integer from 0 to 3; and each $R^d$, independently is a protecting group or $R^a$;

wherein R, when present, is independently selected from hydrogen, hydroxyl, (C1-C6)alkyl, (C3-C8), cyclohexyl, (C4-C11) (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl 4-11 membered cycloheteroalkylalkyl, 5-10 membered heteroaryl or 6-16 membered heteroarylalkyl;

wherein $R_1$ is independently selected from: S, NH, $CH_2$, or O;

or a pharmaceutically acceptable salt or ester thereof.

In various exemplary embodiments, the invention provides compound has the general structure of formula XI-XX:

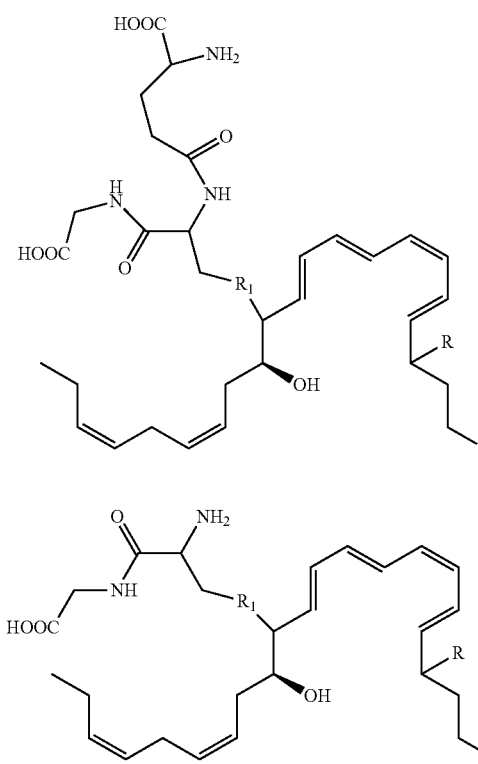

(XI)

(XII)

(XIII)

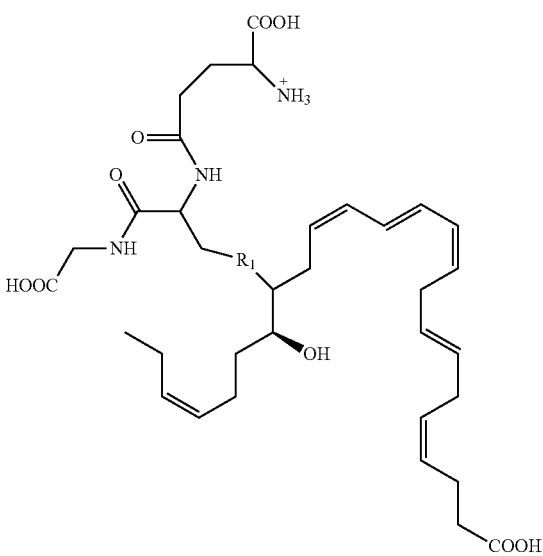

(XIV)

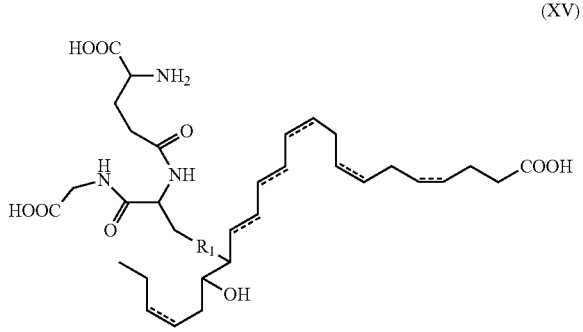

(XV)

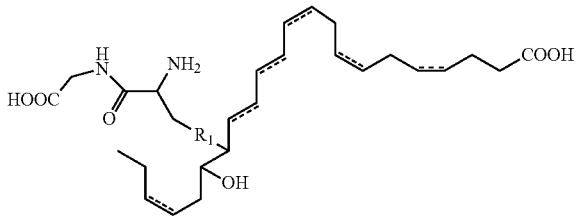

(XVI)

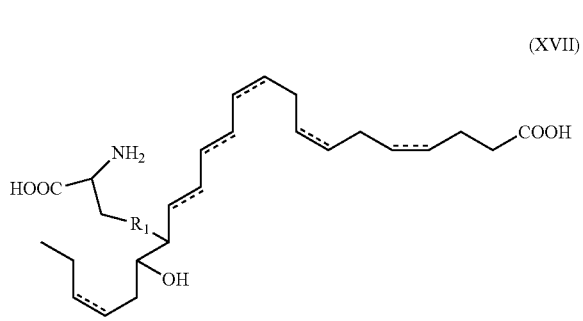

(XVII)

-continued

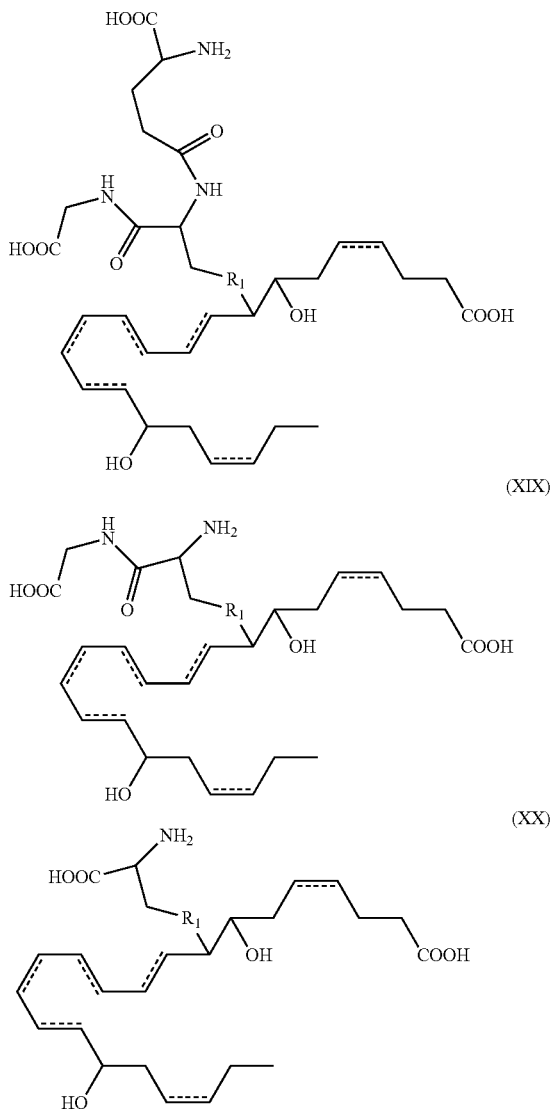

wherein R, when present, is independently selected from hydrogen, hydroxyl, (C1-C6)alkyl, (C3-C8), cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

wherein $R_1$ is independently selected from: S, NH, $CH_2$, or O;

or a pharmaceutically acceptable salt or ester thereof.

In still other exemplary embodiments, the compounds of the invention include 13-glutathionyl, 14-hydroxy-docosahexaenoic acid; 13-cysteinylglycinyl, 4-hydroxy-docosahexaenoic acid; 13-cysteinyl, 14-hydroxy-docosahexaenoic acid; 17-hydroxy, 16-glutathionyldocosahexaenoic acid, 17-hydroxy, 16-cysteinylglycinyl docosahexaenoic acid; 17 hydroxy, 16-cysteinyl docosahexaenoic acid; 7,17-hydroxy, 8-glutathionyl docosahexaenoic acid; 7,17-hydroxy, 8-cysteinylglycinyl docosahexaenoic acid; and 7,17-hydroxy, 8-cysteinyl docosahexaenoic acid; analogs thereof and pharmaceutically acceptable salts or esters thereof.

In some exemplary embodiments, the peptide or amino acid moiety is glutathione, methionine, cysteine, homocysteine, glycine, cysteinylglycinyl, taurine or S-adenosylmethionine In other exemplary embodiments, the invention includes compositions comprising compounds of the invention as disclosed herein and a pharmaceutically acceptable carrier.

In other exemplary embodiments, the invention provides a method of treating inflammation or an inflammatory disease comprising administering to a subject in need thereof a compound or composition of the invention as disclosed above as described above.

In still other exemplary embodiments, the invention provides methods for enhancing tissue regeneration comprising, administering to a subject in need thereof a compound or composition as provided above as described above.

Other exemplary embodiments of the invention provide a method for treating, ameliorating and resolving an infection comprising, administering to a subject in need thereof a compound or composition according to the invention as disclosed above as described above.

The invention provides other exemplary embodiments comprising methods of limiting or preventing second organ reflow and ischemia/reperfusion injury comprising administering to a subject in need thereof a compound or composition of the invention as described above.

The invention provides still other exemplary embodiments including a method of promoting tissue repair in a subject in need thereof comprising, administering a compound or composition of the invention as described above.

Still other exemplary embodiments of the invention provide a method of reducing pro-inflammatory eicosanoids systemically in a subject in need thereof comprising administering a compound or composition of the invention as described above.

Yet other exemplary embodiments of the invention provide a method of protecting, limiting or inhibiting neutrophil mediated tissue damage comprising, administering to a subject in need thereof a compound or composition of the invention as described above.

The invention further provides exemplary embodiments providing a method of stimulating the production of reactive oxygen species in macrophage and neutrophils comprising administering to a subject in need thereof a compound or composition of the invention as described above.

Other exemplary embodiments of the invention provide a method of decreasing or limiting leukocyte migration into tissues in a subject in need thereof comprising, administering a compound or composition of the invention as described above.

These and other features and advantages of various exemplary embodiments of the methods according to this invention are described in, or are apparent from, the following detailed description of various exemplary embodiments of the methods according to this invention.

Figure 2:
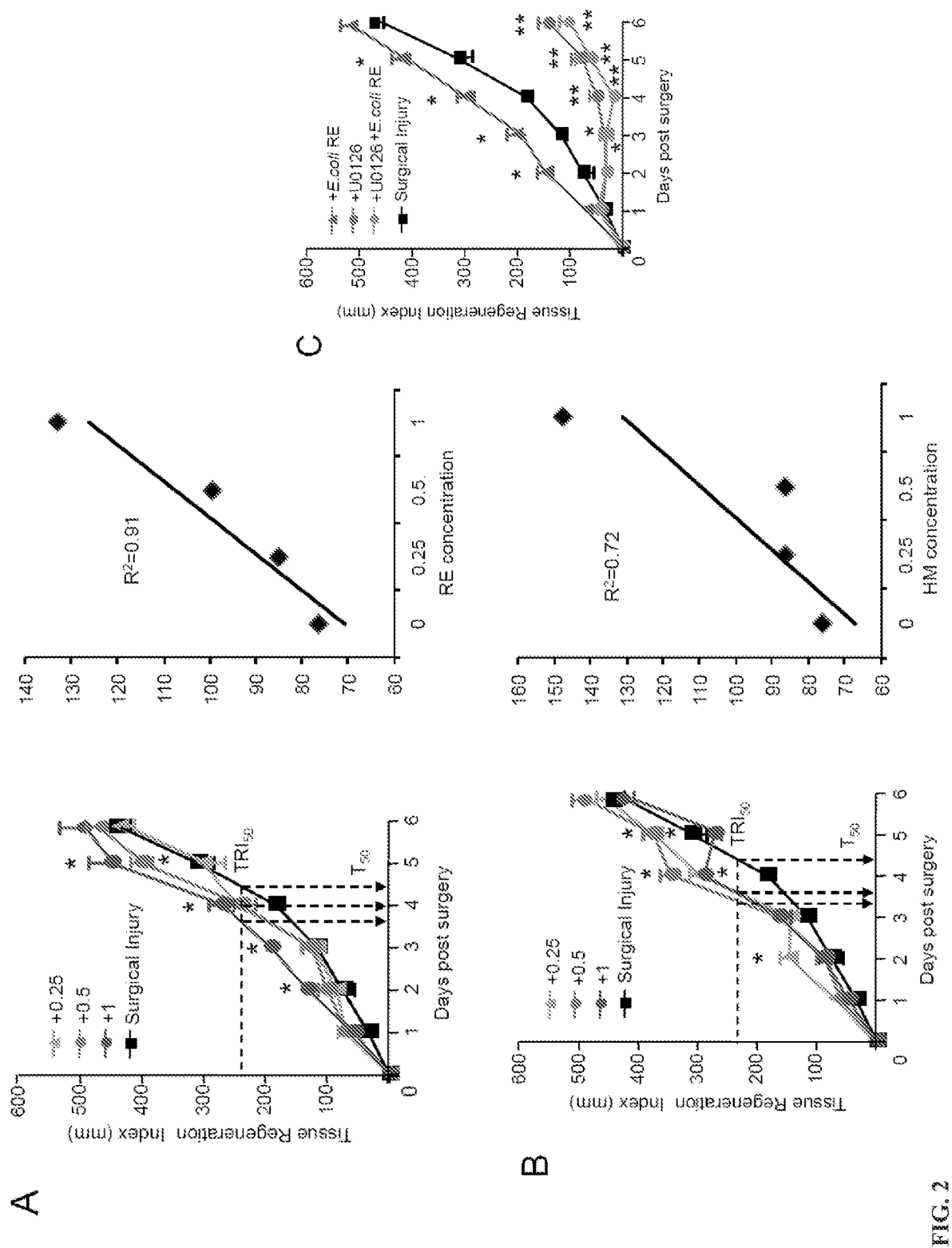

FIG. 2: Resolving murine exudate and human milk products promote tissue regeneration via ERK signaling. Planaria were surgically injured removing the head portion and incubated with decreasing concentrations (1=highest concentration; 0.5=1:1dilution; 0.25=1:4 dilution) of SPE-C isolate fraction 2 products isolated from (A) *E. coli* resolving infectious exudates (*E. coli* RE) (B) Human Milk or vehicle (Surgical Injury; water containing 0.01% EtOH) and tissue regeneration index was assessed (left panels). Right panels illustrate tissue regeneration at day 3-post surgery. (C) After surgery planaria were incubated with *E. coli* RE products (concentration=1), ERK inhibitor U0126 (25 μM), *E. coli* RE products and U0126 or vehicle. Results represent, two independent experiments and are mean±sem, n=6 planaria per incubation. *P<0.01***P<0.001 vs respective vehicle group.

Figure 3:
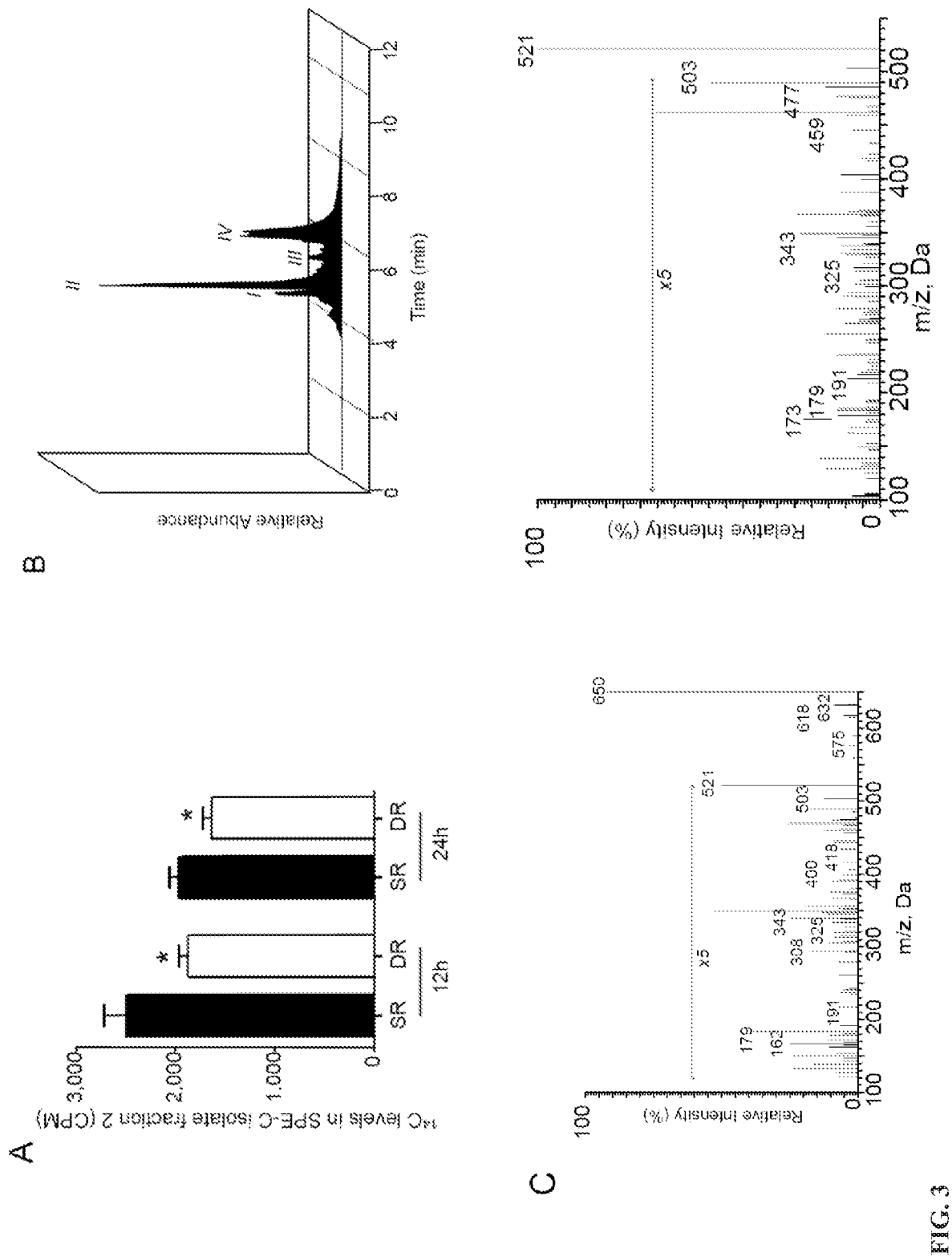

FIG. 3: In *E. coli* infected exudates DHA is converted to novel molecules: identification in human milk. Mice were inoculated with either 10$^5$ CFU (Self-resolving dose, SR) or 10$^7$ CFU (Delayed resolving dose, DR) *E. coli* and exudates collected at 12 h or 24 h. These were incubated with (A) $^{14}$C labeled docosahexaenoic acid (DHA) or (B) DHA (1 h, 37° C., PBS, pH 7.45), products were then extracted using SPE columns and $^{H}$C levels in SPE-chromatographic (SPE-C) isolate fraction 2 were measured using a scintillation counter. Results represent one experiment and are mean±sem. n=4 mice per group. *P<0.05. (B) DHA derived products were investigated using parent ion scan mode targeting on daughter ion with m/z=343 corresponding to hydroxylated-DHA. Results represent two independent experiment. n=16 mice. (C) MS-MS spectra for products in human milk with retention time of 6.2 min (left panel) and 4.4 min (right panel). Results are representative of n=6 donors.

Figure 4:
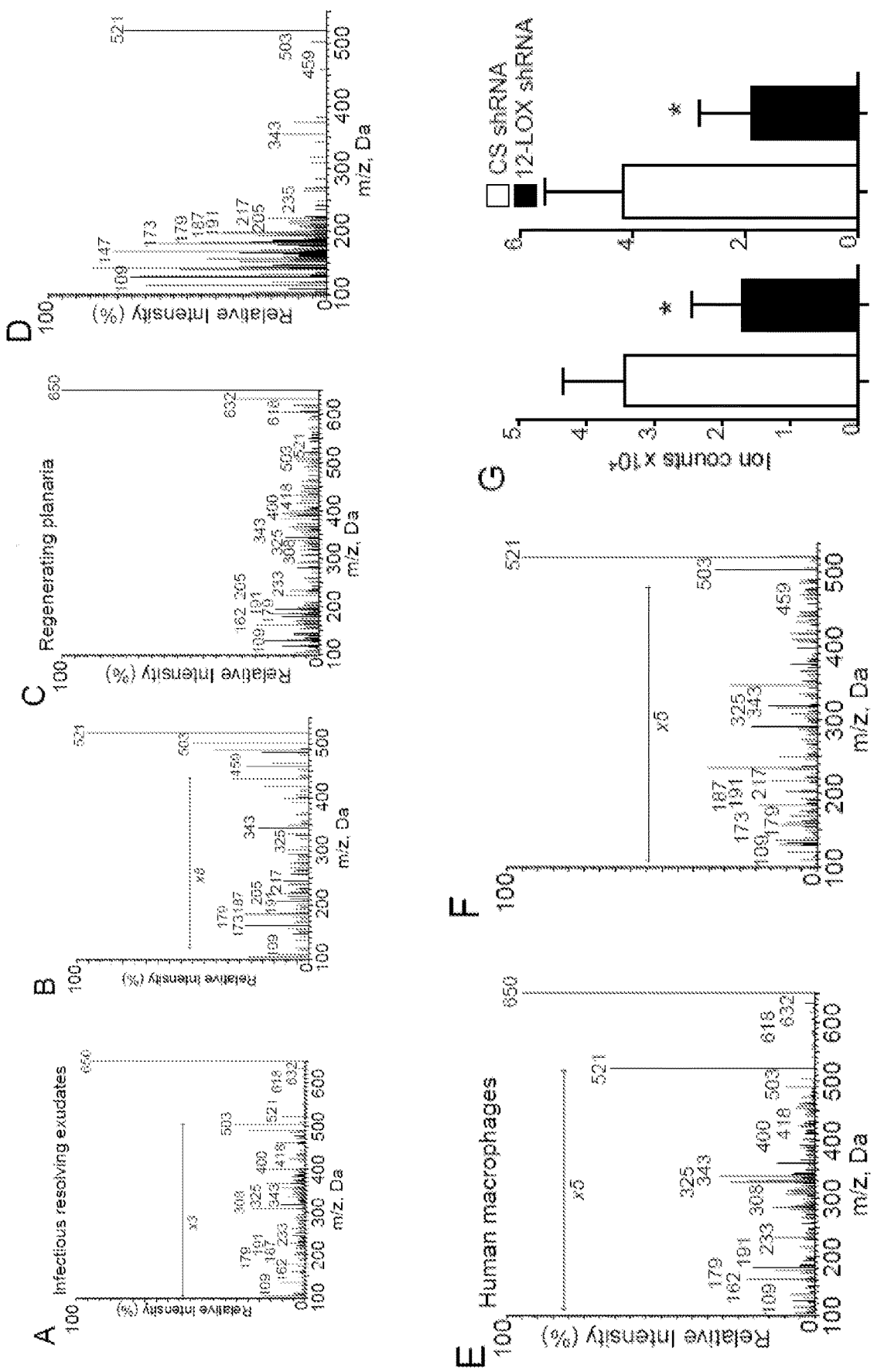

FIG. 4: Identification of previously undescribed signals in SPE-C isolate fraction 2. (A, B). Infectious exudates were obtained at 24 h after inoculation with *E. coli* (10$^5$ CFU/ mouse)). Exudates were then incubated with DHA (1 μg/ml, 37° C., 45 min), products were then extracted and signals investigated by LC-MS-MS. (A) MS-MS spectrum for signals under peaks I, II. (B) MS-MS spectrum for signals under peaks III, IV. Results are representative of n=4 mice. (C, D) Planaria were surgically injured; after 3 days products were extracted and signals investigated by LC-MS-MS. Results are representative of n=20 planaria, (E-C) Human macrophages were transfected with shRNA for 12 LOX or control scrambled (CS) sequence products were then extracted and signals investigated by LC-MS-MS. (G) MRM quantification for products under peak I and II (left panel) and under peaks III and IV (right panel). Results for E, F are representative n=3 macrophage preparations. G are mean±sem expressed as peak area ion counts. n=3 macrophage preparations. * P<0.05 vs NC transfected macrophages.

Figure 5:
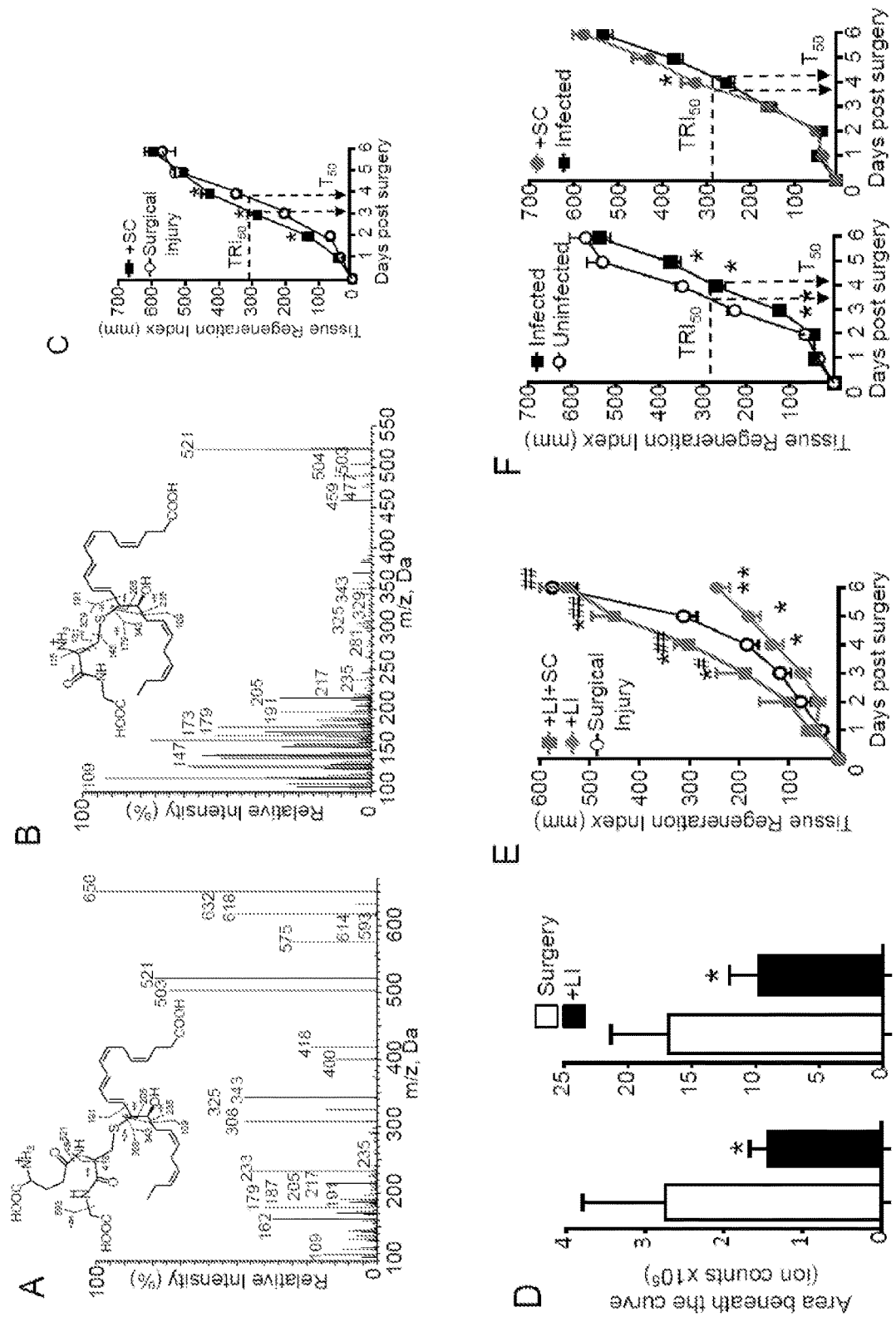

FIG. 5: New sulfido-conjugates (SC) promote regeneration, Human macrophages (1×10$^7$ cells/ml) were incubated with 14-HpDHA (1 μM, PBS$^{+/+}$) and *E. coli* (1×10$^8$ CFU/ml, 30 min, 37° C., and products isolated by RP-UV-HPLC and assessed by LC-MS-MS. Representative MS-MS spectra employed in the identification of (A) SCI from peaks III and IV; (B) SCII from peaks I and II. Results represent n=10 macrophage preparations. (C) After surgical injury, planaria were incubated with SCI plus SCII (10 nM) or vehicle (surgical injury; water containing 0.01% EtOH) and regeneration indices determined. (D) After surgical injury, planaria were incubated with lipoxygenase inhibitor (L.I.; 100 μM) or vehicle (surgical injury; water containing 0.01% EtOH). SCI and SCII were quantified by LC-MS-MS. Results are mean±sem. n=3 representative of 40 planaria per group (E). Surgically injured planaria lipoxygenase inhibitor (L.I.; 100 μM), L.I. plus SCI plus SCII (SC; 100 nM) or vehicle. (F) After surgical injury, planaria were incubated with *E. coli* (10$^8$ CFU), *E. coli* plus SCI plus SCII (100 nM) or vehicle (surgical injury; water containing 0.01% EtOH) and regeneration indices determined. Results are mean±sem. n=9 planaria per group. *p<0.05, **P<0.01 vs. respective vehicle group. #P<0.01, ##P<0.001 vs. respective L.I. group.

Figure 6:
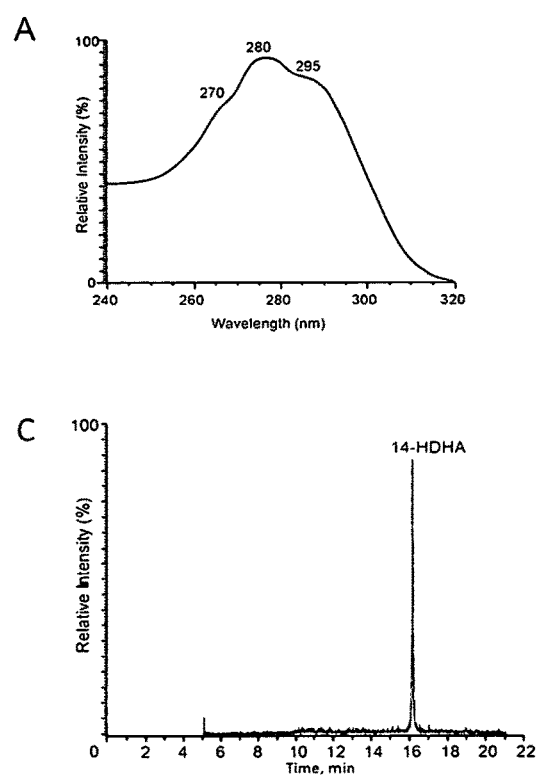
Figure 6:
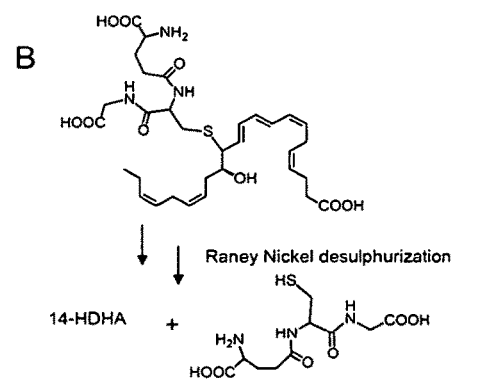
Figure 6:
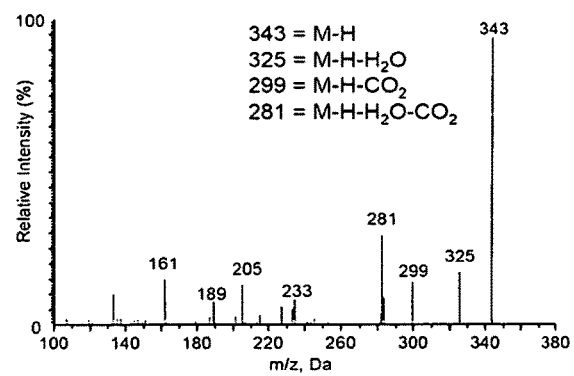

FIG. 6: Physical properties of SCI. Human macrophages (1×10$^7$ cells/ml) were incubated with 14-HpDHA (1 μM, PBS$^{-/+}$) and *E. coli* (1×10$^8$ CFU/ml, 30 min, 37° C.), and products investigated by lipid mediator metabololipidomics. (A) Online UV chromophore for SCI from human macrophages. (B, C) SCI was isolated from human macrophages incubations and reacted with activated Raney Nickel catalyst for 20 min. Products were then assessed using lipid mediator metabololipidomics, (B) Schematic depicting the anticipated products of the Raney Nickel reaction with SCI (C); Left panel: multiple reaction monitoring (MRM) chromatogram for m/z 343>205; right panel: MS-MS fragmentation pattern employed in the identification of 14-HDHA. (A, C). Results are representative of three independent experiments. n=6 preparations.

Figure 7:
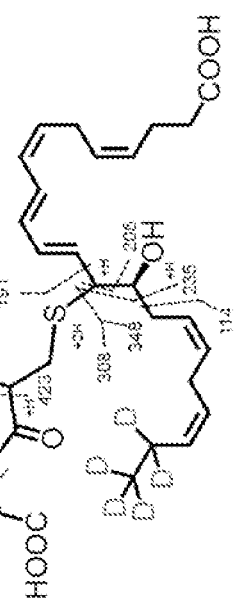
Figure 7:
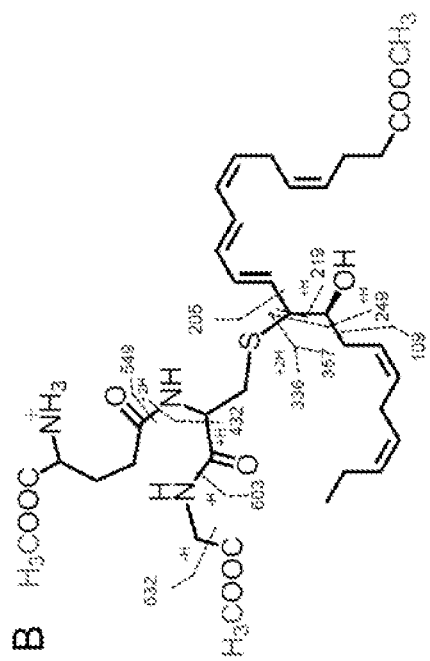

FIG. 7: Fragmentation of deuterium labeled and trimethyl ester derivatives of SCI. (A) Human macrophages (1×10$^7$ cells/rut) were incubated with d$_5$-14-HpDHA or 14-HpDHA (1 μM, PBS$^{+/+}$, pH 7.45) and *E. coli* (10$^8$ CFU/ml, 30 min, 37° C.), and products investigated by lipid mediator metabololipidomics (see methods). (B) Human macrophages (1×10$^7$ cells/ml) were incubated with 14-HpDHA (1 μM, PBS$^{+/+}$) and *E. coli* (10$^8$ CFU/ml, 30 min, 37° C.), products were extracted then incubated with diazomethane in diethyl ether (see methods). (C) Diagnostic ions employed in the identification of SCI and the corresponding ions for the two derivatives. Red and blue delineate the portions of the molecule that were modified and the corresponding ions. Results represent three independent experiments, n=10 cell preparations.

Figure 8:
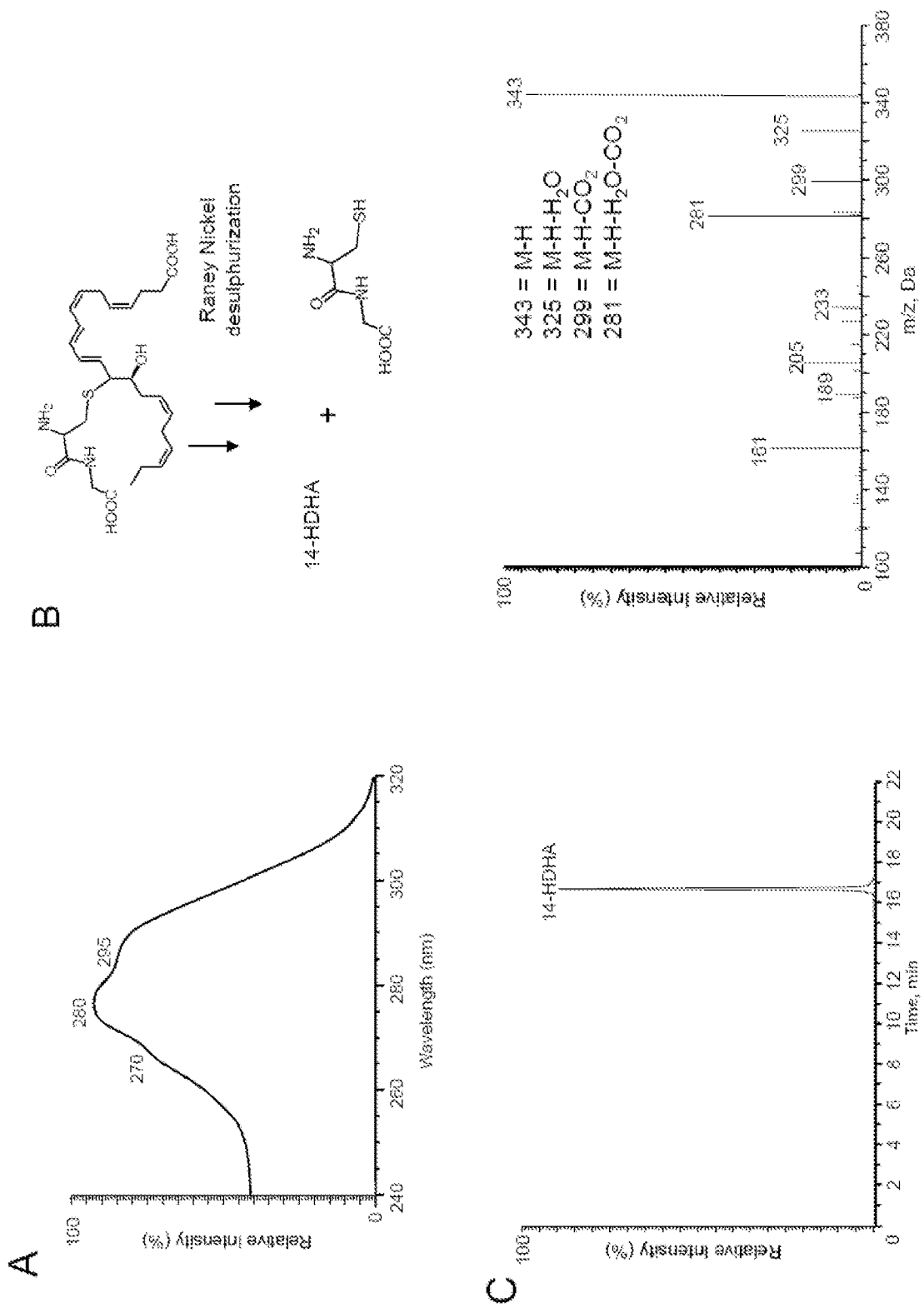

FIG. 8: Physical properties of SCII. Human macrophages (1×10$^7$ cells/ml) were incubated with 14-HpDHA. (1 μM, PBS$^{+/+}$) and *E. coli* (10$^8$ CFU/ml, 30 min, 37° C.), and products investigated by lipid mediator metabololipidomics. (A) Online UV chromophore for SCII from human macrophages. (B, C) SCII was isolated from human macrophages incubations and reacted with activated Raney Nickel catalyst for 20 min. Products were then assessed using lipid mediator metabololipidomics, (B) Schematic depicting the anticipated products of the Raney Nickel reaction with SCII. (C) Left panel: multiple reaction monitoring (MRM) chromatogram for m/z 343>205; right panel: MS-MS fragmentation pattern employed in the identification of 14-HDHA. (A, C) Results represent three independent experiments. n=6 cell preparations.

Figure 9:
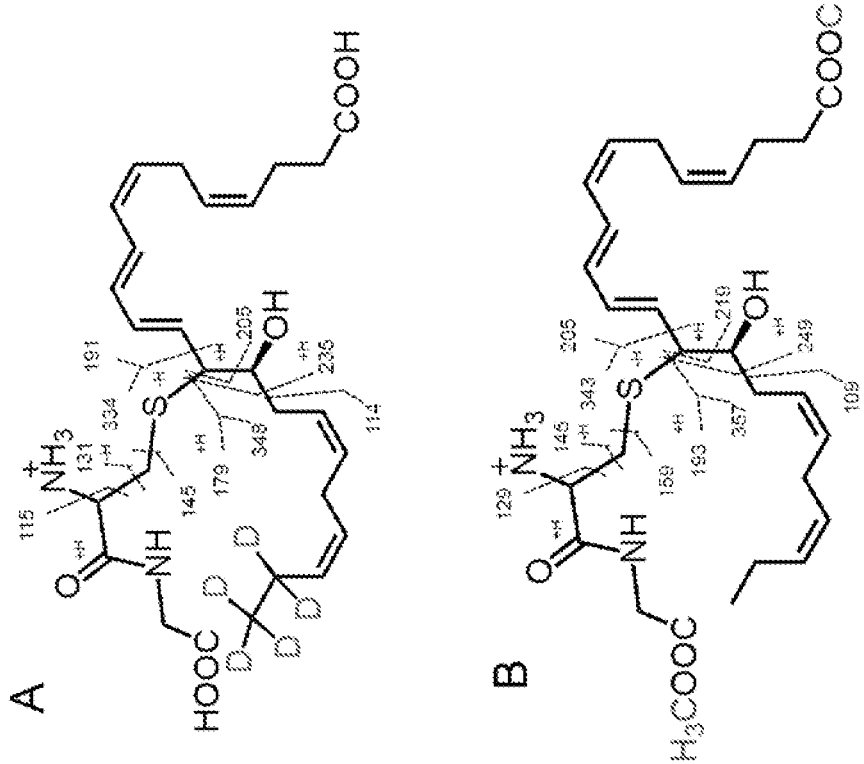

FIG. 9: Fragmentation of deuterium labeled and dimethyl ester derivatives of SCII. (A) Human macrophages (1×10$^7$ cells/ml) were incubated with d$_5$-14-HpDHA or 14-HpDHA (1 μM, PBS$^{+/+}$, pH 7.45) and *E. coli* (10$^8$ CFU/ml, 30 min, 37° C.) and products investigated by lipid mediator metabololipidomics (see methods). (B) Human macrophages (1×10$^7$ cells/ml) were incubated with 14-HpDHA (1 μM, PBS$^{+/+}$) and *E. coli* (10$^8$ CFU/ml, 30 min; 37° C.), products were extracted then incubated with diazomethane in diethyl ether (see methods). (C) Diagnostic ions employed in the identification of SCII and the corresponding ions for the two derivatives. Red and blue delineate the portions of the molecule that were modified and the corresponding ions. Results represent five independent experiments. n=10 cell preparations.

Figure 10:
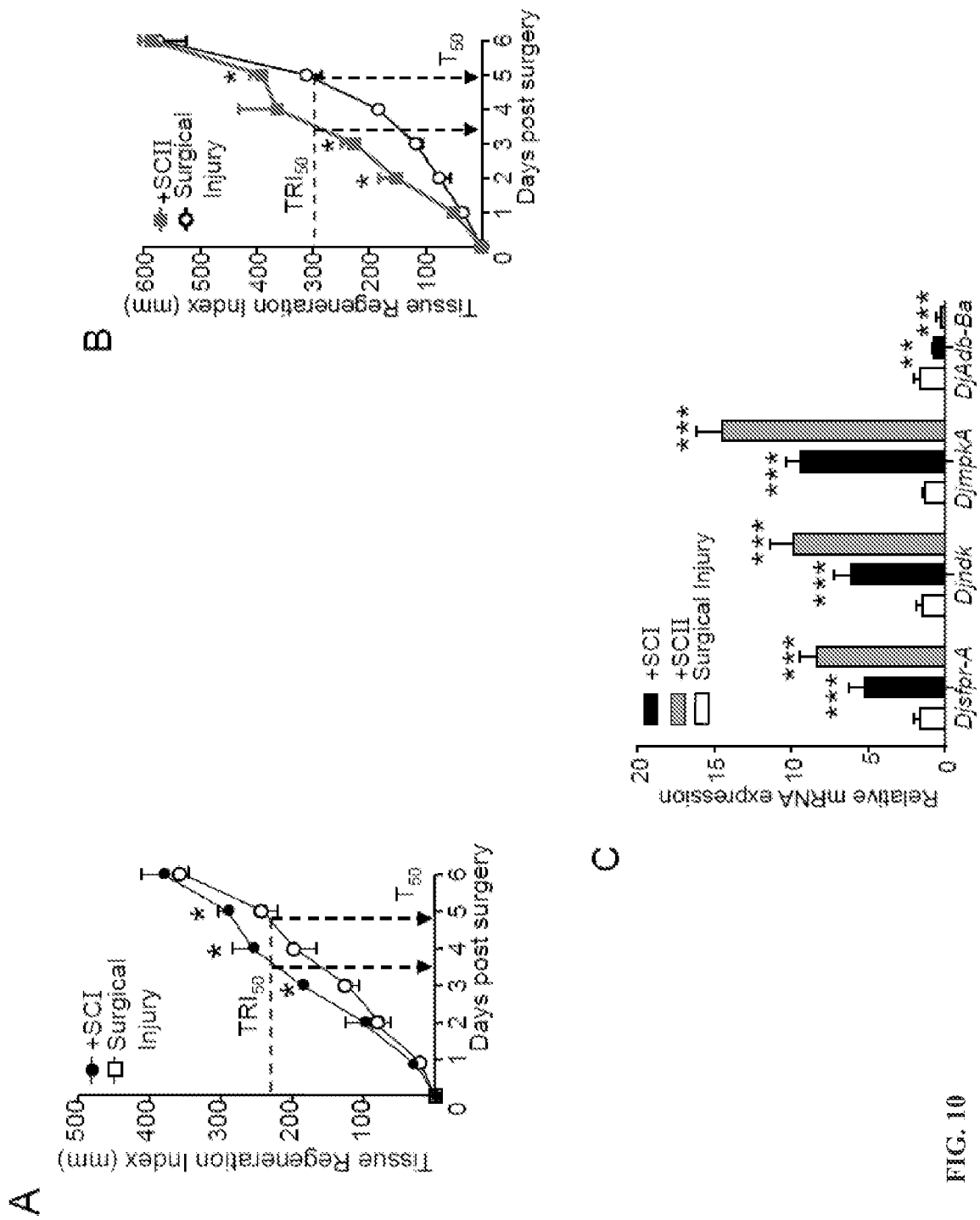

FIG. 10: SCI and SCII promote tissue regeneration and regulate key signaling pathways in planaria. After surgical injury, planaria were incubated with (A) SCI (100 nM), (B) SCII (100 nM) or vehicle (surgical injury; water containing 0.01% EtOH) and regeneration indices determined. Results represent two independent experiments and are mean±sem, n=9 planaria per group. (C) After surgical injury planaria were incubated with SCI (100 nM), SCII (100 nM) or vehicle and gene expression assessed 2 days post injury in regenerating head blastemas. Results are mean±sem. n=3 per incubation pooled from blastemas of 9 animals. *P<0.05, P<0.01, *P<0.01 vs Surgical Injury group.

Figure 11:
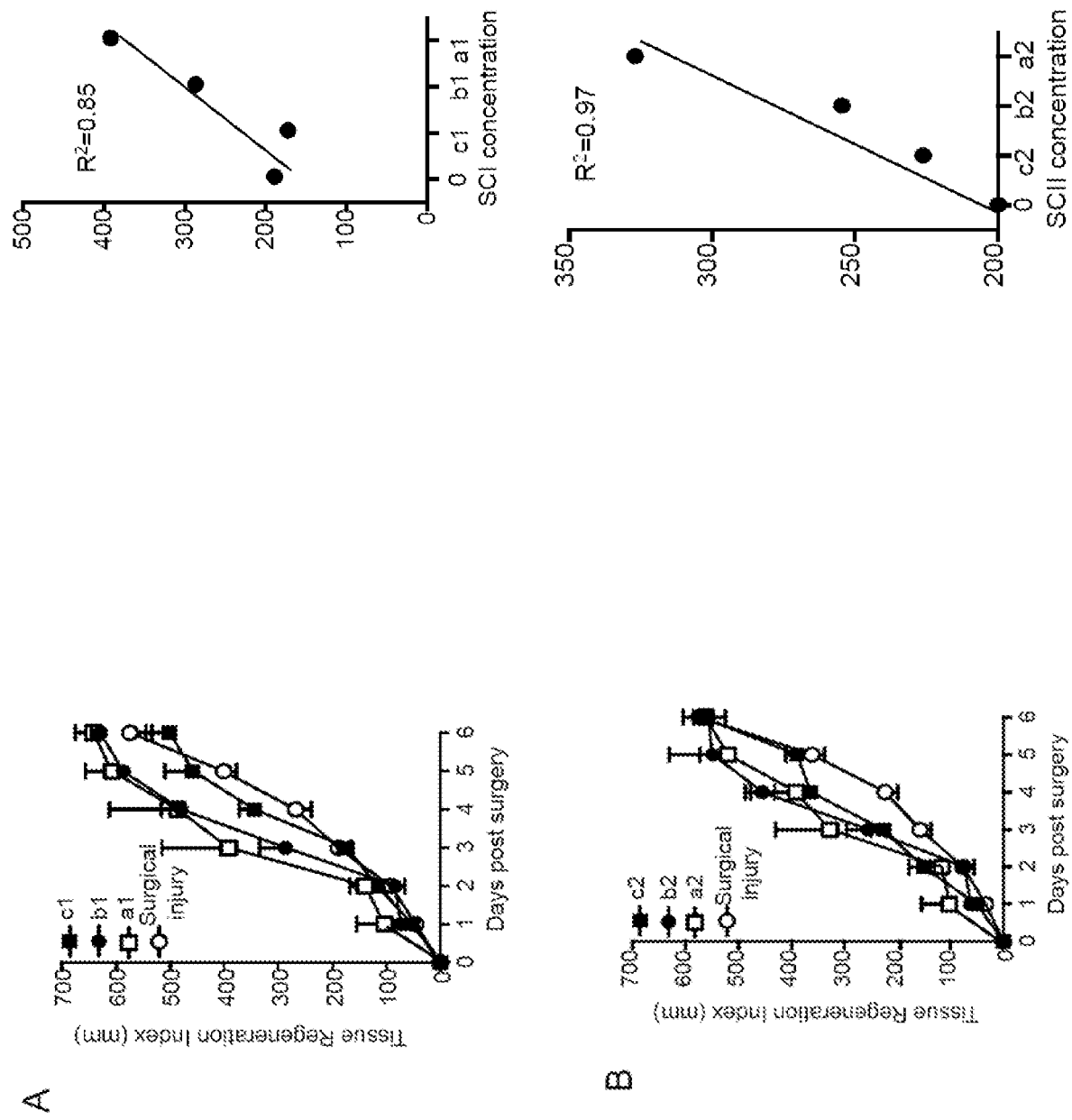

FIG. 11: SCI and SCII each display dose dependent actions in tissue regeneration. Planaria were surgically injured removing the head portion and incubated with the indicated concentrations of (A) SCI and (B) SCII and tissue regeneration assessed over time. SCI and SCII were isolated by RP-HPLC and concentration determined by multiple reaction monitoring of selected ion pairs (650>308 for SCI and 521>179 for SCII). The amounts are displayed as area beneath the curve at retention time 6.2 min for SCI and 4.4 min for SCII. Where a1=3.2×10$^5$, b1=32×10$^5$, c1=320×10$^5$, a2=3.8×10$^5$, b2=38×10$^5$, c2=380×10$^5$ ion counts. Results represent one experiment and are mean±sem n=6 planaria per incubation. Right panels illustrate tissue regeneration at day 3-post surgery.

Figure 12:
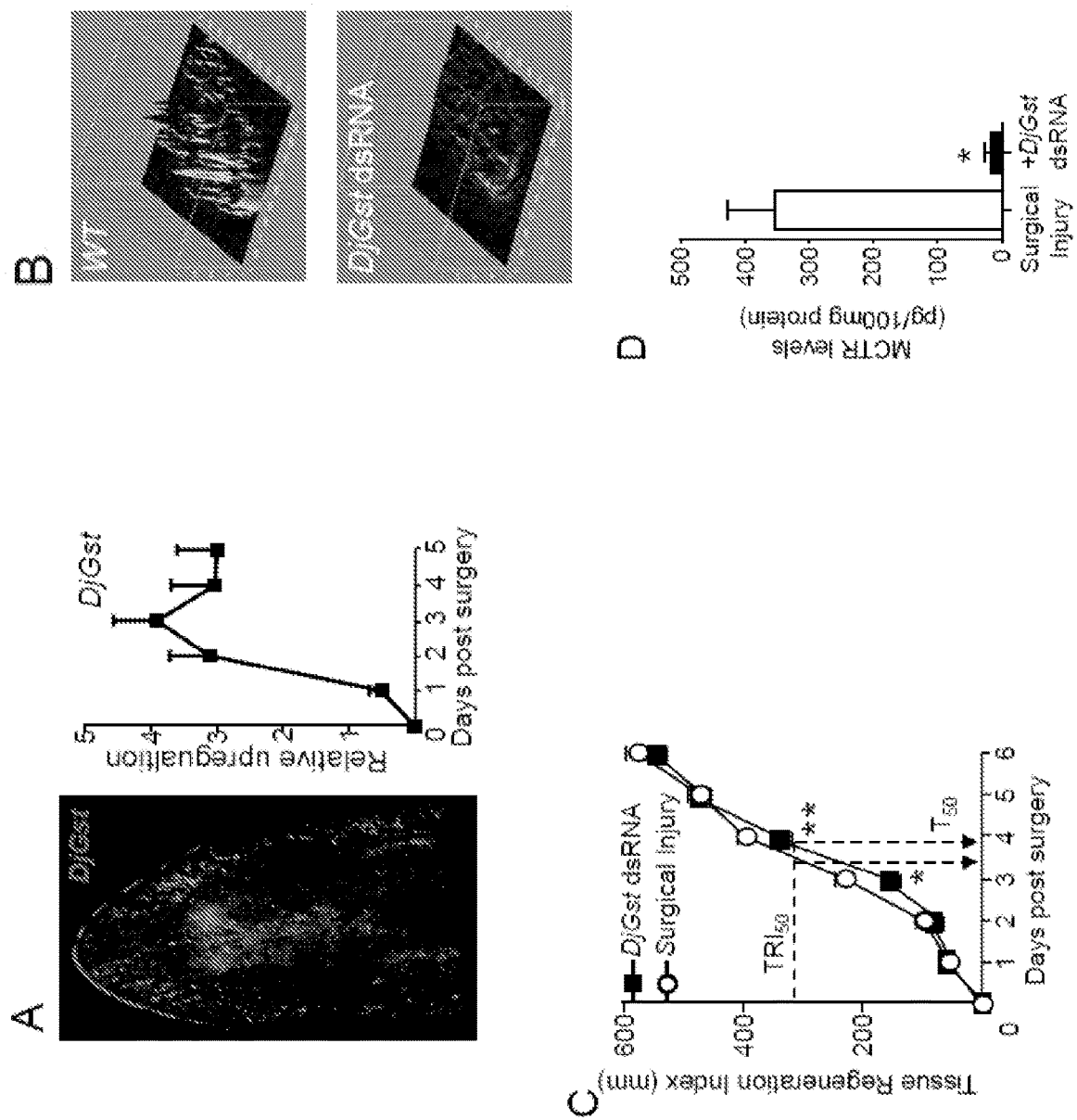

FIG. 12: Regulation of tissue regeneration and SC production by planaria GST. (A) DjGst expression by WISH in uninjured animals (left panel; representative n=9) and time course for DjGst expression in regenerating blastemas (Right panel; mean±sem, n=4 per interval pooled from blastemas of 12 animals). (B-D) Planaria were fed homogenized beef liver containing DjGst dsRNA or beef liver (WT). (B) After 8 days DjGst expression was assessed by WISH, (C) tissue regeneration kinetics were determined. (D) SC levels 3 days post surgery. Results are mean±sem. n=13 planaria per group. *P<0.05, **P<0.01 vs surgical injury group.

Figure 13:
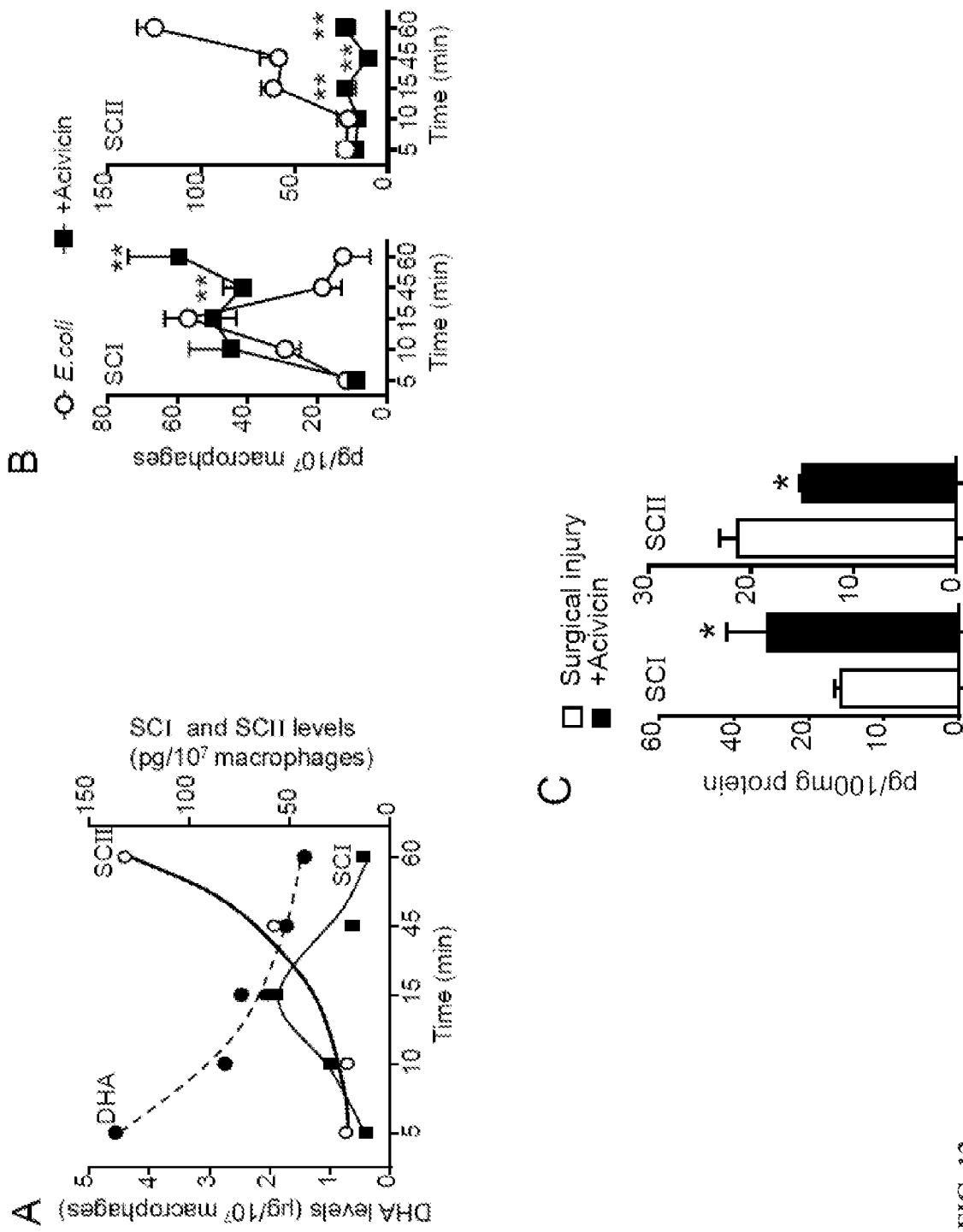

FIG. 13: Endogenous SCI is converted to SCII with human macrophages and planaria. (A) Human macrophages (3×10$^7$ cells) were incubated with DHA (1 μg, 37° C., pH 7.45) and *E. coli* (1.5×10$^8$ CFU) and product levels were assessed using LC-MS-MS. Results are mean, n=3 separate incubations. (B) Human macrophages were incubated with or without γ-glutamyl transferrase (GTI; 2.5 mM, 37° C., pH 7.45, 30 min) then DHA (1 μg, 37° C., pH 7.45) and *E. coli* (1.5×10$^8$ CFU), precursor and product levels were assessed by LC-MS-MS. Results are mean±sem. n=3 distinct incubations. (C) Planaria were surgically injured then incubated with or without GTI (2.5 mM). SCI and SCII were assessed 3 days after injury using LC-MS-MS. Results are mean±sem, n=20 planaria per group.*P<0.05 vs surgical injury group, **P<0.01 vs Macrophages+*E. coli*.

Figure 14:
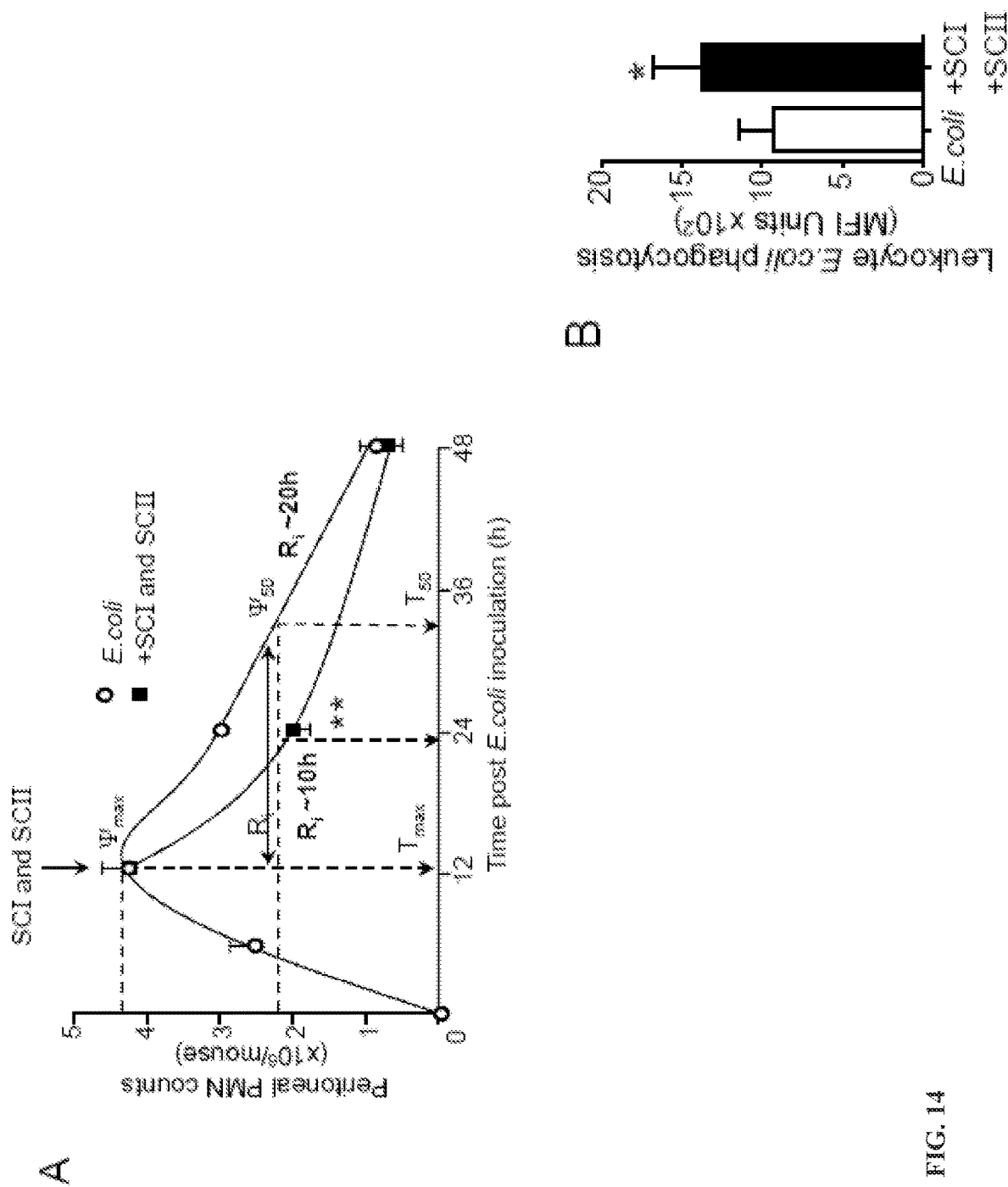

FIG. 14: SC resolve infection and stimulate efferocytosis. (A, B) Mice were inoculated with *E. coli* (10$^5$ CFU/mouse, i.p.) followed by either SCI plus SCII (50 ng/mouse each; i.p) or vehicle (saline containing 0.1% EtOH) 12 h later, (A) Peritoneal leukocyte counts and resolution indices (see methods). (B) In vivo *E. coli* phagocytosis. Results are mean±sem. n=4 mice per interval, *P<0.05, **P<0.01 vs. *E. coli*. (C) Human macrophages (5×10$^4$ cells/well) were incubated with SCI (left panel), SCII (right panel) or MaR1, fluorescently labeled apoptotic PMN and efferocytosis assessed. Results are mean±sem. n=4 macrophage preparations. *P<0.05, **P<0.01 vs vehicle group.

Figure 15:
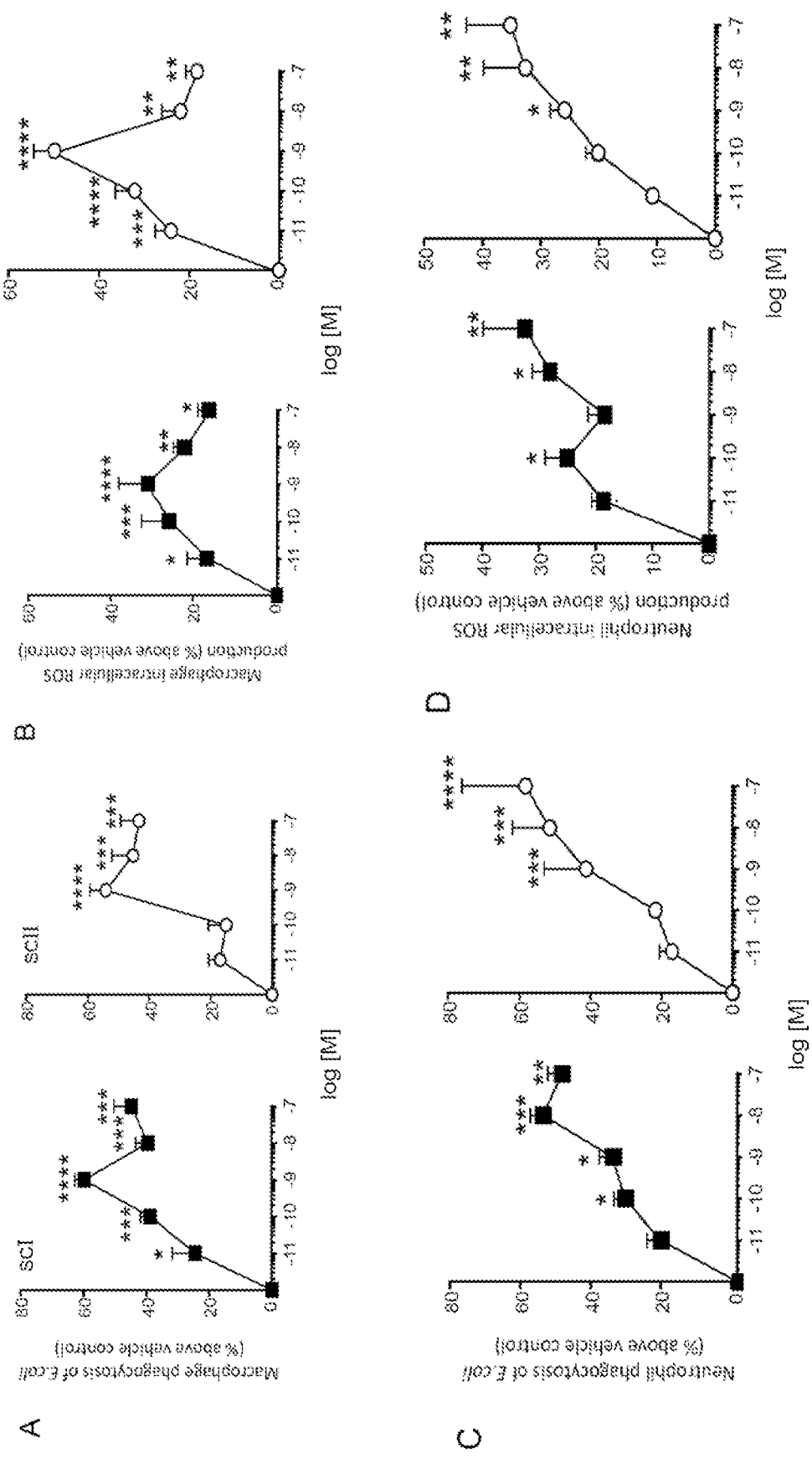

FIG. 15: SCI and SCII promote bacterial phagocytosis and killing with human leukocytes. (A) Human macrophages (5×10$^4$ cells per well) were incubated with vehicle (PBS containing 0.1% EtOH), SCI or SCII (at the indicated concentrations, 15 min, 37° C.). Fluorescently labeled *E. coli* (2.5×10$^6$ CFU) were then added and phagocytosis was assessed after 45 min using a fluorescence plate reader. (B) Human macrophages were incubated with H$_2$DCFDA (5 μM, 30 min at 37° C.) followed by vehicle, SCI or SCII (at the indicated concentrations, 15 min, 37° C.). *E. coli* (2.5×10$^6$ CRT) were added and ROS levels assessed after 45 min using a fluorescence plate reader. (C) Human neutrophils (1×10$^5$ cells per well) were incubated with vehicle (saline containing 0.1% EtOH), SCI or SCII (at indicated concentrations, 15 min, 37° C.). Fluorescently labeled *E. coli* (5×10$^6$ CFU) were then added and phagocytosis was assessed after 45 min using a fluorescence plate reader. (D) Human neutrophils were incubated with H$_2$DCFDA (5 μM, 30 min at 37° C.) followed by vehicle, SCI or SCII (at the indicated concentrations, 15 min, 37° C.). *E. coli* (5×10$^6$ CFU) were added and ROS levels were assessed after 45 min using a fluorescence plate reader. Results represent two independent experiments and are expressed as mean±sem. n=4 independent cell preparations. *P<0.05, P<0.01, *P<0.001, ****P<0.0001 vs *E. coli* alone.

Figure 16:
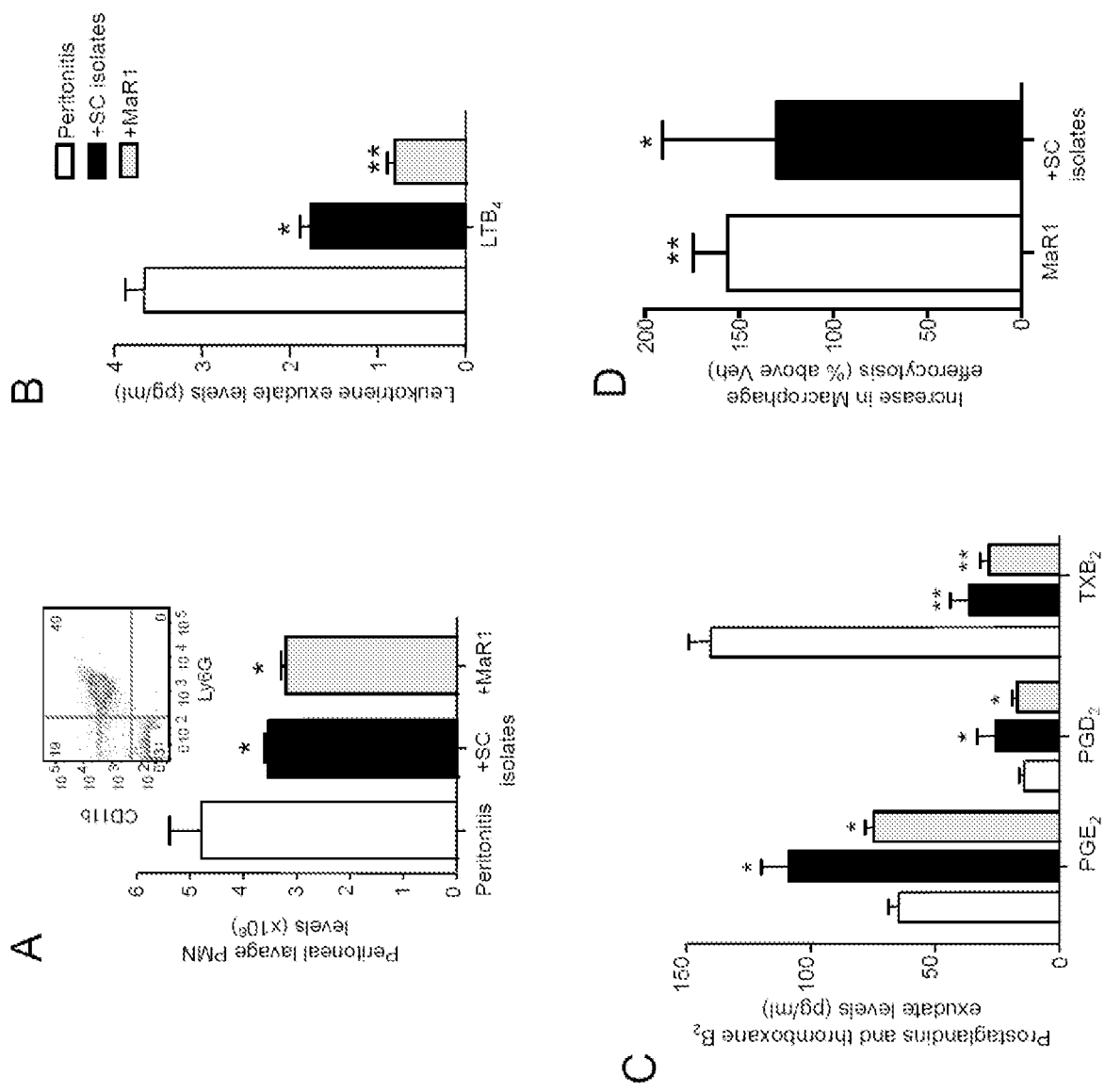

FIG. 16: SC isolates from regenerating planaria display potent anti-inflammatory and pro-resolving actions. Planaria were surgically injured and isolates obtained 3 days after injury (see methods). (A-C) Mice were administered planarian SC isolates from regenerating planaria 3 days after injury, MaR1 (10 ng) or vehicle (saline containing 0.1% EtOH; Peritonitis), i.p. 10 min prior to 1 mg zymosan administration. (A) Peritoneal cells counts were assessed after 4 h by light microscopy and flow cytometry (see methods). (Inset) Representative flow cytometry dot plot of 4 h exudate leukocytes. Exudate (B) leukotriene and (C) prostanoids were identified by lipid mediator metabololipidomics (see methods). Results represent one experiment and are mean±sem. n=3 mice per treatment. *P<0.05, **P<0.01 vs vehicle administered mice. (D) Human macrophages (5×10$^4$ cells per well) were incubated with MaR1 (10 nM), planarian SC isolates or vehicle (PBS containing 0.01% EtOH, 10 min 37° C.). Fluorescently labeled apoptotic neutrophils (1.5×10$^5$ cells per well) were then added and phagocytosis assessed after 45 min (37° C.) using fluorescence plate reader. Results represent two independent experiments and are mean±sem. n=3 independent cell preparations. *P<0.05, **P<0.01 vs macrophages incubated with vehicle alone.

Figure 17:
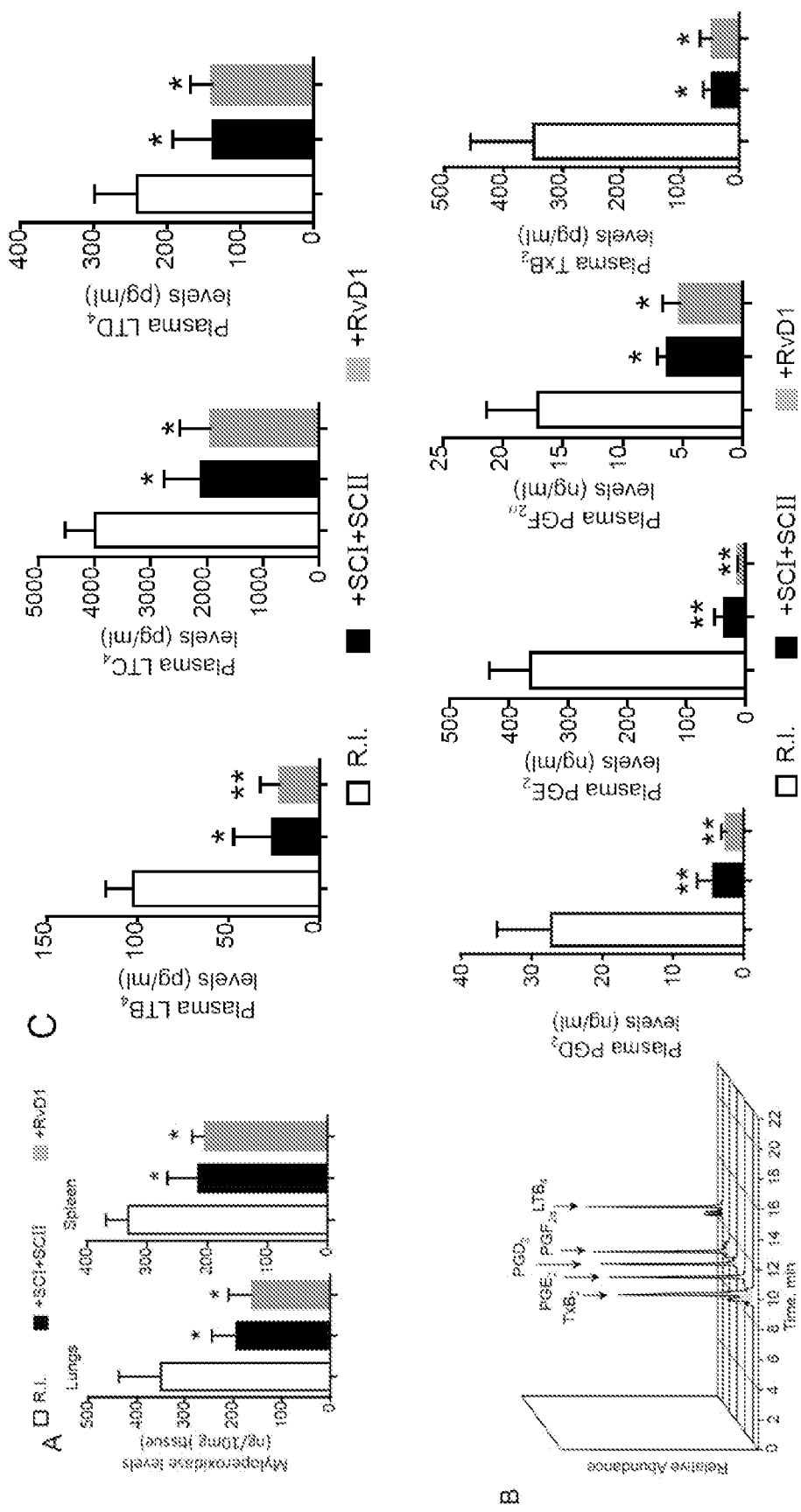

FIG. 17: Reduction in systemic pro-inflammatory eicosanoids and protection from second organ injury by SCI and SCII. Hind limb ischemia was initiated by applying tourniquets to mice hind limbs. After 1 h, tourniquets were removed and reperfusion ensued for 3 h (Reflow injury; R.I.). 10 min prior to reperfusion, vehicle (saline containing 0.1% EtOH), SCI plus SCI (black bars; 100 ng) or RvD1 (grey bars; 500 ng) were administered i.v. at the end of reperfusion, (A) spleens and lungs were harvested and MPO levels were assessed. (B, C) Plasma was collected via cardiac puncture and peripheral blood eicosanoid levels were investigated by lipid mediator metabololipidomics (see methods). (B) MRM chromatograms for select identified mediators (C) peripheral blood eicosanoid levels. Results represent two independent experiments and n=12. mice. Results for A, C are mean±sem n=4 mice per group. *P<0.05, **P<0.01 vs vehicle treated mice.

Figure 18:
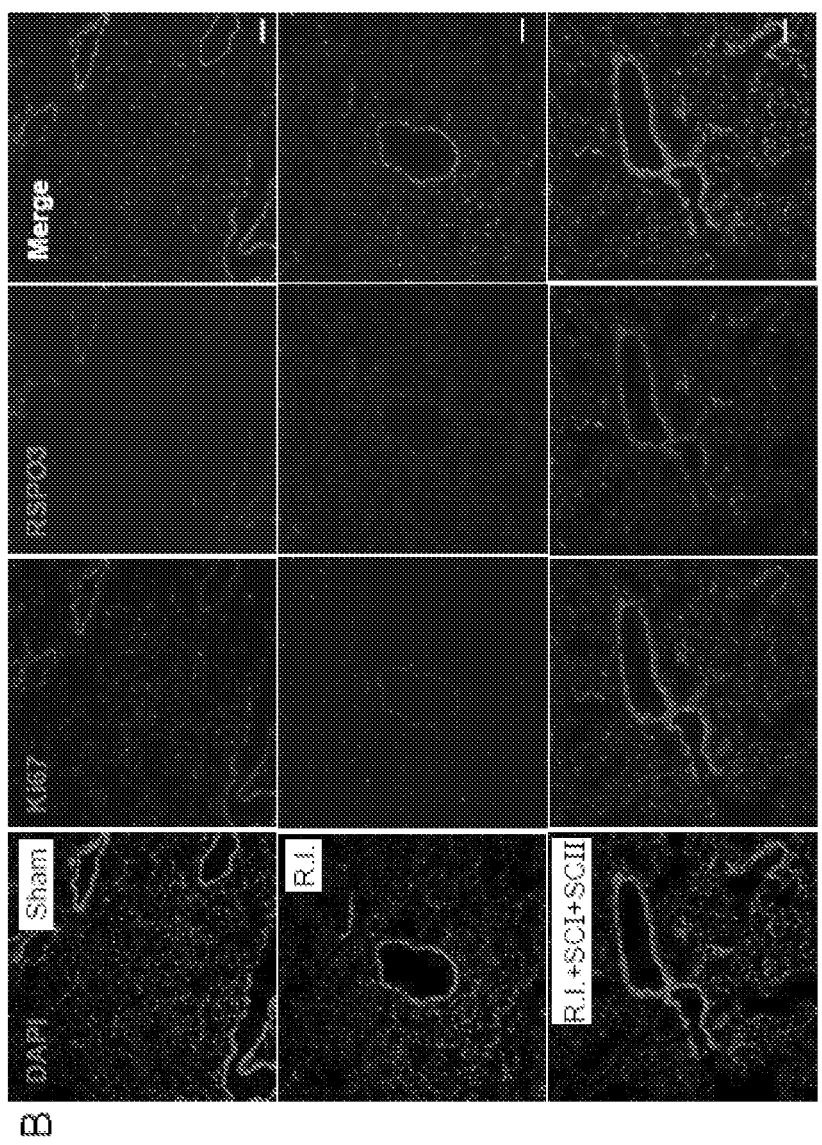

FIG. 18: SC are organ protective. Mice were subjected to hind-limb ischemia (1 h) followed by reperfusion (3 h). 10 min prior to reperfusion, vehicle (saline containing 0.1% EtOH; reflow injury: R.I.), SCI plus SCII (50 ng each) were administered i.v. Lungs were then collected, (A) tissue H&E staining (bar=100 μm). Black arrows: leukocyte mediated tissue damage; blue arrows: intact alveolar regions. (B) Immunofluorescence staining, Nuclear material (DP AI-Blue), Ki67 (Alexa-488-Green), RSPO3 (Alexa-594-Red) (bar=100 μm). Results are representative n=4 mice per group.

Figure 19:
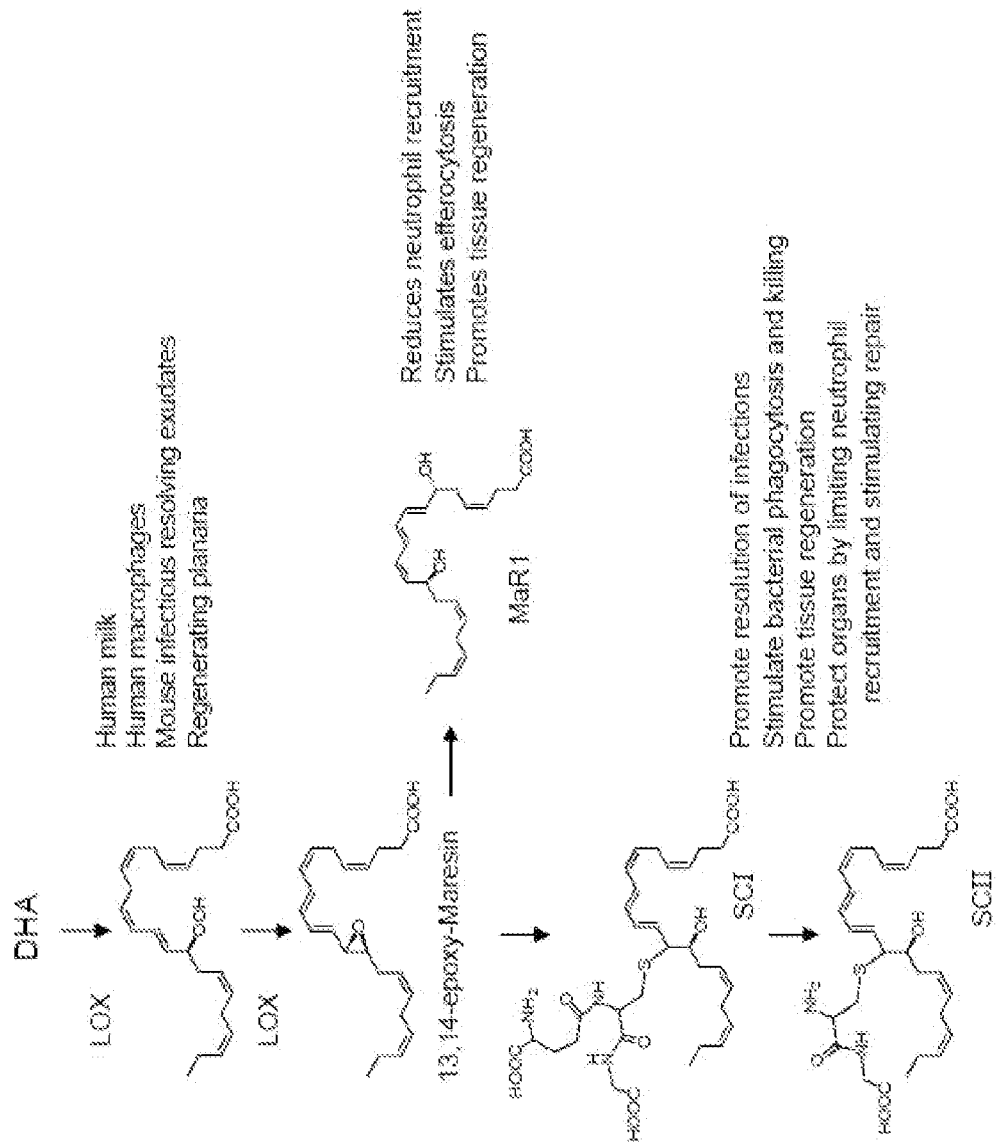

FIG. 19: Proposed SC biosynthetic scheme. Structures are depicted in likely conformations based on biosynthetic evidence (see text and Table S1 for further detail). The stereochemistry of Maresin I and the triaresin epoxide intermediate are established (21).

Figure 20:
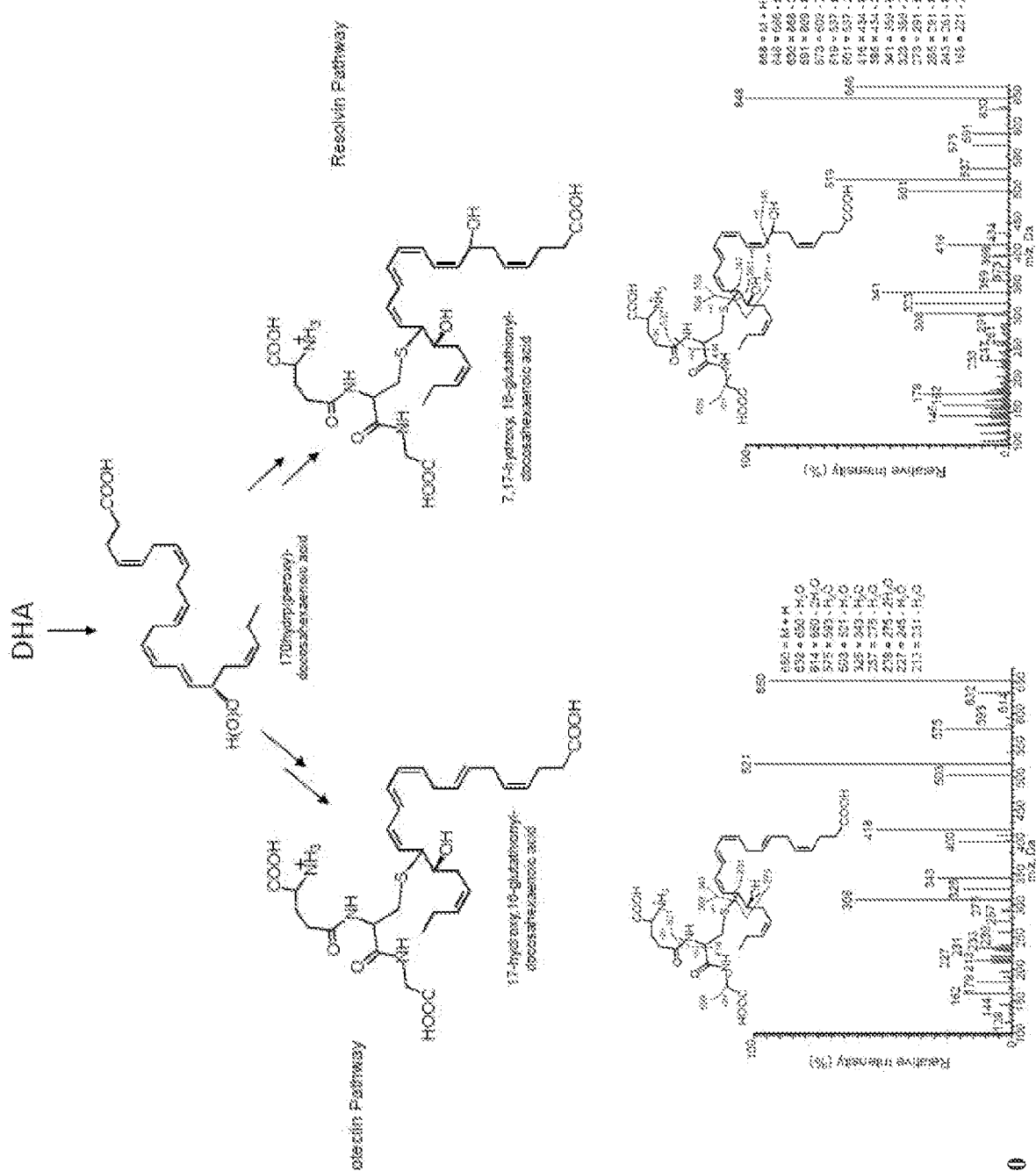

FIG. 20: Proposed Protectin and D-series resolvin SC biosynthetic scheme: MS-MS spectra. Human macrophages ($1 \times 10^7$ cells m) were incubated with 17-HpDHA (1 μM, $PBS^{+/+}$) and E. coli ($1 \times 10^8$ CFU/ml, 30 min, 37° C.), and products assessed by LC-MS-MS. Representative MS-MS spectra employed in the identification of 17-hydroxy, 16-glutathionyl-docosahexaenoic acid (Left panel) and 7,17-hydroxy, 16-glutathionyl-docosahexaenoic acid (right panel). Results are representative of n=10 incubations.

Figure 21:
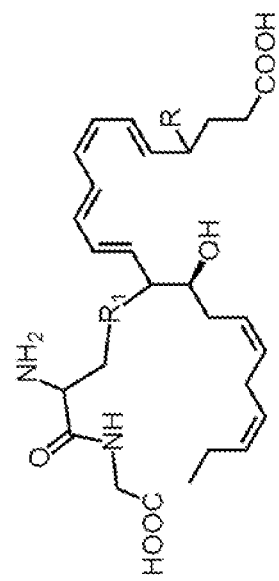
Figure 21:
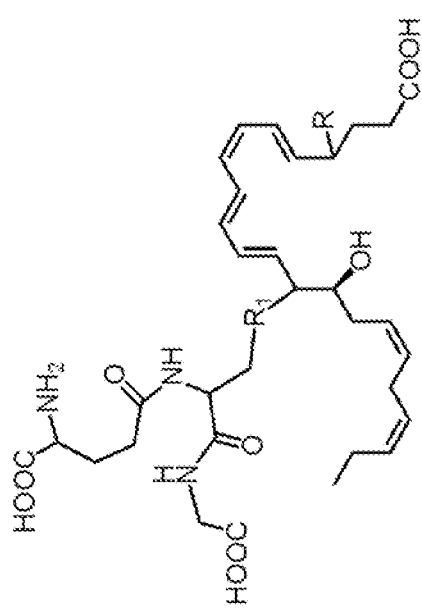

FIG. 21: Examples of stable mimetics of SPM conjugates are provided.

Figure 22:
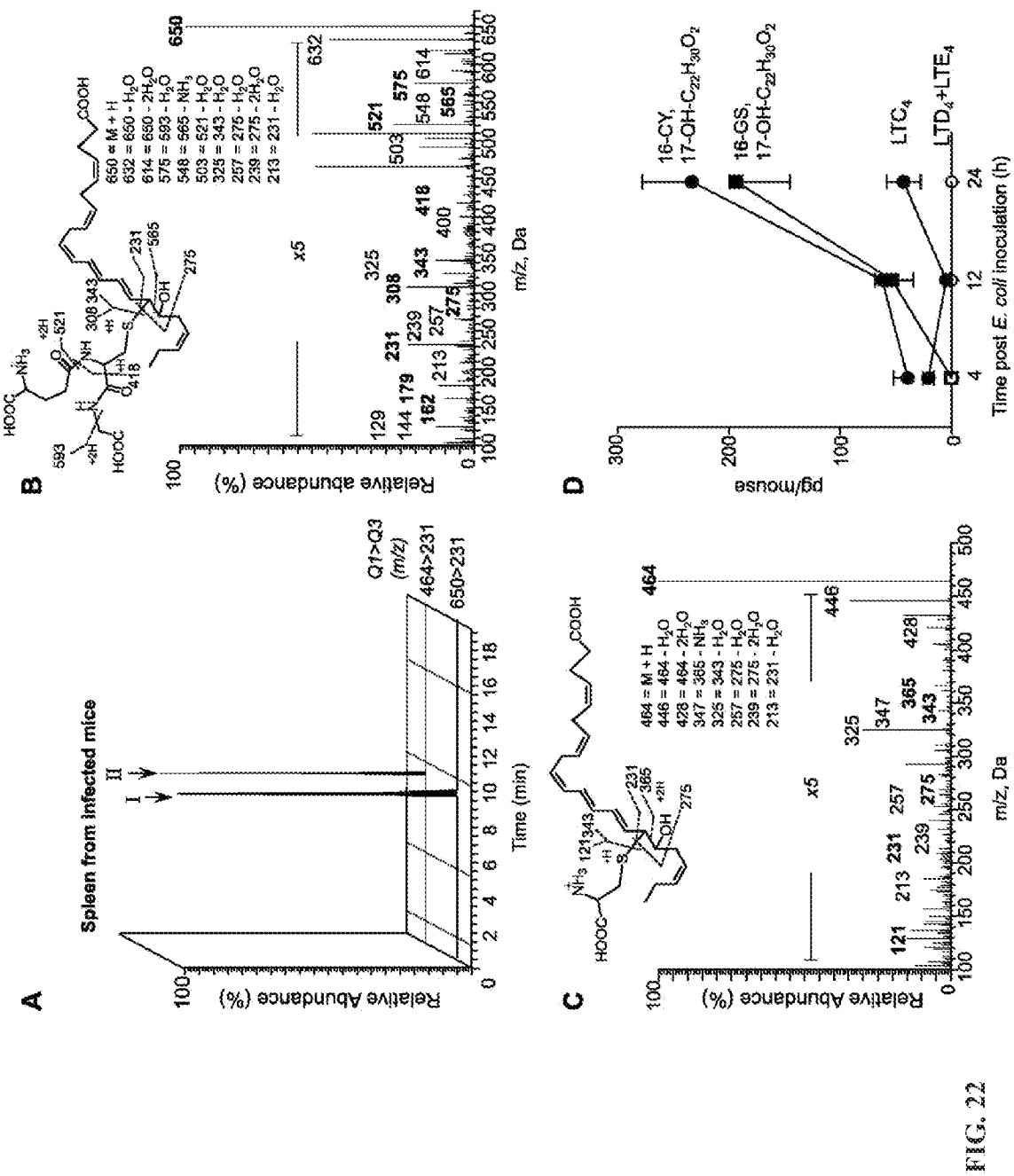

FIG. 22: In E. coli-infected mouse spleens, identification of novel sulfido-conjugates. Mice were inoculated with E. coli ($1 \times 10^5$ CFU/mouse) and spleens harvested. Products were extracted using C18 solid-phase columns and investigated by LC-MS-MS (see Materials and Methods). A) MRM chromatograms for the identified sulfido-conjugated products. B and C) MS-MS spectra employed for the identification of (B) 16-glutathionyl, 17-hydroxy-4Z,7Z,10,12,14,19Z-docosahexaenoic acid (I) and (C) 16-cysteinyl, 17-hydroxy-4Z,7Z,10,12,14,19Z-docosahexaenoic acid (II). D) Quantification of sulfido-confugated mediators in mouse spleen during self-resolving infections (16-GS,17-OH, $C_{22}H_{30}O_2$=16-glutathionyl, 17-hydroxy-4Z,7Z,10,12,14, 19Z-docosahexaenoic acid; 16-CY,17-OH,$C_{22}H_{30}O_2$=16-cysteinyl, 17-hydroxy-4Z,7Z,10,12,14,19Z-docosahexaenoic acid). Results for (A-C) are representative of n=9 mice. Results for (D) are the mean±SEM (n=3 mice per time interval).

Figure 23:
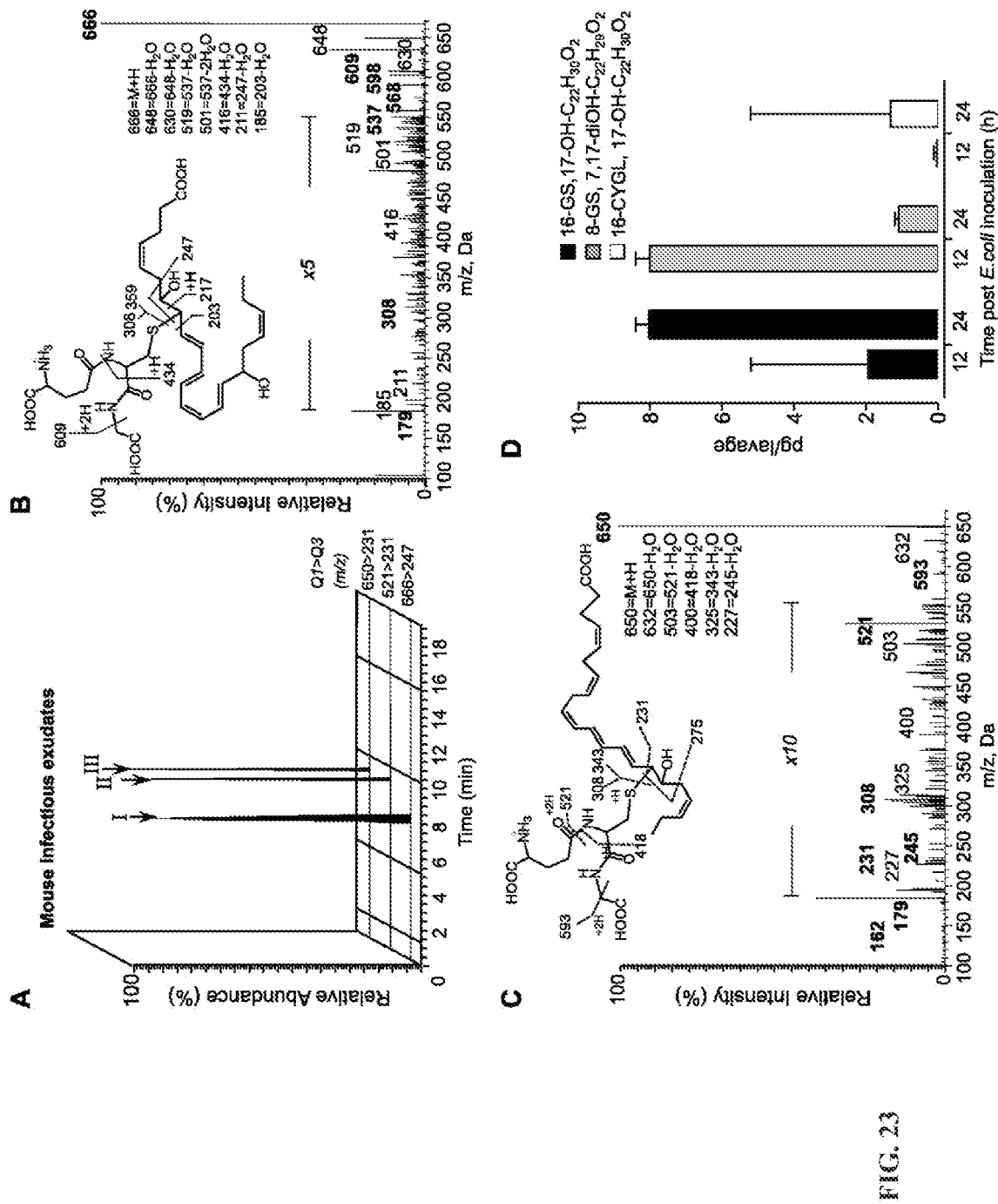

FIG. 23: E. coli-infected mouse exudates gave novel sulfido-conjugates. Mice were inoculated with E. coli ($1 \times 10^5$ CFU/mouse) and exudates collected 12 or 24 h later. Products were extracted using C18 solid-phase columns and investigated by LC-MS-MS (see Materials and Methods). A) MRM chromatograms for the identified sulfido-conjugated products. B and C) MS-MS spectra employed for the identification of (B) 8-glutathionyl, 7,17-dihydroxy-4Z,9,11, 13Z,15E,19Z-docosahexaenoic acid and (C)16-glutathionyl, 17-hydroxy-4Z,7Z,10,12,14,19Z-docosahexaenoic acid. D) Quantification of sulfido-conjugated mediators in mouse exudates during self-resolving infections (16-GS,17-OH, $C_{22}H_{30}O_2$=16-glutathionyl, 17-hydroxy-4Z,7Z,10,12,14, 19Z-docosahexaenoic acid; 8-GS, 7,17-diOH,$C_{22}H_{29}O_2$=8-glutathionyl, 7,17-dihydroxy-4Z,9,11,13Z,15E,19Z-docosahexaenoic acid; 16-CYGL,17-OH,$C_{22}H_{30}O_2$=16-cysteinylglycinyl, 7-hydroxy-4Z,7Z,10,12,14,19Z-docosahexaenoic acid). Results for (A-C) are representative of n=18 mice. Results for (D) are the mean±SEM (n=6 mice per interval). Lavage volume=5 ml each mouse.

Figure 24:
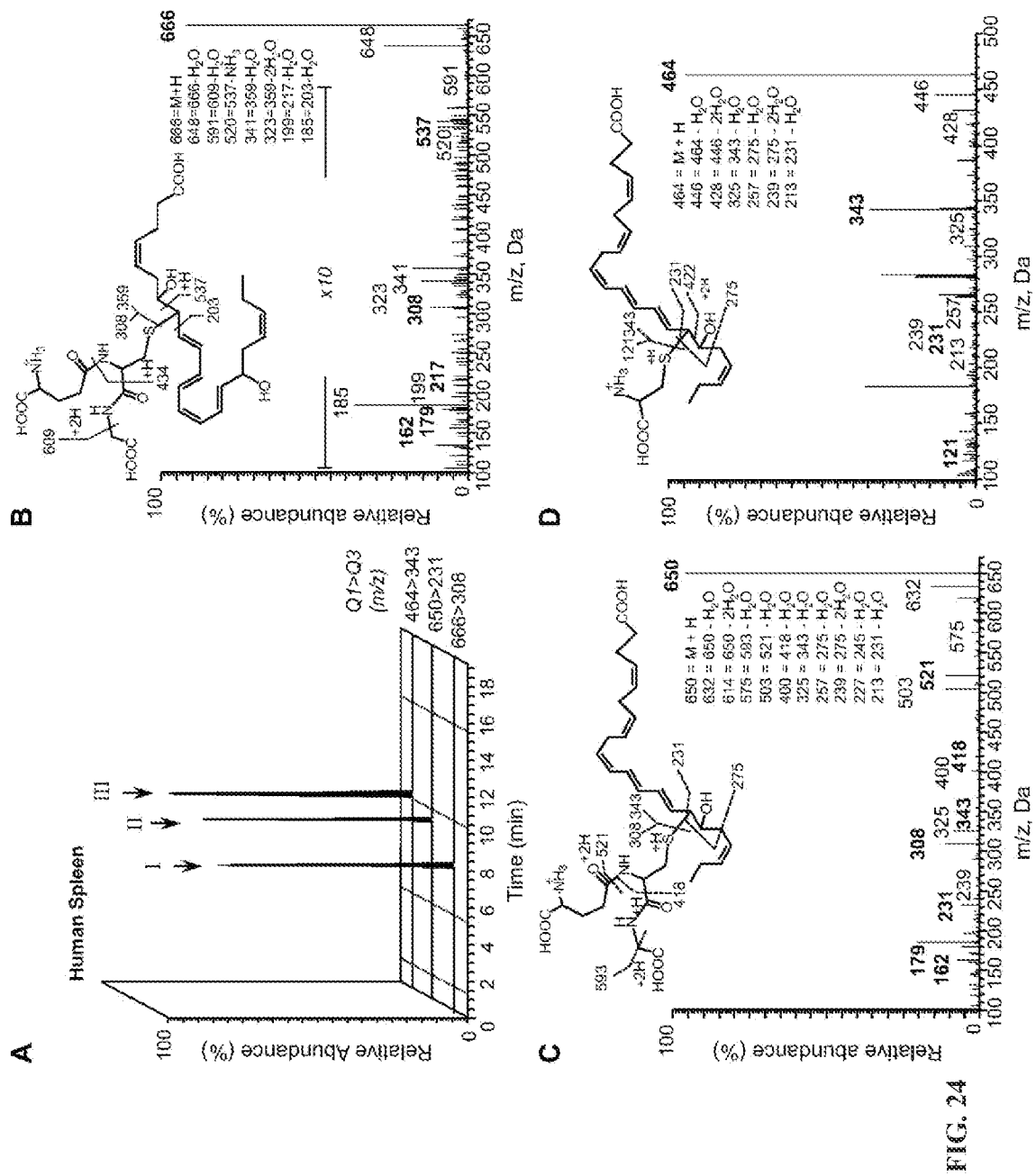

FIG. 24: Human spleen identification of novel sulfido-conjugates. Products from human spleens were extracted using C18 solid-phase columns and investigated by LC-MS-MS. A) MRM chromatograms for the identified sulfido-conjugated products. B-D) MS-MS spectra employed for the identification of (B) 8-glutathionyl, 7,17-dihydroxy-4Z,9, 11,13Z,15E,19Z-docosahexaenoic acid, (C) 16-glutathionyl, 17-hydroxy-4Z,7Z,10,12,14,19Z-docosahexaenoic acid, and (D) 16-cysteinyl,17-hydroxy-4Z,7Z,10,12,14,19Z-docosahexaenoic acid. Results are representative of n=3 human spleens.

Figure 25:
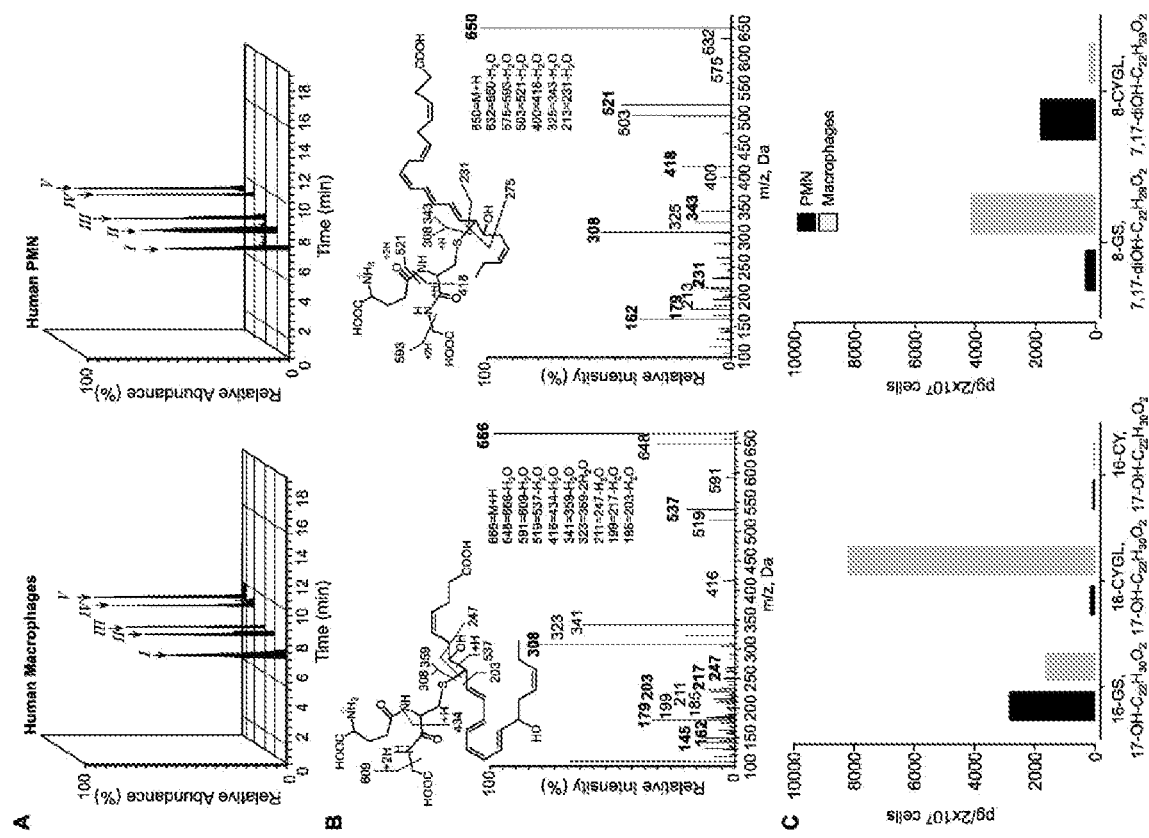

FIG. 25: 17 lipoxygenation of DHA is precursor to novel sulfido-conjugates with human phagocytes. Human macrophages and neutrophils were incubated 30 min at 37° C. with 1 μg 17-HpD plus 100 ng zymosan. A) Representative MRM chromatograms for each of the identified 17-series sulfido-conjugates in human macrophages (left panel) and PMN (right panel). B) Representative MS-MS spectra used for the identification of 8-glutathionyl, 7,17-dihydroxy-4Z,9,11, 13Z,15E,19Z-docosahexaenoic acid (left panel) and 16-glutathionyl, 17-hydroxy-4Z,7Z,10,12,14,19Z-docosahexaenoic acid (right panel). C) Quantification of identified sulfido-conjugates, 8-GS, 7,17-diOH-$C_{22}H_{29}O_2$=8-glutathionyl, 7,17-dihydroxy-4Z,9,11,13Z,15E,19Z-docosahexaenoic acid; 8-CYGL, 7,17-diOH-$C_{22}H_{29}O_2$=8-cysteinylglycinyl, 7,17-dihydroxy-4Z,9,11,13Z,15E,19Z-docosahexaenoic acid; 16-GS,17-OH,$C_{22}H_{30}O_2$=16-glutathionyl, 17-hydroxy-4Z,7Z,10,12,14,19Z-docosahexaenoic acid; 16-CYGL,17-OH,$C_{22}H_{30}O_2$=16-cysteinylglycinyl, 17-hydroxy-4Z,7Z,10,12,14,19Z-docosahexaenoic acid; 16-CY, 17-OH,$C_{22}H_{30}O_2$=16-cysteinyl, 17-hydroxy-4Z,7Z,10,12, 14,19Z-docosahexaenoic acid. Results for (A) and (B) are representative of n=3 healthy donors for each cell type. Results for (C) are the mean (n=3 healthy donors for each cell type).

Figure 26:
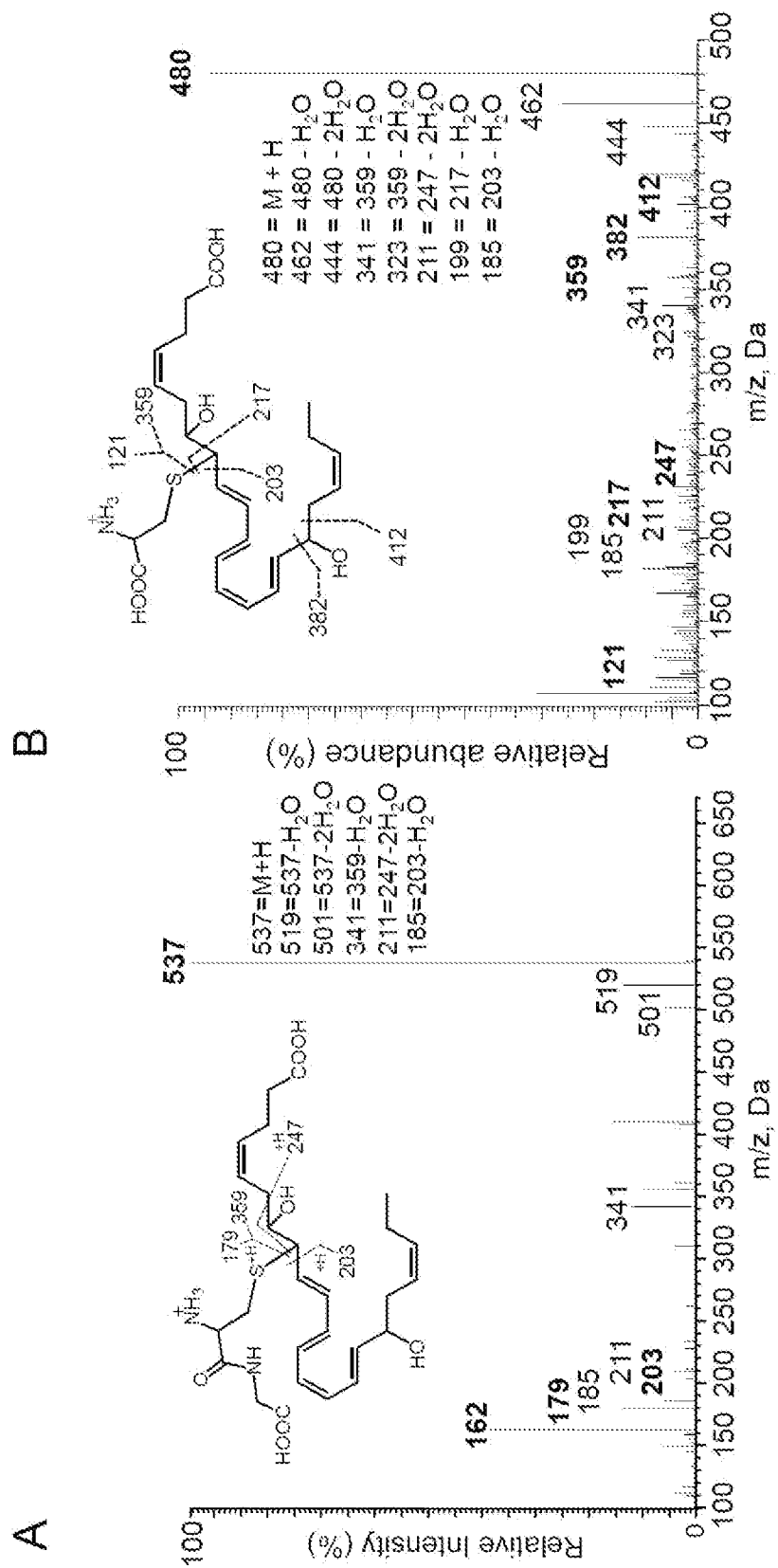

FIG. 26: Characteristic MS-MS spectra for the identification of novel sulfido-conjugated mediators. MS-MS spectra employed in the identification of (A) 8-cysteinylglycinyl, 7,17-hydroxy-docosahexaenoic acid (B) 8-cysteinyl, 7,17-hydroxydocosahexaenoic acid. Results are representative of n=3 macrophage preparations.

Figure 27:
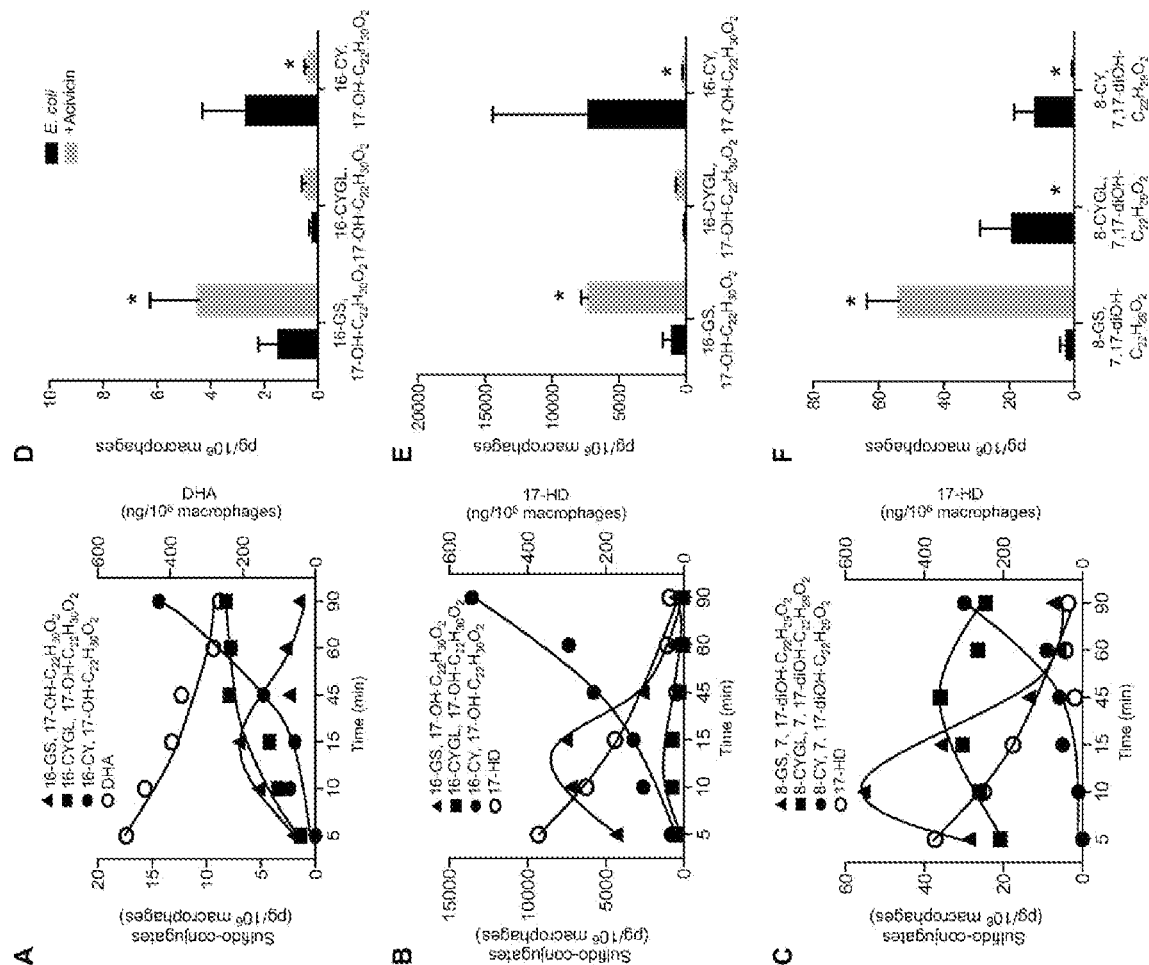

FIG. 27: Product-precursor relationships for the novel sulfido-conjugates. Human macrophages ($4.5 \times 10^7$ cells/ml) were incubated with (A) DHA [37° C. (pH 7.45)], (B and C) 17-HpD [37° C. (pH 7.45)], and E. coli ($1.5 \times 10^8$ CFU), and product levels were assessed using LC-MS-MS (see Materials and Methods for details). D-F) Human macrophages were incubated with or without GGT inhibitor [Acivicin; 2.5 mM at 37° C. (pH 7.45) for 30 min] then (D) DHA (E and F) 17-HpD [37° C. (pH 7.45)] and E. coli ($1.5 \times 10^8$ CFU). Incubations were quenched; precursor and product levels were assessed by LC-MS-MS. Results are the mean for n=3 macrophage preparations.*P<0.05 vs. vehicle macrophages.

Figure 28:
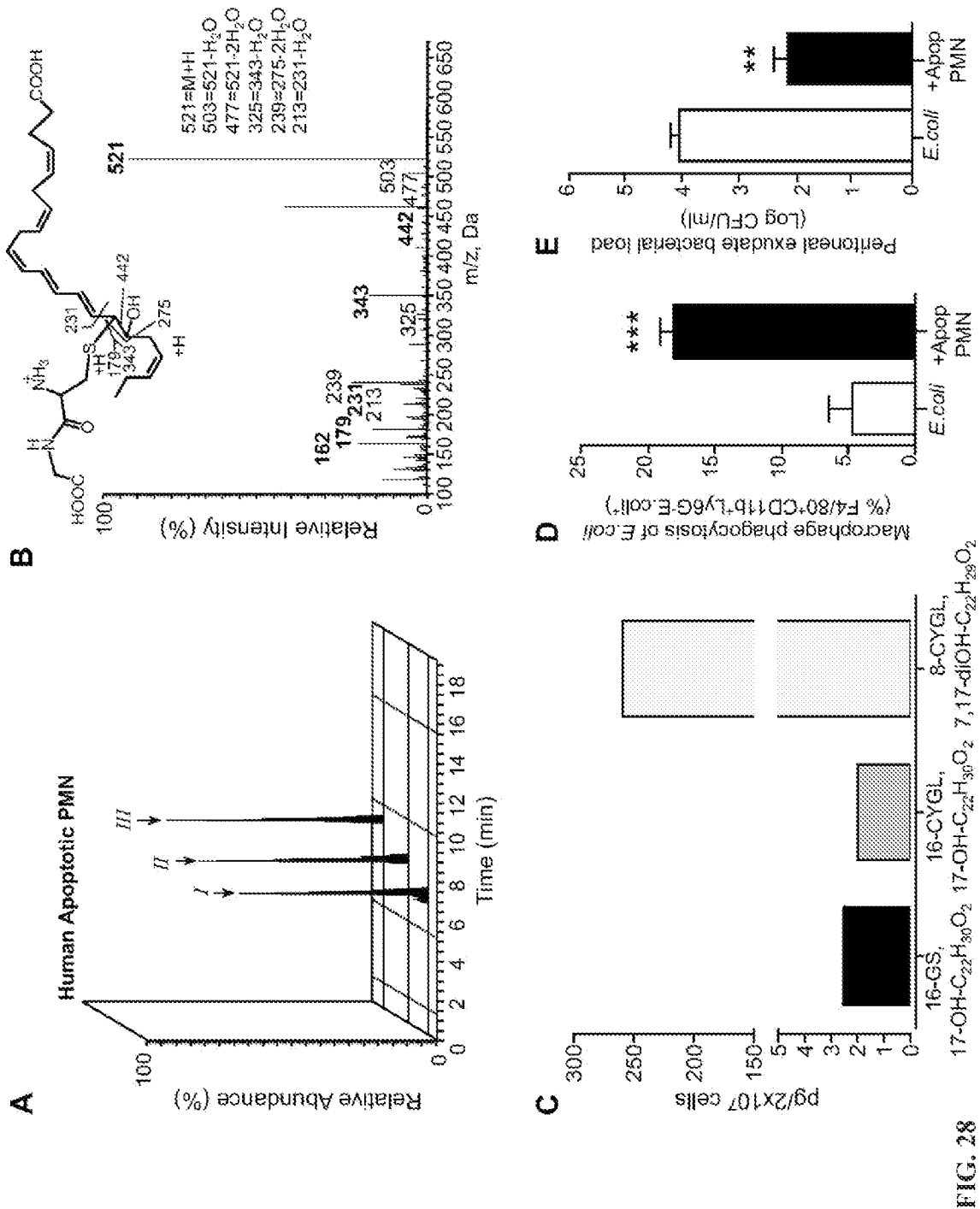

FIG. 28: Apoptotic human PMNs produce novel sulfido-conjugates from endogenous DHA and promote E. coli clearance during infection. Apoptotic neutrophil (see Materials and Methods for details) products were obtained and profiled by LC-MS-MS metabololipidomics. A) MRM chromatograms for identified products. B) Representative MS-MS spectrum employed for the identification of 16-cysteinylglycinyl, 17-hydroxy-4Z,7Z,10,12,14,19Z-docosahexaenoic acid. Results are representative of n=6 apoptotic PMN preparations. C) Quantification of identified sulfido-conjugates in apoptotic PMN preparations. 8-CYGL, 7,17-diOH-$C_{22}H_{29}O_2$=8-cysteinylglycinyl, 7,17-dihydroxy-4Z,9,11,13Z,15E,19Z-docosahexaenoic acid; 16-GS,17-OH, $C_{22}H_{30}O_2$=16-glutathionyl, 17-hydroxy-4Z,7Z,10,12,14,19Z-docosahexaenoic acid; 16-CYGL,17-OH,$C_{22}H_{30}O_2$=16-cysteinylglycinyl, 17-hydroxy-4Z,7Z,10,12,14,19Z-docosahexaenoic acid. Results are the mean for n=6 cell preparations. D and F) FYB mice were infected intraperitoneally with *E. coli* ($1\times10^5$ CFU/mouse). After 4 h, mice were administered saline (*E. coli*) apoptotic PMN (apop PMN, $15\times10^9$ cells per mouse, i.p.). Exudates were then collected. 12 h postinfection, D) Exudate macrophage phagocytosis of *E. coli* was assessed by flow cytometry. E) Bacterial titers present in the peritoneum were measured. Results for (A) and (B) are representative of n=3 neutrophil preparations. Results for (C) are the mean±SEM (n=3 mice per group). *$P\leq0.01$ and ***$P\leq0.001$ vs. *E. coli* mice.

Figure 29:
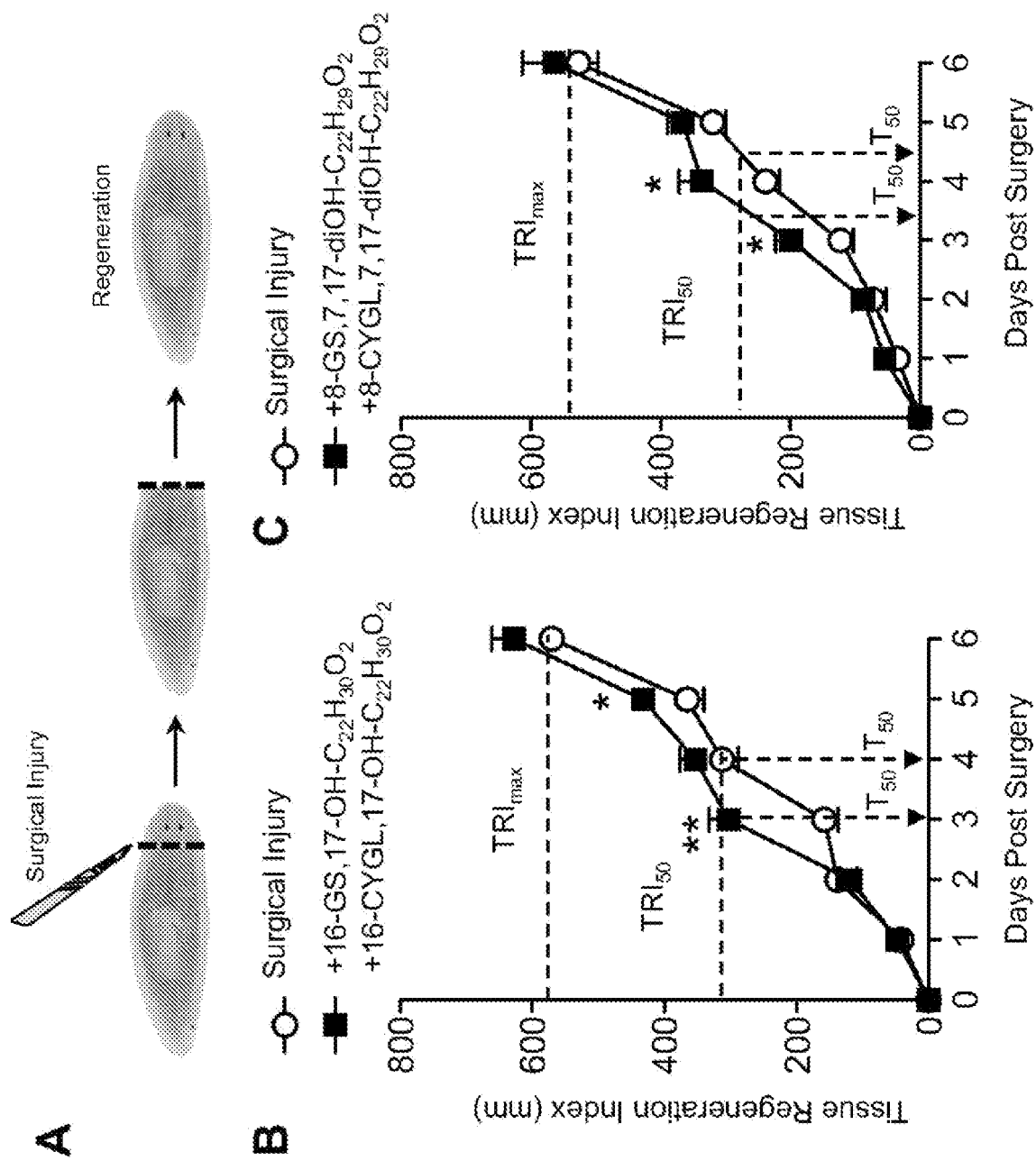

FIG. 29: Novel sulfido-conjugates accelerate tissue regeneration in planaria. A-C) Planaria were surgically injured, then kept in water containing (B) 16-glutathionyl, :17-hydroxy-4Z,7Z,10,12,14,19Z-docosahexaenoic acid plus 16-cysteinylglycinyl, 17-hydroxy-4Z,7Z,10,12,14,19Z-docosahexaenoic acid (50 nM; each), (C) 8-glutathionyl, 7,17-dihydroxy-4Z,9,11,13Z,15E,19Z-docosahexaenoic acid plus 8-cysteinylglycinyl, 7,17-dihydroxy-4Z,9,11,13Z,15E,19Z-docosahexaenoic acid (50 nM; each), or vehicle (water containing 0.01% EtOH), and tissue regeneration was assessed (see Materials and Methods for details). $TRI_{50}$, time to 50% regeneration. Results are the mean±SEM (n=4 planaria per group). *$P\leq0.05$ and **$P\leq0.01$ vs. respective surgical injury group.

Figure 30:
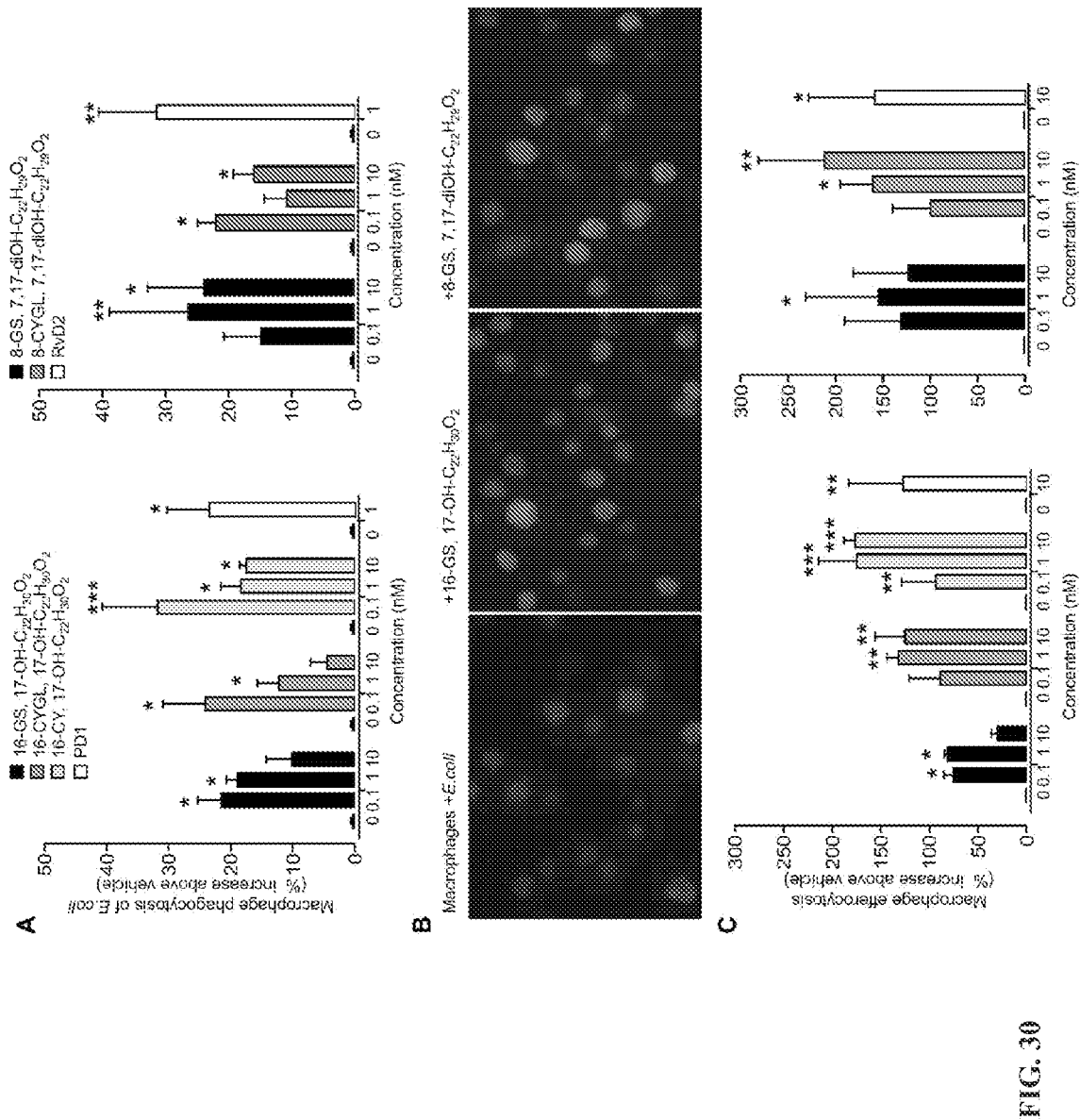

FIG. 30: 17-series sulfido-conjugates display potent anti-inflammatory and proresolving actions with human macrophages. A) Human macrophages ($5\times10^4$ cells per well) were incubated with the indicated concentrations of novel sulfido-conjugated mediators [15 min at 37° C. (pH 7.45)] before the addition of fluorescently labeled bacteria ($2.5\times10^6$ cells per well for 40 min at 37° C.). Noriphagocytosed cells were washed, extracellular fluorescence was quenched, and phagocytosis assessed using a fluorescence plate reader. B) Human macrophages ($5\times10^4$ cells per well) were incubated with a pH-sensitive fluorophore (30 min at 37° C.), then incubated with 10 nM sulfido-conjugated mediators [15 min. at 37° C. (pH 7.45)] prior to addition of bacteria ($2.5\times10^6$ cells per well for 60 min at 37° C.), and assessment of fluorescence was performed using a BZ9000 microscope equipped with a ×20 objective. C) Human macrophages ($5\times10^4$ cells per well) were incubated with the indicated concentrations of the novel sulfido-conjugated products for 10 min at 37° C. Fluorescently labeled apoptotic PMNs ($1.5\times10^5$ W cells per well) were then added (40 min at 37° C.), and efferocytosis was measured using a fluorescent plate reader. Results for (B) are representative of n=3 macrophage preparations. Results for (A) and (C) are the mean±SEM (n=3 macrophage preparations). *$P\leq0.05$, $P\leq0.01$, and *$P\leq0.001$ vs. vehicle incubated macrophages.

Figure 31:
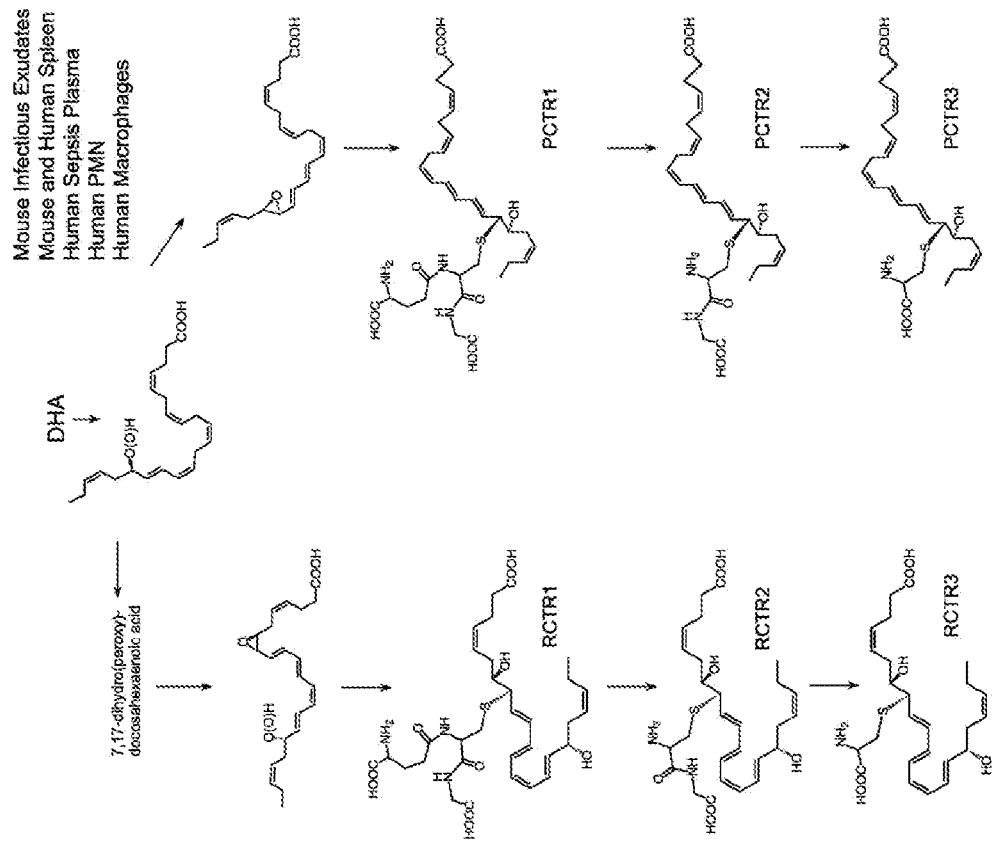

FIG. 31: Proposed biosynthesis of sulfido-protectins and sulfido-resolvins. Structures and pathways are depicted in likely stereochemistry based, on biosynthetic evidence (see main text for details). Their stereochemistries as shown are tentative. PCTR1, 16-glutathionyl, 17-hydroxy-4Z,7Z,10, 12,14,19Z-docosahexaenoic acid; PCTR2,16-cysteinylglycinyl, 17-hydroxy-4Z,7Z,10,12,14,19Z-docosahexaenoic acid; PCTR3, 16-cysteinyl, 17-hydroxy-4Z,7Z,10,12,14,19Z-docosahexaenoic acid; RCTR1, 8-glutathionyl, 7,17-hydroxy-4Z,9,11,13Z,15E,19Z-docosahexaenoic acid; RCTR2, 8-cysteinylglycinyl, 7,17-hydroxy-4Z,9,11,13Z,15E,19Z-docosahexaenoic acid; RCTR3, 8-cysteinyl, 7,17-hydroxy-4Z,9,11,13Z,15E,19Z-docosahexaenoic acid.

Figure 32:
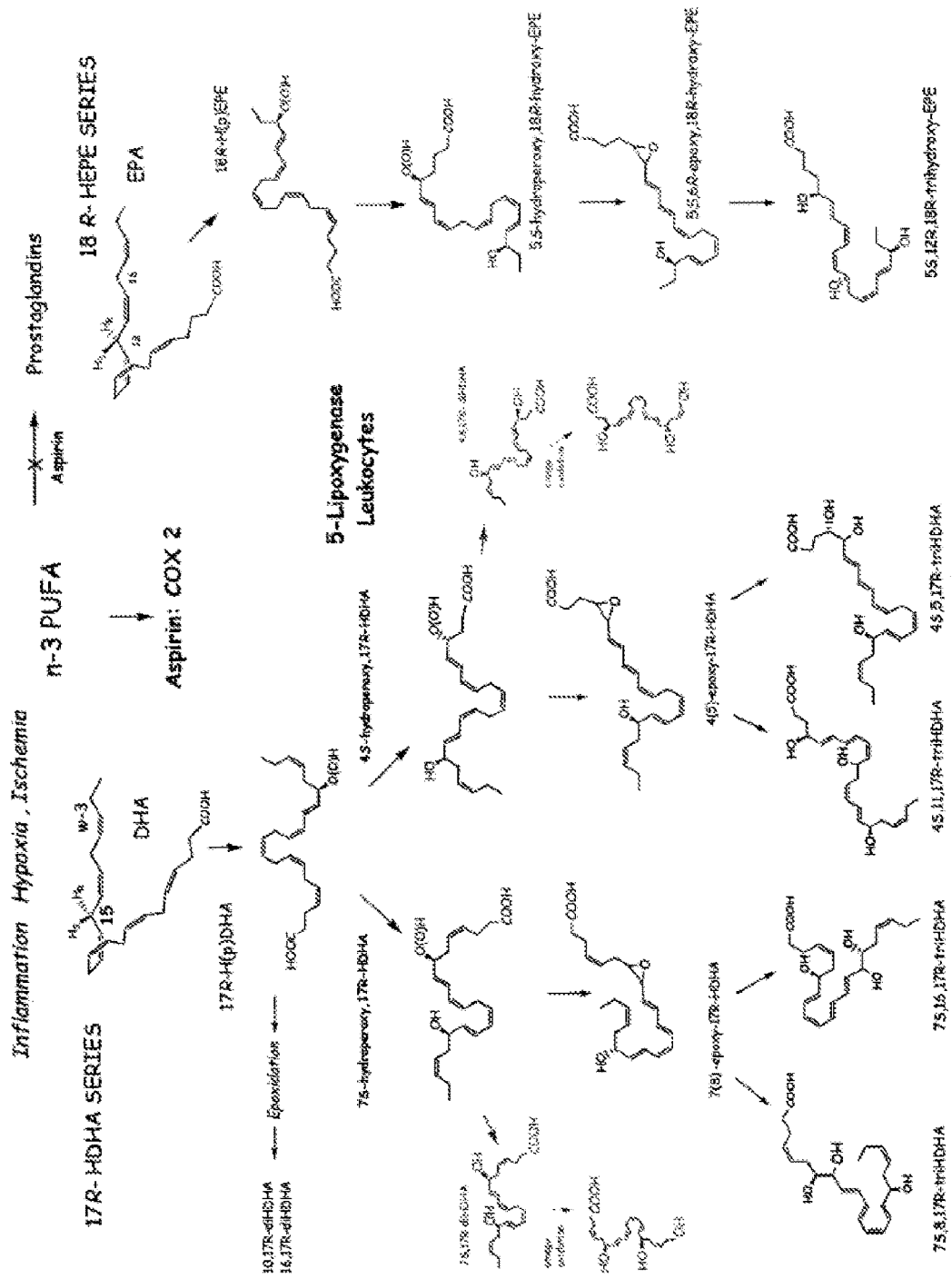

FIG. 32: Illustrates various metabolites of docosahexaenoic acid and eicosapentaenoic acid in the D-series Resolvin and E-Series Resolvin pathways including various epoxides formed therein.

Figure 33:
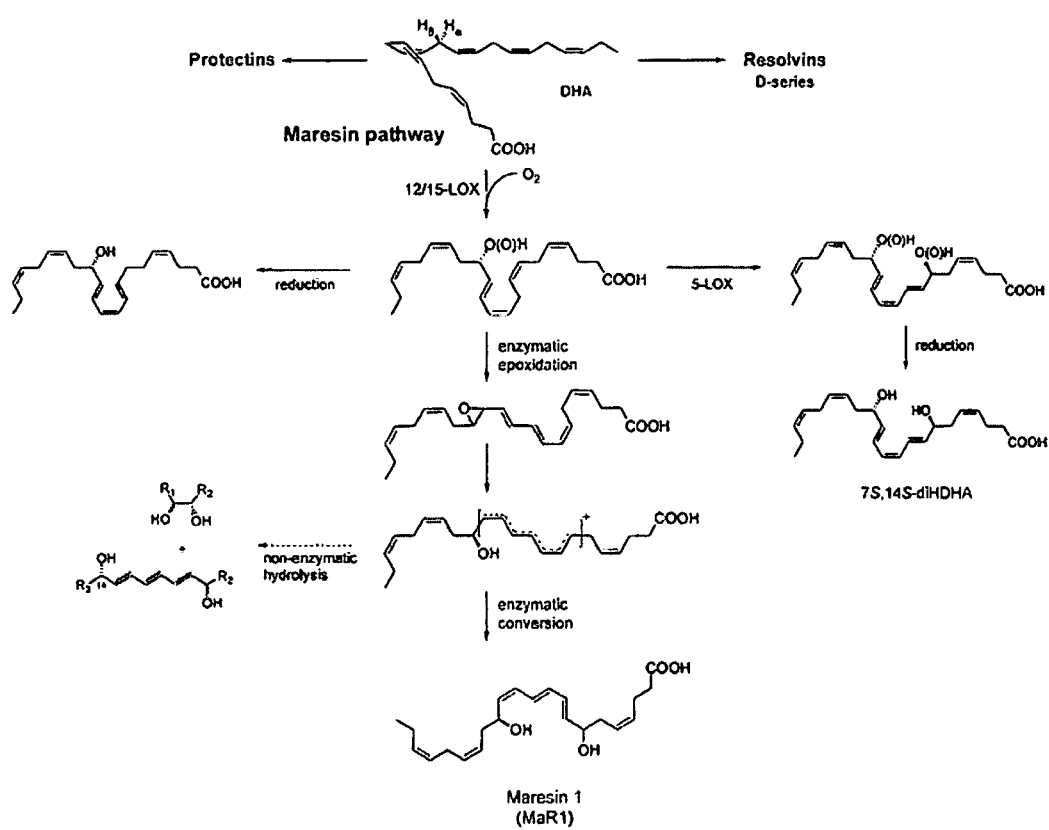

FIG. 33: Illustrates various metabolites in maresin biosynthesis pathway including the formation of epoxides.

Figure 34:
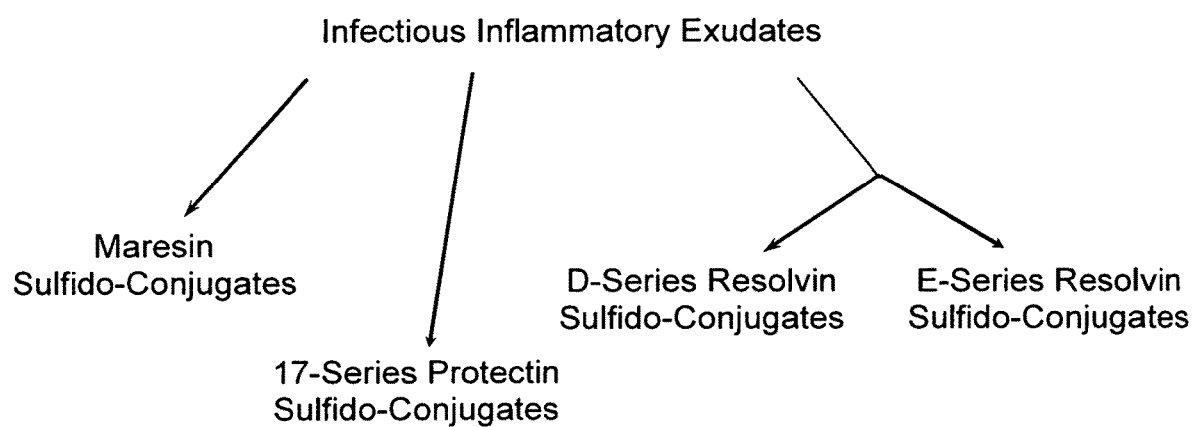

FIG. 34: Illustrates various families of sulfido-conjugates arising from infectious inflammatory exudates.

DETAILED DESCRIPTION OF THE EXEMPLARY EMBODIMENTS

Upon infection and inflammation, tissue repair and regeneration are essential in reestablishing function. Here the inventors identified potent molecules present in self-limited infectious murine exudates, regenerating planaria, human milk as well as macrophages that stimulated tissue regeneration in planaria and are pro-resolving. The compounds gave UV chromophores characteristic of a conjugated triene double bond system coupled to an auxochrome allylic to the triene. Further elucidation of the compounds reveals that they have an oxylipin backbone conjugated to a peptide moiety via the auxochrome. In some embodiments, the oxylipin backbone belongs to the maresin series, the protectin series, the resolvin series (D or E) or the lipoxins series. In some cases the auxochrome is sulfur. However, the auxochrome may be NH, $CH_2$ or O.

Local mediators orchestrate the host response to both sterile and infectious challenge and resolution. Recent evidence demonstrates that maresin sulfido-conjugates actively resolve acute inflammation and promote tissue regeneration. In this disclosure, reported are self-limited infectious exudates for novel bioactive chemical signals in tissue regeneration and resolution. By use of spleens from *Escherichia coli* infected mice, self-resolving infectious exudates, human spleens, and blood from patients with sepsis, the inventors identified further new families of potent molecules.

Characterization of their physical properties and isotope tracking indicated particular bioactive structures containing docosahexaenoic acid and sulfido-conjugated (SC) triene double bonds that proved to be 13-glutathionyl, 14-hydroxy-docosahexaenoic acid (SCI) and 13-cysteinylglycinyl, 14-hydroxy-docosahexaenoic acid (SCII). These molecules rescued *E. coli* infection-mediated delay in tissue regeneration in planaria, improving regeneration intervals from ~4.2 to ~3.7 days. Administration of SC protected mice from second organ reflow injury, promoting repair via limiting neutrophil infiltration, upregulating Ki67 and Roof plate-specific spondin 3. At nanomolar potencies these conjugates also resolved *E. coli* infections by limiting neutrophil infiltration, stimulating bacteria phagocytosis and clearance as well as efferocytosis of apoptotic cells. Together, these findings identify previously undescribed, conserved chemical signals, both in the 14-series and 17-series DHA derivatives and pathways in planaria, mice and human tissues that enhance host responses to contain infections, stimulate resolution of inflammation and promote the restoration of function.

Characterization of the physical properties and isotope tracking of the spleen and blood derived mediators demonstrated that the bioactive structures contained a docosahexaenoate backbone and sulfido-conjugated triene or tetraene double-bond systems. Activated human phagocytes converted 17-hydro(peroxy)-4Z,7Z,10Z,13Z,15E,19Z-docosahexaenoic acid to these bioactive molecules. Regeneration of injured planaria was accelerated with nanomolar amounts of 16-glutathionyl, 17-hydroxy-4Z,7Z,10,12,14, 19Z-docosahexaenoic acid and 16-cysteinylglycinyl, 17-hydroxy-4Z,7Z,10,12,14,19Z-docosahexaenoic acid (Protectin sulfido-conjugates) or 8-glutathionyl, 7,17-dihydroxy-4Z,9, 11,13Z,15E,19Z-docosahexaenoic acid and 8-cysteinylglycinyl, 7,17-dihydroxy-4Z,9,11,13Z,15E,19Z-docosahexaenoic acid (Resolvin sulfido-conjugates). Each protectin and resolvin sulfido-conjugate dose dependently (0.1-10 nM) stimulated human macrophage bacterial phagocytosis, phagolysosomal acidification, and efferocytosis. Together, these results identify 2 novel pathways and provide evidence for structural elucidation of new resolution moduli. These resolvin and protectin conjugates identified in mice and human infected tissues control host responses promoting catabasis.

Abbreviations used throughout the specification:

7S,14S-diHDHA (double dioxygenation), 7S,14S-dihydroxydocosa-4Z,8E,10Z,12E,16Z,19Z-hexaenoic acid;

14S-HDHA, 14S-hydroxydocosa-4Z,7Z,10Z,12E,16Z, 19Z-hexaenoic acid;

14S-HpDHA, 14S-hydroperoxydocosa-4Z,7Z,10Z,12E, 16Z,19Z-hexaenoic acid;

17S-HDHA, 17S-hydroxydocosa-4Z,7Z10Z,13Z,15E, 19Z-hexaenoic acid;

17-HpD, 17S-hydro(peroxy)-4Z,7Z,10Z,13Z,15E,19Zdocosahexaenoic acid;

17-HD, 17S-hydroxy-4Z,7Z,10Z,13Z,15E,19Zdocosahexaenoic acid;

AA, arachidonic acid;
CFU, colony forming unit;
EPA, eicosapentaenoic acid;
EFA, essential fatty acid;
DHA, 4Z, 7Z,10Z,13Z, 16Z,19Z-docosahexaenoic acid;
DPA, docosapentaenoic acid;
DTA, docosatetraenoic acid;
GC-MS, gas chromatography-mass spectrometry;
GGT, γ-glutamyl transferase;
HpD, hydro(peroxy)-docosahexaenoic acid;
LC/MS/MS, liquid chromatography-tandem mass spectrometry;
LM, lipid mediator;
LT, leukotrienen;
LOX, lipoxygenase;
MaR, Maresin, macrophage mediator in resolving inflammation;
MaR1, Maresin 1 (7R,14S-dihydroxy-docosa-4Z,8E, 10E12Z,16Z,19Zhexaenoic acid);
MCTR1, 13-glutathionyl, 14-hydroxy-docosahexaenoic acid;
MCTR2, 13-cysteinylglycinyl, 14-hydroxy-docosahexaenoic acid;
MCTR3, 13-cysteinyl, 14-hydroxy-docosahexaenoic acid;
MRM, multiple reaction monitoring;
MS, mass spectrometry; m/z,mass-to-charge ratio;
PCTR, protectin conjugate in tissue regeneration;
PCTR1, 16-glutathionyl, 17-hydroxy-docosahexaenoic acid;
PCTR2, 16-cysteinylglycinyl, 17-hydroxy-docosahexaenoic acid;
PCTR3, 16-cysteinyl,17-hydroxy-docosahexaenoic acid;
PD1, Protectin (D1) (10R, 17S-dihydroxy-docosa-4Z,7Z, 11E,13E,15Z, 19Zhexaenoic acid);
PG, prostaglandin;
PMN, polymorphonucleameutrophil;
RCTR, resolvin conjugate in tissue regeneration;
RCTR1, 8-glutathionyl, 7,17-hydroxy-docosahexaenoic acid;
RCTR2, 8-cysteinylglycinyl, 7,17-hydroxy-docosahexaenoic acid;
RCTR3, 8-cysteinyl, 7,17-hydroxy-docosahexaenoic acid;
RvD2, resolvin D2 (7S,16R,17S-trihydroxydocosa-4Z, 8E,10Z,12E,14E,19Z-hexaenoic acid);
RvE1, resolvin E1 (5S,12R,18R-trihydroxy-eicosa-6Z, 8E,10E,14Z,16E-pentaenoic acid);
SPM, specialized proresolving mediator;
T50, time to 50% regeneration;
TR, retention time;
TRI, tissue regeneration index;
TRImax, maximum tissue regeneration
MΦ, macrophage;
MCTR, maresin conjugates in tissue regeneration;
PD1, Protectin D1, 10R,17S-trihydroxydocosa-4Z,7Z, 11E,13E,15Z,19Z-hexaenoic acid;
$PGE_2$, prostaglandin $E_2$;
PMN, polymorphonuclear neutrophils;
Rv, resolvin;
RvD1, Resolvin D1, 7S,8R,17S trihydroxydocosa-4Z,9E, 11E,13Z,15E,19Z-hexaenoic acid;
RvE1, Resolvin E1, 5S,12R,18R-trihydroxyeicosa-6Z, 8E,10E,14Z,16E-pentaenoic acid;
SCI, sulfido-conjugated product I;
SCII, sulfido-conjugated product II;
SPM, specialized proresolving mediators In the specification and in the claims, the terms "including" and "comprising" are open-ended terms and should be interpreted to mean "including, but not limited to . . . ." These terms encompass the more restrictive terms "consisting essentially of" and "consisting of:".

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Compounds of the invention" refers to the bioactive peptide conjugates of DHA, n-3 DPA, DTA, AA and EPA analogues and compounds encompassed by generic formulae disclosed herein and includes any specific compounds within those formulae whose structure is disclosed herein.

The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention also include isotopically labeled compounds where one or more atoms have an atomic mass different from the atomic mass conventionally found in nature.

The compounds depicted throughout the specification contain ethylenically unsaturated sites. Where carbon carbon double bonds exist, the configurational chemistry can be either cis (E) or trans (Z) and the depictions throughout the specification are not meant to be limiting. The depictions are, in general, presented based upon the configurational chemistry of related DHA or EPA compounds, and although not to be limited by theory, are believed to possess similar configuration chemistry. The use of reflects this throughout the specification and claims so that both cis and trans isomers are contemplated. In certain embodiments the configuration of the ethylenic bond is known and is particularly described.

In one aspect of the invention, the compound(s) of the invention are substantially purified and/or isolated by techniques known in the art. The purity of the purified compounds is generally at least about 50%, preferably 90%, more preferably at least about 95%, and most preferably at least about 99% by weight.

Thus, the term "purified" as used herein does not require absolute purity; rather, it is intended as a relative term. For example, a purified DHA analogue can be one in which the subject DHA analogue is at a higher concentration than the analogue would be in its natural environment within an organism. For example, a DHA or EPA analogue of the invention can be considered purified if the analogue content in the preparation represents at least 10%, 50%, 60%, 70%, 80%, 85%, 90%, 92%, 95%, 98%, or 99% of the total analogue content of the preparation. Artisans will immediately appreciate that all the ranges and values within the explicitly stated ranges are contemplated.

"Auxochrome" as used herein refers to refers to an atom or molecule or moiety of a molecule that influences the intensity of absorption of the molecule.

"Biological activity" and its contextual equivalents "activity" and "bioactivity" means that a compound elicits a statistically valid effect in any one biological test assays. Preferably, the threshold for defining an "active" compound will be reproducible and statistically valid effects of at least 25% deviation from untreated control at concentrations at or lower than 1 µM.

"Biological test assay" means a specific experimental procedure. Non-limiting examples of biological test assays include: 1) ligand binding, either direct or indirect, to a purified target, subcellular fraction, intact cell, or cell or tissue extract; 2) metabolic protection with enhanced half-life when exposed to a purified target, subcellular fraction, intact cell, cell or tissue extract, or administered to intact organism by any route; 3) prevention, reversal, or amelioration of cell- and tissue-based functional responses recognized by skilled artisans to represent surrogates for anti-inflammatory action (e.g., altered cytokine production and release); and 4) prevention, reversal, or amelioration of symptoms and/or disease processes in animal models of inflammation and inflammatory disease.

"Conjugated" when used herein in its broadest sense such as "conjugated compounds" two or more joined compounds or moieties. The compounds can be joined by a bond such as by covalent bonds or non-covalent bonds including, ionic bonds, hydrogen bonds, van der Waals forces and the like. "Conjugated" may be used in a more specific sense as well, as in a "conjugated bond system" meaning a system of connected p-orbitals with delocalized electrons in compounds with alternating single and multiple bonds, which in general may lower the overall energy of the molecule and increase stability. Lone pairs, radicals or carbenium ions may be part of the system. The compound may be cyclic, acyclic, linear or mixed.

"Triene" as used herein means a conjugated bond system including three double bonds.

"Detectable label" means any chemical or biological modality which can be used to track, trace, localize, quantify, immobilize, purify, or identify compounds through appropriate means of detection known in the art. Non-limiting examples of detectable labels include fluorescence, phosphorescence, luminescence, radioactive or biospecific affinity capture labels.

"Derivative" as used herein means derived from. For example a DHA analogue may be derived from DHA. The derivative may be a natural metabolite or it may be a synthetic compound derived from a natural compound or the compound may be synthesized in toto.

"Electronegative group" is a chemical group that tends to acquire rather than lose electrons in its chemical interactions. Examples of electronegative groups include, but are not limited to, $-NO_2$, ammonium salts, sulfonyl groups, carbonyl groups, halogens, esters, carboxylic acids, nitriles, etc.

"In Situ" refers to and includes the terms "in vivo," "ex vivo" and "in vitro" as these terms are commonly recognized and understood by the skilled artisan. Moreover, the phrase "in situ" is employed herein in its broadest connotative and denotative context to identify an entity, cell, or tissue as found or in place, without regard to its source or origin, its condition or status or its duration or longevity at that location or position.

"Oxylipin" as used herein refers to an oxygenated fatty acid formed from a precursor by at least one step of dioxygen-dependent oxidation. Non-limiting examples of fatty acids that are substrates for oxylipin synthesis include, but are not limited to, docosapentaenoic acid (C22:5n-6) (DPAn-6) and its ω-3 isomer DPAn-3, docosatetraenoic acid (C-22:4n-6)(DTAn-6); docosahexaenoic acid (C-22:6n-3) (DHA); eicosapentaenoic acid (C20:5n-3)(EPA); and arachidonic acid (C20:4n-6), for example.

"Moiety" as used herein refers to specific groups of atoms or bonds within molecules that are responsible for the characteristic chemical reactions of those molecules.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) salts fanned when an basic proton is present in the parent compound such as acid addition salts, formed with inorganic acids such as hydrochloric acid, hydrobromic acid, sulfuric acid, nitric acid, phosphoric acid, and the like; or those formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethytacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton is present in the parent compound and either is replaced by a metal ion, e.g., an alkali metal ion, an alkaline earth ion, or an aluminum ion; or coordinates with an organic base such as ethanolamine, diethanolamine, triethanolamine, N-methylglucamine, triethylamine, propylamino, diazabicycloundecane and the like.

"Pharmaceutically acceptable vehicle" refers to a diluent, adjuvant,excipient or carrier with which a compound of the invention is administered.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

"Prodrug" refers to a derivative of a drug molecule that requires a transformation within the body to release the active drug. Prodrugs are frequently (though not necessarily) pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, imine, phosphonyl, phosphoryl or sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which contain different functional groups other than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2,sup.nd ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethane-sulfonyl ("SES"), trityl and substituted trityl groups, allyloxycarbonyl, 9-fluorenyhnethyloxycarbonyl ("FMOC"), nitro-veratryloxycarbonyl ("NVOC") and the like. Representative hydroxy protecting groups include, but are not limited to, those where the hydroxy group is either acylated (e.g., methyl and ethyl esters, acetate or propionate groups or glycol esters) or alkylated such as benzyl, and trityl ethers as well as alkyl ethers, tetrahydropyranyl ethers, trialkylsilyl ethers (e.g., TMS or TIPPS groups) and allyl ethers.

"Subject" means living organisms susceptible to conditions or diseases caused or contributed to by inflammation, inflammatory responses, vasoconstriction and myeloid suppression. Examples of subjects include humans, dogs, cats, cows, goats and mice. The term subject is further intended to include transgenic species such as, for example, transgenic mice.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan 1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6)alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan- 1-yl, etc.; butanyls such as butan-1-yl, butan-2-yl (sec-butyl), 2-methyl-propan-1-yl(isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethers-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,2-diyl, buta-1,3-dien-1,3-diyl, buta-1,3-dien-1,4-diyl, but-1,3-dien-1,4-diyl, cyclobut-1-en-1,2-diyl, cyclobuta-1-en-1,3-diyl, cyclobut-2-en-1,2-diyl, cyclobuta-1,3-dien-1,2-diyl, cyclobuta-1,3-dien-1,3-dien-1,3-diyl, but-1-yn-1,3-diyl,but-1-yn-1,4-diyl, buta-1,3-diyl-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldlyl group is (C1-C6)alkyldiyl. Also preferred are saturated acyclic alkanyldiyl groups in which the radical centers are at the terminal carbons, e.g., methandiyl (methano); ethan-1,2-diyl(ethano); propan-1,3-diyl (propano); butan-1,4-diyl (butano); and the like (also referred to as alkylenos, defined infra).

"Alkdiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkdiyl groups include, but are not limited to methandiyl; ethyldiyls such as ethan-1,1-diyl, ethan-1,2-diyl, ethen-1,1-diyl, ether-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl-, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In a preferred embodiment, the alkdiyl group is (C1-C6) alkdiyl. Also preferred are saturated acyclic alkanyldiyl groups in which the radical centers are at the terminal carbons, e.g., methandiyl (methano); ethan-1,2-diyl(ethano); propan-1,3-diyl (propano); butan-1,4-diyl(butano); and the like (also referred to as alkylenes, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenes such as ethano, etheno, ethyno; propylenos such as propano, prop[1]eno, propa[1,2]dieno, prop[1]yno, etc,; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," "Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)

NR'—, —S(O)₂NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl tetrahydrofuran-2-yl, tetrahydrofuran-3-yl, etc.), piperidinyl (e.g., piperidin-1-yl, piperidin-2-yl, etc.), morphotinyl (e.g., morpholin-3-yl, morpholin-4-yl, etc), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)₂—, —S(O)NR'—, —S(O)₂NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthatene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly (preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)₂, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazote, benzoxaxine, benzoxazole, benzoxazoline, carbazole, beta-carbotine, chromane, chromene, cinnoline, furan, imidazole, indazole, indole, indoline, indolizine, isobenzofuran, isochromene, isoindole, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroatyl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripyridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc, up to perhaloalkyls. For example, the expression "(C1-C2)haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional welt-recognized substituent groups. As examples, "alkyloxy" or "alkoxy" refers to a group of the formula —OR", "alkylamine" refers to a group of the formula —"NHR" and "dialkylamine" refers to a group of the formula —NR"R'", where each "R" is independently an alkyl. As another example, "haloalkoxy" or "haloalkyloxy" refers to a group of the formula "—OR'", where "R'" is a haloalkyl.

When the body is unable to contain infections this may lead to collateral organ damage resulting from unchecked innate immune responses. Here the inventors investigated the chemical signals produced by immune cells to expedite clearance of bacteria, promote organ repair and tissue regeneration. The inventors identified molecules produced during self-limited infections and in human milk that promote clearance of bacteria as well as accelerate tissue regeneration. In addition these molecules also protected organs from exuberant inflammatory responses, such as, ischemia/reperfusion injury, by limiting select white blood cell recruitment and upregulating the expression of proteins involved in tissue repair. Therefore these results identify new resolution moduli that regulate phagocytes to clear bacteria, activate the regeneration milieu.

Various exemplary embodiments of compounds Obtained as generally described above and methods according to this invention, will be understood more readily by reference to the following examples, which are provided by way of illustration and are not intended to be limiting of the invention in any fashion.

EXAMPLES

Statistics: All results are expressed as means±sem. Differences between groups were compared using Student's t test (2 groups), 1-way ANOVA (multiple groups) followed by post hoc Bonferroni test or 2-way ANOVA (multiple groups, multiple time points) followed by post hoc Bonferroni or Sidak tests. The criterion for statistical significance was $P<0.05$.

Example 1

Murine Peritonitis: Mouse experiments were conducted in accordance with guidelines from Harvard Medical Area Standing Committee on Animals (protocol no. 02570). Mice were inoculated with *E. coli* (serotype 06:K2:H1) as in (11) and peritoneal exudates were collected by lavaging the peritoneal cavity with 4 ml of PBS (without calcium and magnesium) at the indicated intervals. Leukocytes were enumerated by light microscopy using nuclear morphology staining with Turks solution and flow cytometry probing for CD11b-PerCP/Cy5.5 (eBioscience, clone: M1/70), F4/80-PE (eBioscience, BM8) and Ly6G-FITC (eBioscience, clone: 1A8) as in (11). For product isolation, 24 h peritoneal exudates were collected and 2 volumes of ice-cold methanol were added. Isolates were obtained as detailed in the lipid mediator metabotolipidomics section.

In select experiments 12 h after *E. coli* inoculation, mice were administered either 100 ng of SCI and SCII (50 ng/each per mouse) or vehicle (saline containing 0.1% ethanol (EtOH)) via i.p. injection. Peritoneal exudates were then collected and leukocyte counts determined as above. Assessment of leukocyte phagocytosis of *E. coli* in inflammatory exudates was conducted as in (11). Briefly cells were incubated with anti-CD11b-Per(T/Cy5.5 conjugated antibody; subsequently the cells were permeabilized using BD Cytofix/Cytoperm™ Fixation/Permeabilization Kit following manufacturer's instructions; cells were then incubated with a FITC conjugated anti-*E. coli* antibody (GTX40856; GeneTex) and phagocytosis assessed as mean fluorescence in the CD11b- positive cell population.

Resolution indices were calculated as in (11) where $\Psi_{max}$=the maximal PMN numbers in the exudates; $T_{max}$=the time point when PMN numbers reach maximum; $R_{50}$=50% of maximal PMN numbers; $T_{50}$=the time point when PMN numbers reduce to 50% of maximum; $R_i$ (resolution interval)=$T_{50}$-$T_{max}$, the time period when 50% PMN are lost from the exudates.

Mice were administered either $10^5$ (self resolving) or $10^7$ (delayed resolving) CFU *E. coli* and exudates harvested after 12 h or 24 h. These were then incubated with either DHA (Cayman Chemical) or $^{14}C$ labeled DHA (American Radiolabeled Chemicals Inc.; 1 µM, 37° C., pH 7.45). The incubations were then stopped with 2 volumes of ice-cold methanol and products extracted using SPE columns as detailed below. Radioactivity was measured using a scintillation counter and DHA-derived products assessed using LC-MS-MS and product ion scan targeting product ion with m/z 343 (See, FIG. 3B).

In determined experiments, mice were administered SC isolates from regenerating planaria i.p., obtained as described in the lipid mediator metabololipidomics and isolation of bioactive fractions section below, immediately prior to zymosan administration (i.p. 1 mg/mouse). After 4 h, peritoneal exudates were obtained, leukocytes enumerated as detailed above and eicosanoid levels assessed by lipid mediator metabololipidomics as described below.

Example 2

Ischemia Reperfusion: Mice were anesthetized by intraperitoneal (i.p.) injection of xylazine (80 mg/kg) and ketamine (10 mg/kg). To initiate hind-limb ischemia, tourniquets consisting of a rubber band were placed on each hind limb. Ten min prior to the initiation of reperfusion, Vehicle (saline containing 0.1% EtOH), SCI (50 ng) plus SCII (50 ng) or Resolvin D1 (500 ng) were administered by intravenous injection. At the end of reperfusion (3 h), mice were euthanized, blood collected via cardiac puncture and plasma isolated for lipid mediator metabololipidomics. Lungs were harvested, left lungs were frozen in liquid nitrogen and stored at −80° C. Right lungs were stored in 10% (v/v) buffered formalin and processed for histology and hematoxylin and eosin (H&E) staining by the Children's Hospital Boston Core Histology Facility, imaged using a Keyence BZ-9000 microscope and BZ II imaging software (Keyence) Expression of Ki67 and Roof plate-specific Spondin-3 (RSPO3) were assessed by immunofluorescence staining. Briefly, sections were deparafinized in xylene and rehydrated, then blocked in 10% horse serum and stained with either rat anti-mouse RSPON3 antibody (R&D Systems) for 1 h at room temperature and then with sheep anti-rat Alexa-594 conjugated antibody (BioLegend), or with rabbit anti-mouse antibody (Abeam) and then with donkey anti-rabbit Alexa-488 antibody (BioLegend). Slides were mounted in Vector Shield mounting solution with DAPI (Vector Labs) and immunofluorescence assessed using a Zeiss LSM 510 Meta confocal microscope. Images were processed using ImageJ software (National Institutes of Health) and Adobe Photoshop CS6 (Adobe Systems incorporated) software. Frozen lungs were gently dispersed, centrifuged, and tissue myeloperoxidase (MPO) levels were determined using mouse MPO ELISA (R&D Systems).

Example 3

Leukocyte phagocytosis: Macrophages were prepared from peripheral blood mononuclear cells (PBMC) purchased from Children's Hospital Blood Bank, Boston, and phagocytosis was assessed as in (11). Briefly, macrophages ($5 \times 10^4$ cells,/well) were incubated with SCI (10 pM-100 nM), SCII (10 pM-100 nM), MaR1 (10 pM-100 nM), or vehicle (0.1% EtOH in DPBS) for 15 min at 37° C., then fluorescent labeled apoptotic cells were added and cells incubated 45 min at 37° C. Extracellular fluorescence was quenched using Trypan blue (1:15 dilution) and phagocytosis assessed using an M3 SpectraMax plate reader. In select experiments, macrophages ($5 \times 10^4$ cells/well) or neutrophils ($1 \times 10^5$ cells/well) were obtained from human healthy volunteers' peripheral blood as in (11) in accordance with Partners Human Research Committee Protocol (#1999P001297), and incubated with $H_2DCFDA$ (5 µM, 30 min, 37° C.), then with SCI (10 pM-100 nM), SCI (10 pM-100 nM) or vehicle (0.1% EtOH in DPBS, 15 min, 37° C.) and *E. coli* (1:50 leukocytes to *E. coli,* 45 min, 37° C.) Intracellular reactive oxygen species were determined by measuring fluorescence using an M3 SpectraMax plate reader. To assess bacterial phagocytosis, macrophages ($5 \times 10^4$ cells/well) or neutrophils ($1 \times 10^5$ cells/well) were incubated with SCI (10 pM-100 nM), SCII (10 pM-100 nM) or vehicle (0.1% EtOH in DPBS, 15 min, 37° C.), then incubated with BacLight Green (Molecular Probes) labeled *E. coli* (1:50 leukocytes to *E. coli,* 45 min, 37° C.), Extracellular fluorescence was quenched using Trypan blue (1:15 dilution), and phagocytosis assessed using an M3 SpectraMax plate reader.

In determined experiments, human macrophages were incubated with SC isolates from regenerating planaria for 15 min at 37° C., then fluorescent labeled apoptotic cells were added and efferocytosis was assessed as detailed above.

Example 4

Whole mount in situ hybridization, real-time PCR and dsRNA synthesis: Regenerating blastemas were obtained from planaria after surgical injury and placed in Trizol (Ambion). RNA was isolated following manufacturer's instructions and cDNA was synthesized essentially as in (16) using random hexamers, Oligo(dt)$_{20}$ and Superscript III (Invitrogen), Relative quantitative analysis for each gene product was carried out using an ABI 7900ht fast real-time PCR machine (Applied Biosystems). DjGapdh—Forward: ACCACCAACTGTTTAGCTCCCTTA (SEQ ID NO. 1); Reverse: GATGGTCCATCAACAGTCTTTTGC (SEQ ID NO. 2). Djsfpr-A—Forward: TTGCTCTCTT-TACGCTCCGGT (SEQ ID NO. 3); Reverse: CGCAT-AGTTCCCTGCATGGT (SEQ ID NO. 4). Djndk—Forward: TCACAAACTCCACCGCAGTACTTT (SEQ ID NO. 5); Reverse: GGTATGGATTAGCATTATTGAAT-TGTG (SEQ ID NO. 6). DjmpkA—Forward: CACTGA-TATCTACTTCACGAAAGCCAG (SEQ ID NO. 7); Reverse: AAGGCATCCAGTTCATTTCCTAAAT (SEQ ID NO. 8). DfAdb-Ba—Forward: CGTAGGCAATACTTA-CATCACTAGACAAA (SEQ ID NO. 9); Reverse: TGTCTCTCCGACAAATGCAATTT (SEQ ID NO. 10). DjGst—Forward: TGTTGGCTGAAGAAGTGCAAG (SEQ ID NO. 11); Reverse: TTCACCCATAAGC-CAATGCT (SEQ ID NO. 12). The constitutively transcribed housekeeping gene, GAPDH, was employed to normalized target gene expression levels as in (16).

Two separate PCR products containing T7 promoter sequences on the 5'-ends of either sense or anti-sense strand DNA were used as templates to transcribe anti-sense and sense RNA using T7 RiboMAX™ Express RNAi. System (Promega) (DjGst with T7 promoter sequence—Forward: GGATCCTAATACGACTCACTATAGGAGTGGCAAT-CACCACCAAAT (SEQ ID NO. 13); Reverse: GGATCCTAATACGACTCACTATAGGAGTGGCAAT-CACCACCAAAT (SEQ ID NO. 14). DjGst Primers—Forward: GGCTCCTTTGTTAGGTTACTGGA (SEQ ID NO. 15); Reverse: AGTGGCAATCACCACCAAAT (SEQ ID NO. 16). These two complimentary single-stranded RNA (ssRNA) were mixed and incubated at 70° C. (10 min) then slowly cooled to room temperature (~20 min) to allow annealing of the dsRNA. The remaining template DNA and ssRNA were removed by treatment with DNase and RNase A (37° C., 30 min) essentially as in (28). The dsRNA was then precipitated (0.1 volume of 3 M sodium acetate, pH 5.2, and 1 volume of isopropanol) and further purified using MicroSpin G-25 Columns (GE Healthcare) to remove residual nucleotides.

PCR products containing T7 promoter sequences on the 5' end of the sense strand DNA were employed to produce in situ hybridization probes to DjGst using FISH Tag™ Kits (Invitrogen) following manufacturer's instructions. Planaria were treated with 2% hydrochloric acid (HCl) in 5/8 Holtfreter's solution for 5 min at 4° C. and fixed in 5/8 Holtfreter's solution containing 4% paraformaldehyde and 5% methanol for less than 2 h at 4° C. Planaria were then dehydrated and rehydrated, bleached and probes were hybridized as in (29).

Example 5

Planaria regeneration: Planaria (*Dugesia japonica*; Dj) were kept in water (Poland Spring) at 18° C. All animals were starved for at least 7 days prior to experiments. Tissue regeneration was assessed as in (12). Briefly, planaria were subject to head resection post-occularly (surgical Injury). The posterior portions of the planaria were then placed in spring water containing 0.01% EtOH, SPE-C isolate fraction 2 from resolving exudates or milk at the indicated dilutions, U0126 (Extracellular signal-regulated kinases (ERK) inhibitor; Cell Signaling Technology; 25 µM (16)), U0126 plus resolving exudates SPE-C isolates fraction 2, SCI (100 nM), SCII (100 nM), lipoxygenase inhibitor (baicalein, 10 µM) or lipoxygenase inhibitor plus SCI and SCII (100 nM). The extent of tissue regeneration during a 6-day period for *D. japonica* was determined using captured images of the regenerating blastemas at regular intervals (24 h). These images were analyzed using ImageJ software. A tissue regeneration index (TRI) was employed that took into consideration the size of the regenerated tissue total area (A) and the post-ocular width W of the animal, where TRI=A/W. In determined experiments, planaria were injured and incubated in water, containing $10^8$CFU *E. coli* (serotype O6:K2: H1) or with *E. coli* plus SCI and SCII (100 nM), and tissue regeneration indices assessed as described above.

In select experiments, planaria were fed homogenized beef liver (CT) or beef liver containing dsRNA for DjGst as in (28). After 8 days, planaria were either taken for whole mount in situ hybridization (WISH) or subjected to head resection and tissue regeneration assessed every day for 7 days. SC were identified and quantified 3 days post injury using lipid mediator metabololipidomies.

Planaria were surgically injured and incubated with or without Acivicin (2.5 mM). After 3 days, products were extracted by solid phase extraction (see below) and SCI and SCII levels were investigated by LC-MS-MS.

Example 6

Lipid mediator metabololipidomics and isolation of bioactive fractions: Peritoneal exudates and exudate cell incubations were immediately placed in 2 volumes of methanol. For lipid mediator profiling, 500 pg each of deuterium-labeled internal standards: $d_8$-5S-HETE, $d_4$-LTB$_4$, $d_5$-LXA$_4$, $d_4$-PGE$_2$, and $d_5$-LTC$_4$ were added to facilitate quantification in each respective chromatographic region and sample recovery. Samples were then held at −20° C. for 45 min to allow for protein precipitation and centrifuged (1200 g, 4° C., 10 min). Products were then extracted using solid phase extraction (SPE) as in (30) and eluted using methyl formate (SPE-chromatographic (SPE-C) isolates fraction 1) and methanol (SPE-C isolates fraction 2). Eluted isolates were then brought to dryness under nitrogen and suspended in methanol/water (50:50) for lipid mediator metabololipidomics or ethanol for biological evaluation. For lipid mediator metabololipidomics of known mediators and pathway products, the LC-MS-MS system was operated as in (30). For identification and quantification of SC, a Shimadzu LC-20AD HPLC and a Shimadzu SIL-20AC autoinjector (Shimadzu Corp.) paired with a QTrap 6500 (ABSciex) were employed. An Eclipse Plus C18 column (50 mm×4.6 mm×1.8 µm; Agilent) was kept in a column oven maintained at 50° C. (ThermaSphere TS-130), and LM were eluted with mobile phase consisting of methanol/water/acetic: acid of 55:45:0.01 (vol:vol:vol) that was ramped to 85:15:0.01 (vol:vol:vol) over 0.1 min, to 86:14:0.01 (vol:vol:vol) for the next 3 min, to 90:10:0.01 (vol:vol:vol) for the next 1 min and to 99.9:0:0.01 (vol:vol:vol) for the next 6 min. This was subsequently maintained at 99.9:0:0.01 (vol:vol:vol) for 2 min, and the flow rate was maintained at 0.65 ml/min. The QTrap 6500 was operated in positive ionization mode using scheduled multiple reaction monitoring (MRM) coupled with information dependent acquisition (IDA) and enhanced product ion scan (EPI).

Human milk (Biological Specialty Corporation) was placed in 2.5 volumes of ice-cold methanol; proteins were then allowed to precipitate for 30 min at 4° C. and supernatants collected. These were then acidified to pH ~3.5 and extracted using diethyl ether. Samples were then brought to dryness under a vacuum on a rotary evaporator (Buchi); products were suspended in 1 ml of methanol and extracted as detailed above using C18 SPE columns to obtain SPE-C isolate fractions.

Macrophages ($1 \times 10^7$ cells in 175 cm$^2$ flask) were transfected with ALOX12 human shRNA in pRS vector (20 µg;

Origene) or mock vector (pRS alone) using Jet-Pei transfection reagent (40 µl; following manufacturer's instruction; Polyplus-transfection SA). Seventy-two hours later, 12-LOX expression was assessed using immunofluorescent staining with human 12-LOX antibody (Novus Biologicals) or relevant isotype control and expression determined by flow cytometry. Transfected cells ($1\times10^7$/ml) were also incubated with $E.$ $coli$ ($5\times10^8$ CFU/ml, RPMI supplemented with 0.1% human serum, 37° C.) for 1 h. These incubations were stopped with 2 volumes of ice-cold methanol and isolates (SPE-C isolates fractions 1 and 2) obtained as described above.

Planaria (~200 animals) were surgically injured as described above. After 3 days, they were placed in 2 volumes of ice-cold methanol and tissues gently dispersed using a glass dounce. Homogenates were placed at −20° C. to allow for protein precipitation and SPE-C isolates fraction 2 were obtained as described above.

Example 7

SC biosynthesis, isolation and derivatives: Human macrophages ($1\times10^7$ cells/ml) were suspended in $PBS^{+/+}$ incubated with 14 HpDHA (1 µM), produced by incubation of DHA with human macrophage 12-lipoxygenase, and isolated as in (19), and $E.$ $coli$ ($1\times10^8$ CFU/ml, 37° C., pH 7.45, 30 min). Two volumes of methanol were then added and products extracted using C18 columns as outlined above.

In select experiments, human macrophages ($1\times10^7$ cells/ml) were suspended in $PBS^{+/+}$ incubated with $d_5$-14-HpDHA (1 µM) and $E.$ $coli$ ($1\times10^8$ CFU/ml, 37° C., pH 7.45, 30 min), 2 volumes of methanol were added and products extracted using SPE columns as outlined above.

SCs Obtained as detailed above were isolated using online UV-RP-HPLC (1100 Series; Agilent Technologies) and an Agilent Poroshell 120 C18 column (100 mm×4.6 mm×2.7 µm; Agilent) with mobile phase consisting of methanol/water of 55:45 (vol:vol) that was ramped to 85:15 (vol:vol) over 0.1 min, to 86:14 (vol:vol) for the next 3 min, to 90:10 (vol:vol) for the next 1 min and to 100:0 (vol:vol) for the next 6 min. This was subsequently maintained at 100:0 (vol:vol) for 2 min, and the flow rate was maintained at 0.65 mL/min. In select experiments, isolated SCI and SCII were incubated with diazomethane in diethyl ether for 30 min at room temperature. Samples were then brought to dryness and products assessed by LC-MS-MS using MRM monitoring of the following ion pairs: 549>193 and 692>336. SCI and SCII were incubated with activated Raney Nickel catalyst for 20 min at room temperature. The resulting products were then assessed by LC-MS-MS using MRM monitoring: 343>205 (See, FIGS. 6 and 8).

Human macrophages ($3\times10^7$ cells/ml) were incubated with DHA (1 µg, 37° C., PBS, pH 7.45) and $E.$ $coli$ ($1.5\times10^8$ CPU). Incubations were stopped with 2 volumes ice-cold methanol, products were extracted and levels assessed by LC-MS-MS. In select experiments, macrophages were incubated with Acivicin (2.5 mM, 37° C. PBS, pH 7.45) prior to addition of DHA (1 µg) and. Acivicin (2.5 mM) and products assessed by LC-MS-MS.

Example 8

Cell isolations: Human polymorphonuclear neutrophils (PMNs) were isolated from peripheral blood as in (15). In brief, whole blood was collected from healthy volunteers according to Partners Human Research Committee Protocol (1999P001297). Red blood cells were lysed with hypotonic buffer. PMNs were isolated using Ficoll-Histopaque 1077-1 (Sigma-Aldrich, St. Louis, Mo., USA) density gradient and resuspended in Dulbecco's PBS.

Human macrophages were obtained from peripheral blood mononuclear cells isolated from leukopacks, procured from Children's Hospital Blood Bank (Boston, Mass., USA). Monocytes were cultured for 7 d in RPMI 1640 medium (Life Technologies, Carlsbad, Calif., USA) supplemented with 10% fetal bovine serum (Invitrogen, Grand island, N.Y., USA), 2 mM L-glutamine (Lonza, Basel, Switzerland) penicillin-streptomycin (Lonza), and granulocyte macrophage-stimulating factor (10 ng/ml; R&D Systems, Minneapolis, Minn., USA) (15).

Example 9

Macrophage bacterial phagocytosis, efferocytosis, and phagolysosontal acidification: Human macrophages were plated in 96-well plates ($5\times10^4$ cells per well) for 24 h, and phagocytosis or efferocytosis was assessed as in (14). In brief, apoptotic PMNs were obtained by culturing cells overnight in $PBS^{-/-}$ ($5\times10^6$ cells/ml). Apoptotic human PMNs were labeled with bisbenzimide H33342 trihydrochloride (Sigma-Aldrich). Human macrophages were incubated with 0.1-10 nM concentration of test products, and then labeled apoptotic PMNs were cocultured with macrophages for 40 min [37° C. (pK 7.45)]. Fluorescence was read on a SpectraMax M3 plate reader (Molecular Devices, Sunnyvale, Calif., USA), and results were analyzed using SoftMax Pro (Molecular Devices).

Macrophage phagocytosis was assessed using fluorescently labeled $E.$ $coli$ (serotype O6:K2;H1) with BacLight Green Bacterial Stain (Life Technologies, Eugene, Oreg., USA). $E.$ $coli$ [$2.5\times10^6$ colony-forming units (CFL)/well] were then added to macrophages previously plated in 96-well plates (40 min at 37° C.) and incubated with 0.1-10 nM concentration of test compounds [15 min at 37° C. (pH 7.45)]. Fluorescence was measured on a SpectraMax M3 plate reader, and results were analyzed using SoftMax Pro.

Macrophage phagolysosomal acidification was assessed by incubating macrophages with pHrodo dye (Invitrogen) following the manufacturer's instructions. Subsequently, cells were incubated with 1 nM of test compounds (15 min at 37° C.), $E.$ $coli$ ($2.5\times10^6$ CFU/well) were added, and fluorescence was assessed after 60 min (37° C.) using a BZ9000 microscope equipped with a ×20 objective (Keyence, Itasca, Ill., USA) and a fluorescence plate reader.

Example 10

Microbially induced mouse peritonitis: FVB mice, 6-8-week-old, purchased from Charles River Laboratories (Wilmington, Mass., USA) were fed ad libitum Laboratory Rodent Diet 20-5058 (Lab Diet; Purina Mills, St. Louis, Mo., USA). Mouse experimental procedures were approved by the Standing Committee on Animals of Harvard Medical School (Protocol 02570) and complied with institutional and U.S. National institutes of Health (NIH) guidelines. $E.$ $coli$ (serotype O6:K2:H1) was cultured in Luria-Bertani broth and harvested at midlog phase ($OD_{600\ nm}$≈0.5 absorbance units, $5\times10^8$ CFU/ml). Mice were given an intraperitoneal injection containing $E.$ $coli$ ($5\times10^4$ CFU/mouse). Four hours later, mice were administered $15\times10^6$ apoptotic PMNs or saline via intraperitoneal injection, and 8 h later, peritoneal exudates were collected as described in (11). Cellular composition was determined by differential leukocyte count and flow cytometry. For flow cytometry, cells were labeled with fluorescently conjugated antibodies against mouse surface CD11b (clone M1/70; eBioscience, San Diego, Calif., US), F4/80 (clone BM8; eBioscience), Ly-6G (clone RB6-8C; eBioscience), and intracellular stained with anti-E. coli antibody (clone GTX408556; GeneTex, Irvine, Calif., USA). Bacterial clearance was measured by culturing exudates on plates containing Luria-Bertani agar overnight at 37° C.

Example 11

Sulfido-conjugate biosynthesis and chromatography tandem mass spectrometry identification: Cell incubations, self-limited infectious exudates, mouse spleens, deidentified human spleens (purchased from Cooperative Human Tissue Network, Philadelphia, Pa., USA), and deidentified human plasma from patients diagnosed with sepsis (purchased from Dx Biosamples, San Diego, Calif., USA) were placed in 2 volumes of methanol. For lipid mediator (LM) profiling, 500 pg deuterium-labeled internal standards $d_8$-5S-HETE and $d_5$-LTC$_4$ was added to facilitate quantification and assessment of sample recovery. Samples were then held at −20° C. for 45 min to allow for protein precipitation and were centrifuged (1200 g at 4° C. for 10 min). Products were extracted using solid-phase extraction as described (14) and eluted using methanol. Eluted isolates were then brought to dryness under nitrogen and suspended in methanol:water (50:50) for LM metabololipidomics. For LM metabololipidomics of sulfido-conjugates, the liquid chromatography tandem mass spectrometry (LC-MS-MS) system was operated as described (14) with minor modifications. Shimadzu LC-20AD HPLC (Tokyo, Japan) and a Shimadzu SIL-20AC autoinjector paired with a QTrap 5500 (AB Sciex, Framingham, Mass., USA) were used. A Poroshell 120 EC-C18 column (100 mm×4.6 mm×2.7 µm; Agilent Technologies, Santa Clara, Calif., USA) was kept in a column oven maintained at 50° C. (ThermaSphere model TS-130; Phenomenex, Torrance, Calif., USA), and LMs were eluted with a mobile phase consisting of methanol:water:acetic acid at 55:45:0.1 (vol:vol:vol) that was isocratic for 1 min, ramped to 70:30:0.1 (vol:vol:vol) over 5 min, then to 80:20:0.1 (vol:vol:vol) for 2 min. then isocratic 80:20:0.1 (vol:vol:vol) for the next 3 min, and ramped to 98:2:0.1 (vol:vol:vol) over 3 min. This was subsequently maintained at 98:2:0.11 (vol:vol:vol) for 3 min, and the flow rate was maintained at 0.60 ml/min. The QTrap 5500 was operated in positive ionization mode using scheduled multiple reaction monitoring (MRM) coupled with information-dependent acquisition and enhanced product ion scan.

Human macrophage cell line KG1A, 1×10$^7$ cells/ml; American Type Culture Collection, Manassas, Va., USA) was suspended in PBS$^{+/-}$ incubated with 17S-hydro(peroxy)-4Z,7Z,10Z,13Z,15E,19Z-docosahexaenoic acid (17-HpD; 30 µM) and E. coli [1×10$^8$ CFU/ml at 37° C. (pH 7.45) for 30 min]. The 17-HpD was produced. by incubation of DHA with soybean lipoxygenase and isolated as in (10). There were 2 volumes of methanol then added, and products were extracted using C18 columns as outlined above. In select experiments, mouse spleens were incubated with $d_5$-DHA [10 µM, (pH 7.45) for 30 min, PBS$^{+/+}$] and norepinephrine (10 µM). Incubations were stopped with 2 volumes of ice-cold methanol and products extracted as above.

Products used for biologic evaluation and structure elucidation were obtained as detailed above and isolated using online UV-RP-HPLC (1100 Series; Agilent Technologies) and a Poroshell 120 EC-C18 column (100 mm×4.6 mm×2.7 µm) with the 2 mobile phases consisting of solvent A [methanol:acetonitrile (35:65 vol:vol)] and solvent B (water containing 8.3 M acetic acid and buffered to pH 5.7 with ammonium hydroxide). Solvent A was maintained at 10% for 0.3 min, then ramped to 30% over 0.2 min. This was maintained for 1.5 min and then ramped to 50% over 0.1 min, and the flow rate was reduced from 0.6 to 0.2 ml/min. Solvent B was ramped to 53% and the flow rate increased to 0.3 ml/min over the subsequent 38 min. This was then ramped to 100% over the next 8 min and the flow rate increased to 0.6 ml/min, which was maintained for 5 min. In select experiments, isolated products were incubated with freshly prepared diazomethane in diethyl ether for 30 min at room temperature. Samples were then brought to dryness, and products were assessed by LC-MS-MS using MRM of the following, ion pairs: 492>135, 508>135, 565>193, 549>193, 692>336, and 708>336.

In select experiments, human macrophages (~4.5×10$^7$ cells/ml) were incubated with DHA (10.5 µM) or 17-HpD [10 µM at 37° C. (pH 7.45)] and E. coli (1:50) for 30 min at 37° C. Incubations were stopped with 2 volumes of ice-cold methanol, products were extracted, and levels assessed by LC-MS-MS. Macrophages were also incubated with or without Acivicin [2.5 mM at 37° C., PBS (pH 7.45)], a γ-glutamyl transferase (GGT) agent that inhibits LT D$_4$ formation (16), before addition of 17-HpD (10 µM) and E. coli (1:50; 60 min), and products were taken to LC-NIS-MS.

Example 12

Planaria regeneration: Planaria (Dugesia japonica) were kept in water (Poland. Spring; Nestlé Waters North America, Stamford, Conn., USA) at 18° C. All animals were starved for at least 7 d before the experiments. Tissue regeneration was assessed as described previously (10). In brief, planaria were subjected to head resection postoccularly (surgical injury). The posterior portions of the planaria were then placed in spring water containing 0.01% EtOH, 16-glutathionyl, 17-hydroxyl-4Z,7Z,10,12,14,19Z-docosahexaenoic acid plus 16-cysteinylglycinyl, 7-hydroxyl-4Z,7Z,10,12,14, 19Z-docosahexaenoic acid (50 nM; each) or 8-gutathionyl, 7,17-dihydroxyl-4Z9,11,13Z,15E,19Z-docosahexaenoic acid plus 8-cysteinylglycinyl, 7,17-dihydroxyl-4Z,9,11,13Z, 15E,19Z-docosahexaenoic acid (50 nM, each). The extent of tissue regeneration during a 6-d period was determined using captured images of the regenerating blastemas at regular intervals (24 h). These images were analyzed using ImageJ software (NIH, Bethesda, Md., USA). A tissue regeneration index (TRI) was used that took into consideration the size of the regenerated tissue total area (A) and the postocular width (W), where TRI=A/W (10).

Discussion

To obtain self-resolving infectious exudates and assess tissue regeneration, the inventors used murine Escherichia coli (E. coli) peritonitis relevant to human infections and mapped leukocyte trafficking. E. coli inoculation at 10$^5$ CFU/mouse i.p. gave a self-limited host response that reached maximal neutrophil infiltration at 12 h and subsequently declined (FIG. 1A). Monocyte/macrophage numbers increased between 4 and 24 h demarking onset of the resolution phase. The inventors next isolated products from resolving infectious exudates (i.e. 24 h) and assessed their ability, with planaria, to stimulate tissue regeneration. Since MaR1 stimulates tissue regeneration (12) and elutes within methyl formate fractions from C18 solid phase extraction (referred to as solid phase extraction chromatographic (SPE-C) isolate fraction 1), the inventors sought evidence for signals in distinct chromatographic fractions. Here, the inventors assessed eluates in methanol fractions (SPE-C isolate fraction 2) for previously undescribed signals that displayed tissue regenerative properties. Planaria undergo both restorative and physiological regeneration via evolutionarily conserved pathways, making this an ideal system to identify chemical signals involved in tissue regeneration (14). To this end, planaria (Dugesia japonica) were injured on day 0 and time-dependent head regeneration monitored. To quantitate regeneration, the inventors calculated, tissue regeneration indices (TRI) (12). Following head resection, regeneration ensued, giving a $TRI_{max}$ (maximum tissue regeneration) at 6 days and $T_{50}$ (the interval at which 50% regeneration, $TRI_{50}$, occurred) 4.3 days (FIG. 1B). Isolates from 24 h infectious-resolving exudates dose-dependently accelerated head regeneration ($r^2$=0.91) as early as 2 days after surgery, shortening $T_{50}$ to ~3.3 days. For direct comparison, maresin 1 (MaR1; FIG. 1B and FIG. 2A), the known dihydroxy-containing potent macrophage-derived proresolving mediator (12), accelerated this process to essentially the same extent. Towards human translation, and because milk carries nutrients and is appreciated to have products relevant to infant development and immune status (15), the inventors also assessed tissue regenerative properties of human milk isolates using the same chromatographic fractions (FIG. 1B). Incubation of planaria with human milk isolates dose-dependently accelerated regeneration and reduced $T_{50}$ from ~4.3 to ~3.5 days (FIG. 1B and FIG. 2B). These results demonstrate that both mouse resolving-exudates and human milk possess tissue regenerative properties that elute within the methanol fractions from solid-phase C18 extractions.

Next the inventors investigated whether these bioactive molecules regulated signaling pathways that trigger head-to-tail differentiation in D. japonica (16). Two days post-injury, in regenerating blastemas, isolates from both mouse resolving-exudates and human milk significantly increased expression of fibroblast growth factor receptor-like gene nou-darake (Djndk) and mitogen-activated protein kinase phosphatase gene (Djmpka; FIG. 1C), and downregulated DjAdb-Ba (Abdominal-B-like gene), a target Hox gene of posterior Wnt/β-catenin signaling in neoblast progeny (14, 16). Since extracellular signal-regulated kinase (ERK) regulates expression of these genes (16), the inventors tested whether ERK signaling was responsible for the actions of molecules from resolving exudates. ERK inhibition abrogated regenerative actions of these infectious resolving-exudates (FIG. 2C). Together these results suggest that the ERK signaling is involved in the regenerative actions of molecules from resolving infectious exudates.

Macrophages are key in regulating host responses during inflammation-infection, coordinating both the onset and resolution of inflammatory responses (8, 17, 18). During sterile inflammation the resolution phase is characterized by increases in resolution phase macrophages (rM) (18) and production of maresins (19). Using lipid mediator metabotolipidomics, the inventors identified MaR1 and related isomers within SPE-C isolate fraction 1 as well as previously undescribed signals in SPE-C isolate fraction 2 in infectious resolving exudates n=3 mice exudates). Hence, SPE-C isolate fraction 2 obtained from both mouse resolving exudates and human milk carried regenerative properties (FIGS. 1B, C) that were unique and distinct from MaR1 (12), which elutes within SPE-C isolate fraction 1 (See Table 1).

TABLE 1

Evidence for the structure, biosynthesis, and actions of SCI and SCII

| 14-Series SC | Biological systems identified in | Structure elucidation | Biosynthetic evidence | Bioactions In vivo | Bioactions In vivo |
|---|---|---|---|---|---|
| SCI | Mouse infectious exudates Human Milk Human Macrophages Regenerating Planaria | $^{14}$C-DHA elution in MeOH fraction (SPEC isolate fraction 2) Retention time 6.5 min UV Chromophore triplet band of absorption $\lambda_{max}$ 280 nm MS-MS spectrum of natural product (diagnostic ions): m/z 650 (M-H), 618, 521, 503, 418, 400, 434, 325, 308, 233, 191, 179, 162 MS-MS spectrum of deuterium-labeled product (diagnostic ions): m/z 655 (M-H), 637, 598, 580, 423, 405, 348, 330, 233, 217, 215, 191, 179, 162 MS-MS spectrum of trimethyl ester derivative (diagnostic ions): m/z 692 (M-H), 660, 549, 432, 414, 357, 325, 336, 249, 217, 219, 205, 193, 176 Raney nickel derivative MS-MS spectrum (diagnostic ions): m/z 343, 325, 299, 281, 233, 205, 189, 161 | Knockdown of 12 LOX in human LOX inhibition in planana Knockdown of GST in planaria Product precursor temporal relationships to DHA, 14HpDHA, and SCI with human macrophages Inhibition of λ-glutamyl transferase in human macrophages and planaria | Promotes tissue regeneration in planaria in a dose dependent manner ($R^2$ = 0.85) Regulates key genes in tissue regeneration Promotes resolution of infections in mice* Stimulates mouse macrophage* phagocytosis of E. coli Reduces systemic proinflammatory eicosanoids* Protects from neutrophil mediates tissue damage Promotes tissue repair upregulating Ki67 and RSPO3* | Stimulates human macrophase efferocytosis in a does dependent manner Stimulates human macrophage and neutrophil phagocytosis of E. coli in a dose dependence matter Stimulates human macrophage and neutrophil ROS production in a dose dependence manner |
| SCII | Mouse infectious exudates Human Milk Human Macrophages Regenerating Planaria | $^{14}$C-DHA elution in MeOH fraction (SPEC isolate fraction 2) Retention time 4.7 min UV Chromophore $\lambda_{max}$ 280 nm MS-MS spectrum of natural product (diagnostic ions): m/z 521, 504, 477, 459, 434, 329, 325, 235, 205, 191, 173, 147, 109 MS-MS spectrum of deuterium-labeled product (diagnostic ions): m/z 526, 509, 482, 464, 348, 334, 330, 235, 217, 205, 173, 114 | Knockdown of 12 LOX in human LOX inhibition in planaria Knockdown of GST in planaria Product precursor temporal relationships to DHA, 14HpDHA, and SCII with human macrophages | Promotes tissue regeneration in planana in a dose dependent manner ($R^2$ = 0.97 Regulates key genes in tissue regeneration Promotes resolution of infections in mice* Stimulates mouse macrophage* phagocytosis of E. coli | Stimulates human macrophase efferocytosis in a does dependent manner Stimulates human macrophage and neutrophil phagocytosis of E. coli in a dose dependence matter macrophage and |

TABLE 1-continued

Evidence for the structure, biosynthesis, and actions of SCI and SCII

| 14-Series SC | Biological systems identified in | Structure elucidation | Biosynthetic evidence | Bioactions In vivo | Bioactions In vivo |
|---|---|---|---|---|---|
| | | MS-MS spectrum of trimethyl ester derivative (diagnostic ions): m/z 549, 532, 505, 487, 357, 339, 249, 219, 205, 161, 109 Raney nickel derivative MS-MS spectrum (diagnostic ions): m/z 343, 325, 299, 281, 233, 205, 189, 161 | Inhibition of λ-glutamyl transferase in human macrophages and planaria | Reduces systemic proinflammatory eicosanoids* Protects from neutrophil mediates tissue damage Promotes tissue repair upregulating K167 and RSPO3* | neutrophil ROS production in a dose dependence manner |

Spectra were recorded online in methanol/water using an Agilent Technologies 1100 series diode array detector
*These bioactions were determined following co-administration of equal amounts of SCI and SCII.
n = 3 or greater for experiments for structure elucidation.
n = 3-4 for human neutrophil and macrophage assays and for in vivo experiments.
n = 7 or greater for planaria experiments Based on these findings, the inventors next assessed the role of human macrophage 12-lipoxygenase (LOX) (20) in the biosynthesis of these new products. Isolates obtained from human macrophages (HMΦ)) carried tissue regenerative actions with *D. japonica* that were lost in cells transfected with shRNA targeting 12-LOX (FIG. 1D). In HMΦ docosahexaenoic acid (DHA) is 12-LOX substrate in maresin biosynthesis (20, 21); therefore, the inventors investigated whether the bioactive products in SPE-C isolate fraction 2 were also from DHA. Incubation of infectious exudates obtained from self-resolving peritonitis with radio-labeled DHA demonstrated accumulation of labeled material in SPE-C isolate fraction 2 at both 12 h (peak of inflammation) and 24 h (resolution; FIG. 3A). In these fractions, significantly higher radioactivity from DHA was present in exudates from mice with self-resolving peritonitis compared to those with delayed-resolving peritonitis. Presence of four DHA-derived products in these isolates was confirmed using liquid chromatography tandem mass spectrometry (LC-MS-MS) (FIG. 3B).

Peaks I and II gave essentially identical MS-MS fragmentation patterns, with the parent ion (M+H) displaying m/z at 521. Spectra from peaks III and IV also gave identical MS-MS fragmentation with m/z for the parent ion at 650, suggesting that I and II were likely related to each other and III and IV were related to each other (FIGS. 4A, B). Similar results were also obtained with human milk, regenerating planaria and human macrophages (FIGS. 3C and 4C-F). In macrophages transfected with 12-LOX shRNA when compared to mock transfected quantification of products in SPE-C isolate fraction 2 using LC-MS-MS demonstrated a significant reduction in the levels of products identified under peaks I-IV (FIG. 4G). These results are in line with the observed reduction in biological activity of these isolates (FIG. 1D), implicating HMΦ 12-LOX in the initiation of these signals.

Because 14S-hydro(peroxy)-docosahexaenoic acid (14S-HpDHA) is the product of HMΦ12-LOX biosynthetic precursor to maresins, the inventors tested whether 14S-HpDHA was precursor to the new regenerative molecules. Incubation of HMΦ with 14S-HpDHA also gave products III and IV (FIG. 5A) as well as I and II (FIG. 5B). Products beneath III and IV each gave ultraviolet (UV)-chromophores with maximum absorbance at 280 nm and shoulders at 270 nm and 295 nm in reverse phase-high pressure liquid chromatography mobile phase (FIG. 6A), characteristic of a conjugated triene double bond system coupled to an auxochrome allylic to the triene such as sulphur (6, 22). This was corroborated in incubations with a desulphurization reagent, Raney Nickel (6, 22), that gave 14-HDHA (FIGS. 6B, C). These results together with MS-MS fragmentation indicated a 13-glutathionyl, 14-hydroxy- and 22-carbon backbone that originated from DHA (FIG. 5A) and therefore was coined sulfido-conjugated product I (SCI). To gain further evidence for this deduced structure, the inventors assessed deuterium incorporation in SCI with HMΦ and $d_5$-14S-HpDHA. (FIG. 7A). $d_5$-SCI gave the expected 5-Dalton shift in the parent ion mass, from m/z 650 to m/z 655, as well as in the m/z of fragments containing carbons 21 and 22, including that resulting from a diagnostic 14-15 carbon break, which increased in mass from m/z 109 to m/z 114 (FIG. 7C). The proposed glutathione conjugate structure was further corroborated by treating SCI (FIGS. 7B, C) with diazomethane. This approach was also employed to elucidate the structure of the products beneath I and II, i.e. 13-cysteinylglycinyl, 14-hydroxy-docosahexaenoic acid (SCII; FIGS. 5B, 8 and 9).

The inventors next confirmed that these new molecules carried tissue regenerative properties. Planaria incubated with SCI and SCII gave accelerated tissue regeneration ($T_{50}$ from ~4 days to ~3 days; FIG. 10C). To investigate the role of endogenous SC in planaria tissue regeneration, *D. japonica* was incubated with a LOX inhibitor (baicalein) that reduced levels of both SCI and SCII measured 3 days post-surgery (FIG. 5D) and significantly delayed head regrowth (FIG. 5E). This was rescued when planaria were incubated with SCI and SCII (FIG. 5E). The inventors next investigated the ability of SC to promote tissue regeneration during infection. Incubation of D. japonica with *E. coli* gave a delay in regeneration, $T_{50}$ from ~3.5 to ~4.2 days that was rescued by SCI and SCII addition (FIG. 5E). Having established that together SCI and SCII displayed tissue regenerative actions, the inventors next sought evidence for their individual biological actions. Incubation of injured planaria with either SCI or SCII accelerated head regrowth. This proved to be concentration dependent, reducing $T_{50}$ from ~5 days to ~3.5 days (FIGS. 10A, B and 11) with an $r^2$ value of 0.85 for SCI and 0.97 for SCII (FIG. 11). In addition, each of SCI and sCII upregulated genes involved in head regeneration (FIG. 10C).

Bioactive lipid mediators that are peptide conjugates such as cysteinyl-leukotrienes involve Glutathione S-transferase (GST) enzymes in their biosynthesis (see 10, 23). Further, it is well recognized that compounds targeted by GST are bioactive. Therefore, it is reasonable to postulate that because the SCs identified herein are conjugated at their epoxide carbon, other essential fatty acids, such as eicosapentaenoic acid (EPA), having 5(6)-epoxide derivatives, may also be similarly functionalized by GST as are the MIA derivatives SCI and SCII identified herein.

Therefore, the inventors assessed the role of *D. japonica* GST in SC biosynthesis. Whole mount in situ hybridization (WISH) of uninjured planaria confirmed the expression of *D. japonica* GST (DjGst), which was temporally regulated following injury in regenerating blastemas (FIG. 12A). Double-stranded RNA knockdown of DjGst (FIG. 12B) delayed tissue regeneration (FIG. 12C) and reduced SCs levels (>80%; FIG. 12D) in regenerating planaria. Alignment of deduced *D. japonica* GST amino acid sequence with human and mouse GST-µ4 (Table 2) demonstrated >70% sequence homology between the planarian and mammalian enzymes that is also expressed in HMΦ(n=4). These results indicate that GST enzyme(s) are involved in SCs biosynthesis and are involved in tissue regeneration in planaria.

during infection in mice. For quantitative assessment of resolution components with *E. coli* infection, the inventors employed resolution indices (11). Inoculation of mice with $10^5$ CFU *E. coli* (self-limited inoculum) gave a $T_{max}$~12 h, $T_{50}$~32 h and a resolution interval ($R_i$) of ~20 h (FIG. 14A), SCI and SCII (50 ng each per mouse) significantly reduced neutrophil numbers at 24 h, shortening $R_i$ to ~10 h (FIG. 14A) and promoted exudate macrophage phenotype switch towards an rM phenotype, increasing rM markers including TIMD4 (~34%), IL10 (~15%) and. Arginase 1 (~76% n=4 mice per group). SCs also gave significant increases in leukocyte phagocytosis of *E. coli* in vivo in mice (FIG. 14B), For human translation, the inventors determined the actions of SCI and SCII on human phagocytes, where each dose-dependently increased macrophage efferocytosis of apoptotic cells, a key proresolving action (3), to a similar extent as MaR1 (FIG. 14C). Of note, SCI and SCII each enhanced bacterial phagocytosis and intracellular reactive oxygen species (FIG. 15) used in bacterial killing (11, 17).

The inventors tested SC isolates from regenerating planaria to determine if they displayed actions in mammalian species. Here, they significantly reduced neutrophil recruit-

TABLE 2

DjGst displays high sequence homology with human and mouse Glutathione S-transferase mu4.

| Organism | | Sequence | |
|---|---|---|---|
| Dugesia japoinica | 1 | MAPLLGYWKIRGLAQSIRLLLEYTGEEYNEKYYELGN--DFNRDDWLNEKFSLGLSFPNLPYLIDGDLKLTQSSAILRYL | 78 |
| Mus musculus | 1 | MPMTLGYWDIRGLAHAIRLLLEYTGSSYEEKRYTMGDAPDYDRSQWLSEKFKLGLDFPNLPYLIDGSHKITQSNAILRYI | 80 |
| Homo sapiens | 1 | MSMTLGYWDIRGLAHAIRLLLEYTDSSYEEKKYTMGDAPDYDRSQWLNEKFKLGLDFPNLPYLIDGAHKITQSNAILCYI | 80 |
| Dugesia japoinica | 79 | AEKHNMVGETSEERARTMMLAEEVQDLRMGFARLCYNPDFANLKHEYLSQLPSRLKLFSDFIGTKHWLMGEKLTYPDFHF | 158 |
| Mus musculus | 81 | ARKHNLCGETEEEKIRVDILENQAMDVSNQLARVCYSPDFEKLKVEYLEQLPGMVKLFSQFLGQRTWFVGEKITFVDFLA | 160 |
| Homo sapiens | 81 | ARKHNLCGETEEEKIRVDILENQAMDVSNQLARVCYSPDFEKLKPEYLEELPTMMQHFSQFLGKRFWEVGDKITFVDFLA | 160 |
| Dugesia japoinica | 159 | YIMLDSLKILSPICLDEFDNLKNYLENFEKLEPIAKYMESDKYIQKPLNNKVVKFGGDch | 218 |
| Mus musculus | 161 | YDILDLHLTFEPTCLDAFPNLKDFVARFEVLKRISAYMKTSRFLRTPLYTKVATWGNK-- | 218 |
| Homo sapiens | 161 | YDVLDLHRIFEPNCLDAFPNLKDFISRFEGLEKISAYMKSSRFLPKPLYTRVAVWGNK-- | 218 |

Protein sequence for human (UniProt:Q03013-1) and mouse (UniProt:Q8R516) Glutathione S-transferase mu4 were aligned to DjGst (EMBL ADX68807.1) using COBALT (http://www.ncbi.nlm.nih.gov/tools/cobalt/cobalt.cgi?CMD=submit)

With human macrophages, the inventors investigated product-precursor relationships for DHA to SCI and SCII. DHA was rapidly converted by activated human macrophages to SCI with levels reaching a maximum at 15 min. SCII was also rapidly produced in these incubations with levels that remained elevated between 15 and 60 min (FIG. 13A). Essentially similar relationships were obtained with activated human macrophages and 14S-HpDHA (n=3 separate incubations). In order to assess whether SCI was precursor to SCII, the inventors next incubated human macrophages with a γ-glutamyl transferrase inhibitor (Acivicin), known to inhibit leukotriene (LT) $D_4$ formation (24). Incubation of activated human macrophages with this inhibitor gave a significant increase in SCI and a reduction in SCII levels in these incubations (FIG. 13B). Similar results were obtained with regenerating planaria where addition of the inhibitor increased SCI level and decreased SCII levels 2 days post injury (FIG. 13C).

Since SC were biosynthesized in both resolving infectious exudates (FIG. 3) and regenerating planaria (FIGS. 12, 13), the inventors determined their ability to stimulate resolution ment in murine peritonitis (FIG. 16A) and exudate eicosanoid levels including $LTB_4$ and thromboxane (Tx) $B_2$, actions that by direct comparison were shared with MaR1 (FIGS. 16B, C). Planarian SC isolates also stimulated human macrophage efferocytosis of apoptotic neutrophils (FIG. 16D). Hence these results indicated that SCs are anti-inflammatory and proresolving, and their structure-functions conserved from planaria, mice and humans.

Vessel occlusion is a common consequence of many inflammatory conditions, leading to local ischemia that, upon reflow, can result in second organ injury by activated leukocytes and, in extreme cases, organ failure (25). SCI and SCII gave significant protection from leukocyte-mediated tissue damage (FIG. 18A) decreasing leukocyte infiltration/migration into lungs and spleens, actions comparable to RvD1 (FIG. 17A). SCs also reduced plasma eicosanoid levels, including $LTB_4$, $LTC_4$ and $TxB_2$ (FIGS. 17B, C). In addition, immunofluorescence analysis of lung sections from mice given SCI and SCII demonstrated an upregulation of antigen Ki67, which plays a role in cell proliferation (26) and Roof plate-specific Spondin 3 (RSPO3; FIG. 18B), which displays tissue regenerative actions (27).

Figure 1:
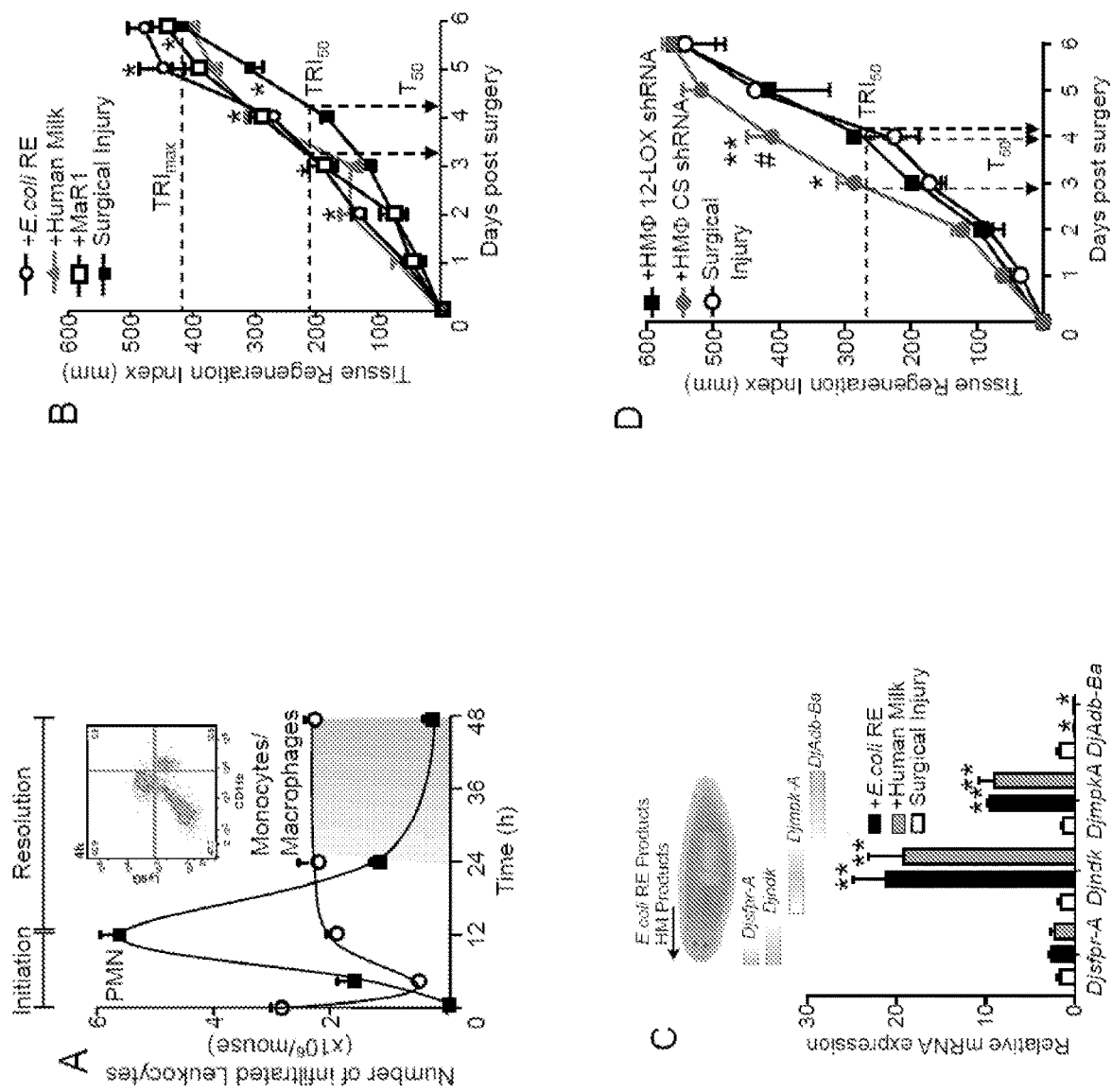
FIG. 1: New pathway promotes tissue regeneration. (A) Leukocyte recruitment following *E. coli* ($10^5$ CFU/mouse, i.p.) inoculation (see methods). Results are mean±sem. n=4 mice/time-point. (B) Surgically injured planaria were incubated with SPE-chromatographic (SPE-C) isolate fraction 2 from *E. coli* resolving infectious exudates (RE), from human milk, maresin 1 (MaR1; 100 nM) or vehicle (surgical injury; water containing 0.01% EtOH). Tissue regeneration indices were determined. $T_{50}$=time interval corresponding to 50% of maximal tissue regeneration-TRI$_{50}$. (C) Gene expression in regenerating blastemas (bottom panel). Results are mean±sem. n=3 per group pooled from blastemas of 9 animals. (D) Injured planaria were incubated with SPE-C isolate fraction 2 from human macrophages (HMΦ) transfected with shRNA for 12-lipoxygenase (12-LOX shRNA), control scrambled sequence (CS shRN), or vehicle. B, D: Results are mean±sem. n=9 planaria per incubation. *P<0.05, **P<0.0001 vs. surgical injury group. #P<0.01 vs 12-LOX shRNA at day 4.

Several lines of evidence support the proposed biosynthetic scheme for the formation of SC signals in FIG. 19. They are as follows: (i) DHA is converted by HMΦ 12-LOX to 14S-HpDHA and 13(14)-epoxide intermediate, demonstrated using acid methanol trapping with human cells and recombinant enzyme (13, 20). Knockdown of macrophage 12-LOX reduced both SCI and SCII (FIG. 4) as well as loss the of tissue regenerative actions of SPE-C isolate fraction 2 (FIG. 1); (ii) radiolabel from precursor $^{14}$C-DHA was recovered in SPE-C isolate fraction 2 that was distinct from MaR1 containing fractions (FIG. 3); (iii) reciprocity in product-precursor relationships between DHA, SCI and SCII (FIG. 13) as well as between 14HpDHA and SCI and SCII (iv) Inhibition of planaria LOX reduced both SCI and SCII in regenerating planaria and delayed tissue regeneration that was rescued by addition of SCI and SCII (FIG. 5); (v) knockdown of planaria GST reduces both SCI and SCII levels in regenerating planaria and delays tissue regeneration (FIG. 12); (vi) incubation of human macrophages and regenerating planaria γ-glutamyl transferrase inhibitor led to increased SCI and a decreased SCII (FIG. 13); (vii) SCI and SCII carry distinct structures from that of MaR1 (12) as demonstrated by LC-MS-MS results of the free acids (FIGS. 3, 4, and 5), tri and dimethyl-ester derivative as well as deuterium incorporation from DHA (FIGS. 7, 13); (viii) identification of 14-HDHA from incubations of SCI and SCII with Raney Nickel as well as SCI and SCII respective UV chromophores support the presence of a sulfido-group allyllic to a triene double bond system in each of these molecules (FIGS. 6 and 8); (ix) SCI and SCII isolated using RP-UV-HPLC each separately regulated human phagocyte responses and promoted tissue regeneration in planaria in a dose dependent manner (FIGS. 10, 11, 14 and 15); (x) when administered together in vivo, SCI and SCII regulated host mouse responses to E. coli infections promoting clearance of bacteria and resolution of infections (xi) SCI and SCII together protected against second organ reflow injury (collateral tissue damage) and promoted tissue repair (FIGS. 14, 17 and 18; and Table 1).

Identification of Novel Sulfido-Conjugates During Sell-Resolving E. Coli Infections in Mice and with Human Spleens To investigate the production of novel molecules during self-limited acute inflammation, the inventors initiated peritonitis in mice with a self-limited E. coli inoculum (11). Given that the spleen is key in regulating immune responses during infections and is rich in LMs (17), spleens were profiled from E. coli-inoculated mice during the onset of the inflammatory response and its resolution. LC-MS-MS-based LM profiling targeting molecules containing a DHA backbone and carrying a glutathionyl, cysteinylglycinyl, or a cysteinyl group gave 2 distinct peaks: the first eluting with a retention time ($T_R$) of 9.7 min (I), and the second peak (II) at $T_R$ 10.4 min (FIG. 22A).

Assessment of the mass spectrometry (MS) spectrum for product beneath peak I gave a parent ion (M+H) with mass-to-charge ratio (m/z) of 650 and a daughter ion with m/z of 308, suggesting that this contained a DHA backbone carrying a hydroxy and a glutathionyl group (14). The MS-MS fragmentation pattern for this molecule gave ions with an of 565 and 548, consistent with the hydroxy group being carried at carbon 17 (FIG. 22B) of the 22-carbon backbone. In addition, ions with m/z 275, 231, and 213 were consistent with the glutathione group carried at carbon 16 of the DHA backbone, thus indicating that this molecule was 16-glutathionyl, 17-hydroxy-4Z,7Z,10,12,14,19Z-docosahexaenoic acid. The MS spectrum of signal II gave a parent ion with in/z of 464 and a daughter ion with m/z 343 and 121 that are consistent with a molecule that contains a 22-carbon DHA backbone, a hydroxy group, and a cysteinyl group. The MS-MS spectrum for this molecule gave ions with m/z 365, consistent with an alcohol group at carbon 17, and ions with m/z 275, 231, and 213, consistent with a cysteinyl group carried at carbon 16, thus indicating that this molecule was 16-cysteinyl, 17-hydroxy-4Z,7Z,10,12,14,19Z-docosahexaenoic acid (FIG. 22C). Levels for each of these molecules were assessed during the course of infection. Using MRM, their levels were found to increase during the course of the inflammatory response, with highest levels found at the 24 h interval (FIG. 22D). Of note, cysteinyl LT levels were substantially lower in spleens from mice with peritonitis, during the resolution phase, than the new DHA-derived sulfido-conjugates (FIG. 22D). These results suggest that the novel sulfido-conjugated molecules may regulate leukocyte responses during the resolution of inflammation.

The inventors next investigated the production of sulfido-conjugates at the site of inflammation, LC-MS-MS-based LM metabololipidomics of self-limited inflammatory exudates from E. coli-inoculated mice gave 3 peaks (FIG. 23A). Peak I gave a $T_R$ of 8.0 min, a parent ion in the MS with m/z 666, and a daughter ion with m/z 308. These were consistent with a DHA backbone carrying 2 hydroxy and a glutathionyl group (FIGS. 23A, B). Assessment of the MS-MS spectrum for this molecule gave ions with m/z 537 and 203, indicating that the hydroxy groups were carried at carbon positions 7 and 17, whereas ions with m/z 247, 217, 211, 199, and 185 were consistent with the glutathionyl group at carbon position 8. Thus, the structure was assigned as 8-glutathionyl, 7,17-dihydroxy-4Z,9,11,13Z,15E,19Z-docosahexaenoic acid.

Peak 11 gave a $T_R$ of 9.3 min with a parent ion in MS of m/z 521 and daughter ion with m/z 179; this was consistent with a DHA backbone carrying 1 hydroxy and a cysteinylglycinyl. The MS-MS spectrum for this molecule gave ions with m/z 442, consistent with the hydroxy group being carried on carbon 17. Ions with m/z 275, 231, and 213 were consistent with a cysteinylglycinyl group carried at carbon 16; therefore, the structure of this product was assigned as 16-cysteinylglycinyl, 17-hydroxy-4Z,7Z,10,12,14,19Z-docosahexaenoic acid. Peak III gave essentially the same retention and MS-MS fragmentation at that found for 16-glutathionyl, 17-hydroxy-4Z,7Z,10,12,14,19Z-docosahexaenoic acid (FIGS. 23A, C). Temporal regulation of these molecules demonstrates that during the course of inflammation in infectious inflammatory exudates, levels of 8-glutathionyl, 7,17-dihydroxy-4Z,9,11,13Z,15E,19Z-docosahexaenoic acid reached a maximum during the initial phase of the inflammatory response, whereas the levels of 16-cysteinylglycinyl, 17-hydroxy-4Z,7Z,10,12,14,19Z-docosahexaenoic acid and 16-glutathionyl, 17-hydroxy-4Z,7Z, 10,12,14,19Z-docosahexaenoic acid were higher in exudates obtained 24 h after E. coli inoculation (FIG. 23D), which is within the resolution phase. These results demonstrate the presence of novel sulfido-conjugated DHA-derived products in infectious inflammatory exudates and their temporal regulation during self limited inflammation.

Having identified sulfido-conjugated molecules with mouse spleens and infectious exudates, for human translation, evidence was sought for these products with human spleens (see Table 2). LC-MS-MS analysis gave 3 distinct peaks with $T_R$ 8.0, 9.7, and 10.4 min (FIG. 24A). The parent ion for the product with $T_R$ 8.0 min gave an m/z of 666 and ions in the MS-MS spectrum with an m/z of 359 that are consistent with a DHA backbone carrying 2 hydroxy groups (FIG. 24B). In addition, the ions with m/z 537, 199, and 185 are consistent with alcohols at carbons 7 and 17 for the product under peak I. Whereas ions in the MS-MS from peak I with m/z 520 and 217 are consistent with a glutathionyl group on carbon 8, thus, the structure of the molecule was assigned as 8-glutathionyl, 7,17-dihydroxy-4Z,9,11,13Z, 15E,19Z-docosahexaenoic acid (FIG. 24B). The molecule with $T_R$ 9.7 min gave an MS-MS spectrum that was essentially the same as that of 16-glutathionyl, 17-hydroxy-4Z, 7Z,10,12,14,19Z-docosahexaenoic acid (FIG. 24C) and that with $T_R$ 10.4 min gave an MS-MS spectrum consistent with 16-cysteinyl, 17-hydroxy-4Z,7Z,10,12,14,19Z-docosahexaenoic acid (FIG. 24D).

TABLE 2

| Samples | Gender | Age (yrs) | Diagnosis |
|---|---|---|---|
| Human Autopsy Spleens | 2M 1F | 34-61 | 1/3 leukemia and sepsis 1/3 Heart failure and sepsis 1/3 Pneumonia and sepsis |
| Human Sepsis Plasma | 5F 5M | 57-96 | 1/10 *Salmonella* species 1/10 *Streptococcus pyogenes* 2/10 *Staphylococcus hominis* 3/10 *Corynebacterium* species 1/10 *S. infantarius* 1/10 *S. viridans* 1/10 *S. maltophilla* |

Identification of Sulfido-Conjugated Molecules with Human Leukocytes Human Macrophages Given the presence of a 17-hydroxy group in each of the molecules identified with mouse and human tissues (FIGS. 22, 23, and 24), the inventors assessed whether the 17-HpD was precursor in the biosynthesis of these novel molecules. Incubation of macrophages with serum-treated zymosan and 17-HpD gave 8-glutathionyl, 7,17-dihydroxy-4Z,9,11,13Z, 15E,19Z-docosahexaenoic acid (peak II), 16-cysteinylglycinyl, 17-dihydroxy-4Z,7Z,10,12,14,19Z-docosahexaenoic acid (peak III), 16-glutathionyl, 7-hydroxy-4Z,7Z,10,12,1, 4,19Z-docosahexaenoic acid (peak IV), and 16-cysteinyl, 17-hydroxy-4Z,7Z,10,12,14,19Z-docosahexaenoic acid (peak V; FIGS. 24A, B and FIG. 26). The parent ion for the product with $T_R$ 7.2 min (peak I) gave an m/z of 537 and ions in the MS-MS spectrum with an m/z of 359 that are consistent with a DHA backbone carrying 2 hydroxy groups (FIG. 26). In addition, ions with m/z 438, 393, and 143 are consistent with 2 alcohol groups at carbons 7 and 17 for the product beneath peak I. Whereas ions in the MS-MS from peak with m/z 247, 217, 203, 199, 185, and 179 are consistent with a cysteinylglycine group on carbon 8, thus, the structure of the molecule was assigned as 8-cysteinylglycinyl, 7,17-dihydroxy-4Z,9,11,13Z,15E,19Z-docosahexaenoic acid (FIG. 26).

Human PMN

Incubation of human neutrophils with serum-treated zymosan and 17-HpD also gave 5 distinct peaks with $T_R$s and MS-MS fragmentation spectra (FIGS. 25A, B, right panel) that were essentially the same as those found with human macrophages (FIG. 25A, left panel). Assessment of levels for each of the identified molecules in these incubations using MRM demonstrated that 16-glutathionyl, 17-hydroxy-4Z,7Z,10,12,14,19Z-docosahexaenoic acid and 8-cysteinylglycinyl, 7,17-dihydroxy-4Z,9,11,13Z,15E,19Z-docosahexaenoic acid were the more abundant molecules obtained from human neutrophils (FIG. 25C). Whereas, 16-cysteinylglycinyl, 17-hydroxy-4Z,77,10,12,14,19Z-docosahexaenoic acid and 8-glutathionyl, 7,17-dihydroxy-4Z, 9,11,13Z,25E,19Z-docosahexaenoic acid were the more abundant molecules identified with human macrophages. These results demonstrate that activated human PMNs and macrophages can convert 17-HpD to novel 17-series sulfido-conjugated products with each cell type giving characteristic sulfido-conjugated product profiles.

Physical Properties of Novel Sulfido-Conjugated Products

To obtain further evidence for the proposed structures, the inventors next investigated deuterium incorporation from $d_5$-DHA into each of the identified molecules. This gave the expected 5 Da shift in the parent ion of each of these products, where, for example, the m/z of 16-glutathionyl, 17-hydroxy-4Z,7Z,10,12,14,19Z-docosahexaenoic acid increased from 650 to 655, as did the m/z of diagnostic ions including that of the ion resulting from a carbon 16-17 break that increased from m/z 98 to 103 (Table 3) (14). The proposed structures were also investigated following diazomethane to obtain trimethyl and dimethyl derivatives of the parent molecules. Incubation of 8-glutathionyl, 7,17-dihydroxy-4Z,9,11,13Z,15E,19Z-docosahexaenoic acid with diazomethane led to an increase in the parent ion mass from m/z 666 to 708, indicating the addition of 3 methyl groups. In addition, characteristic ions including that resulting from a 7-8 carbon break increased from m/z 143 to 157. Similar results were also obtained for 16-cysteinylglycinyl, 17-hydroxy-4Z,7Z,10,12,14,19Z-docosahexaenoic acid, 16-cysteinyl, 17-hydroxy4Z,7Z,10,12,14,19Z-docosahexaenoic acid, 8-glutathionyl, 7,17-dihydroxy-4Z,9,11,13Z,15E,19Z-docosahexaenoic acid, and 8-cysteinylglycinyl 7,17-dihydroxy-4Z,9,11,13Z,15E,19Z-docosahexaenoic acid (Table 3).

TABLE 3

Biologic systems and physical properties of deuterium-labeled, di- and trimethyl ester derivatives of 17-series sulfido-conjugates

| Product | LC $T_R$ (min) | LC-MS-MS prominent ions | $d_5$-derivative prominent ions | Methyl-derivative prominent ions | UV $\lambda_{max}$ (nm)$^a$ | Tissue source |
|---|---|---|---|---|---|---|
| PCTR1 | 9.7 | 650 (M + H), 632, 614, 593, 575, 565, 548, 521, 503, 418, 400, 343, 325, 308, 275, 257, 245, 231, 213, 179, 162, 144, 129, 98 | 655 (M + H), 637, 619, 580, 526, 508, 423, 405, 348, 330, 308, 275, 257, 239, 239, 231, 227, 213, 179, 162, 144, 129, 103 | 692 (M + H), 674, 660, 656, 621, 549, 357 339, 336, 289, 259, 245, 193, 176 | 280 | Human macrophages Human PMN Human spleen Mouse infectious exudate Mouse spleen |

TABLE 3-continued

Biologic systems and physical properties of deuterium-labeled, di- and trimethyl ester derivatives of 17-series sulfido-conjugates

| Product | LC $T_R$ (min) | LC-MS-MS prominent ions | $d_5$-derivative prominent ions | Methyl-derivative prominent ions | UV $\lambda_{max}$ (nm)$^a$ | Tissue source |
|---|---|---|---|---|---|---|
| PCTR2 | 9.3 | 521 (M + H), 442, 343, 325, 275, 239, 231, 213, 201, 179, 162, 131 | 526 (M + H), 508, 482, 348, 330, 275, 257 | 549 (M + H), 531, 505, 478, 357, 289, 241, 193, 176 | 280 | Human macrophages Human PMN Mouse infectious exudate |
| PCTR3 | 10.4 | 464 (M + H), 446, 428, 365, 347, 343, 325, 275, 257, 239, 231, 227, 213, 121 | 469 (M + H), 451, 348, 275, 257, 245, 239, 231, 227, 213, | 492 (M + H), 474, 320, 289, 253, 245, 227, 135 | 280 | Human macrophages Human PMN Human spleen Human sepsis plasma Mouse spleen |
| RCTR1 | 8.0 | 666 (M + H), 648, 591, 537, 519, 416, 341, 323, 308, 247, 217, 211, 203, 199, 185, 179, 162, 143 | 671 (M + H), 653, 635, 578, 542, 524, 506, 439, 421, 403, 364, 346, 328, 308, 252, 234, 222, 216, 208, 204, 179, 143 | 708 (M + H), 690, 672, 610, 580, 565, 529, 355, 336, 217, 193, 185, 157 | 308 | Human macrophages Human PMN Human spleen Mouse infectious exudate |
| RCTR2 | 7.2 | 537 (M + H), 519, 501, 438, 393, 341, 247, 217, 211, 203, 199, 185, 179, 162, 143 | 542 (M + H), 524, 506, 469, 328, 252, 234, 222, 207, 190, 179 | 565 (M + H), 547, 529, 448, 373, 337, 211, 193, 185 | 308 | Human macrophages Mouse infectious exudate |

TABLE 3-continued

Biologic systems and physical properties of deuterium-labeled, di- and trimethyl ester derivatives of 17-series sulfido-conjugates

| Product | LC $T_R$ (min) | LC-MS-MS prominent ions | $d_5$-derivative prominent ions | Methyl-derivative prominent ions | UV $\lambda_{max}$ (nm)[a] | Tissue source |
|---|---|---|---|---|---|---|
| RCTR3 | 8.5 | 480, 462, 444, 412, 382, 359, 341, 323, 247, 217, 211, 199, 185, 121 | [b] | [b] | [b] | Human macrophages |

[a] $\lambda_{max}$ was determined using online UV-RP-HPLC (1100 Series) and a Poroshell 120 EC-C18 column (100 mm × 4.6 mm × 2.7 μm) with the mobile phase consisting of methanol:water 50:50 (vol:vol).
[b] Not determined.

Further evidence for each of the deduced structures was obtained by investigating the UV chromophore for each identified molecule. The inventors found that the chromophore for 8-glutathionyl, 7,17-dihydroxy-4Z,9,11,13Z,15E,19Z-docasahexaenoic acid gave triplet bands of absorption with $\lambda_{max}^{methonal/water}$ 308 nm, results were obtained with 8-cysteinylglycinyl, 7,17-dihydroxy-4Z,9,11,13Z,15E,19Z-docosahexaenoic acid (see Table 3). Assessment of the UV chromophores for 16-glutathionyl, 17-hydroxy-4Z,7Z,10,12,14,19Z-docosahexaenoic acid, 16-cysteinylglycinyl, 17-hydroxy-4Z,7Z,10,12,14,19Z-docosahexaenoic acid and 16-cysteinyl, 17-hydroxy-4Z,7Z,10,12,14,19Z-docosahexaenoic acid gave a triplet band of absorption with $\lambda_{max}^{methonal/water}$ 280 nm (Table 3).

Product-Precursor Relationships

To obtain further evidence for the biosynthetic pathways of these sulfido-conjugated mediators, the inventors investigated the product-precursor relationships for DHA with the novel molecules and human macrophages. DHA was rapidly converted to 16-glutathionyl, 17-hydroxy-4Z,7Z,10,12,14,19Z-docosahexaenoic acid that reached a maximum at 15 min (FIG. 27). The levels of 16-cysteinylglycinyl, 17-hydroxy-4Z,7Z,10,12,14,19Z-docosahexaenoic acid gradually increased, reaching a maximum at ~45 min. Levels for this product were maintained in these incubations over the subsequent 45 min, 16-cysteinyl, 17-hydroxy-4Z,7Z,10,12,14,19Z-docosahexaenoic acid also gradually increased over the course of the incubation, reaching a maximum at the 90 min interval (FIG. 27A).

Incubation of activated human macrophages with 17-HpD gave similar product-precursor relationships (FIG. 27B). In these incubations, also found was a rapid increase in 8-glutathionyl, 7,17-dihydroxy-4Z,9,11,13Z,15E,19Z-docosahexaenoic acid that reached an apparent maximum at ~15 min. Levels for 8-cysteinylglycinyl, 7,17-dihydroxy-4Z,9,11,13Z,15E,19Z-docosahexaenoic acid and 8-cysteinyl, 7,17-dihydroxy-4Z,9,11,13Z,15E,19Z-docosahexaenoic acid reached a maximum at later intervals (FIG. 27C). Of note, incubations with human macrophages, E. coli, and a GGT inhibitor (Acivicin), which inhibits LTD$_4$ formation (16), led to an increase in 16-glutathionyl, 17-hydroxy-4Z,7Z,10,12,14,19Z-docosahexaenoic acid in these incubations and a decrease in 16-cysteinyl, 17-hydroxy-4Z,7Z,10,12,14,19Z-docosahexaenoic acid (FIGS. 27D, E). Also found was a statistically significant increase in 8-glutathionyl, 7,17-dihydroxy-4Z,9,11,13Z,15E,19Z-docosahexaenoic acid and a decrease in 8-cysteinyl, 7,17-dihydroxy-4Z,9,11,13Z,15E,19Z-docosahexaenoic acid levels in activated macrophages incubated with Acivicin (FIG. 27F). These results provide evidence for product-precursor relationships in the biosynthesis of these sulfido-conjugates (vide infra).

Apoptotic Neutrophils Produce Endogenous 17-Series Sulfido-Conjugates and Stimulate the Phagocytosis and Clearance of Bacteria In Vivo The inventors next investigated the endogenous production of the novel sulfido-conjugates by apoptotic PMNs because they play key roles in signaling resolution during acute inflammation (8). Using LC-MS-MS-based metabololipidomics and matching $T_{RS}$ as well as MS-MS fragmentation spectra (see Table 3), identified in human apoptotic PMNs incubations were 8-cysteinylglycinyl, 7,17-dihydroxy-4Z,9,11,13Z,15E,19Z-docosahexaenoic acid (peak I), 16-glutathionyl, 17-hydroxy-4Z,7Z,10,12,14,19Z-docosahexaenoic acid (peak II), and 16-cysteinylglycinyl, 17-hydroxy-4Z,7Z,10,12,14,19Z-docosahexaenoic acid (peak III; FIG. 28A, B). MRM quantification of the identified sulfido-conjugated products demonstrated that 8-cysteinylglycinyl, 7,17-dihydroxy-4Z,9,11,13Z,15E,19Z-docosahexaenoic acid was the more abundant product produced by human apoptotic PMNs (FIG. 28C). In addition, administration of apoptotic neutrophils to mice 4 h after E. coli inoculation led to a significant increase in macrophage bacterial phagocytosis (FIG. 28D) and clearance in vivo (FIG. 28E).

Novel 17-Series Sulfido-Conjugates Accelerate Tissue Regeneration

The inventors next sought evidence for the biologic actions carried by the novel products. Given their temporal biosynthesis during resolution of self-limited inflammation (FIGS. 22 and 23) and production by human macrophages, assessed were the ability of these products to stimulate tissue regeneration. Here, a planaria tissue regeneration model was used (FIG. 29A). Planaria undergo both restorative and physiologic regeneration via evolutionarily conserved pathways making it an ideal system to test the tissue-regenerative actions of vertebrate-derived molecules (14, 18). Head resection gave a (maximum tissue regeneration) at 6 d and $T_{50}$ (the interval at which 50% regeneration occurred) ~4 d (FIG. 29A, B). Incubation of planaria with 16-glutathionyl, 17-hydroxy-4Z,7Z,10,12,14,19Z-docosahexaenoic acid and 16-cysteinylglycinyl, 17-hydroxy-4Z,7Z,10,12,14,19Z-docosahexaenoic acid gave an acceleration in tissue regeneration and a decrease in $T_{50}$ to ~3 d. Incubation of injured planaria with 8-glutathionyl, 7,17-dihydroxy-4Z,9,11,13Z,15E,19Z-docosahexaenoic acid and 8-cysteinylglycinyl, 7,17-dihydroxy-4Z,9,11,13Z,15E,19Z-docosahexaenoic acid (FIG. 29C) also led to an acceleration in tissue regeneration with a reduction in $T_{50}$ from ~4.5 to ~3.4 d.

Novel Sulfido-Conjugated Products are Both Anti-Inflammatory and Proresolving

Given the formation of these products in vivo during self-resolving infections, investigated next were actions of the new products on leukocytes at stimulating bacterial clearance. Incubation of 16-glutathionyl, 17-hydroxy-4Z,7Z,10,12,14,19Z-docosahexaenoic acid led to a dose-dependent increase in human macrophage phagocytosis of *E. coli*, actions that were comparable to those obtained with the proresolving mediator Protectin (D1) (10R,17S-dihydroxy-docosa-4Z,7Z,11E,13E,15Z,19Z-hexaenoic acid; PD1), also known as neuroprotectin D1 (FIG. 30A).

Phagolysosomal acidification is a critical step in the disposal of phagocytosed bacteria (19), so next investigated was whether 16-glutathionyl,17-hydroxy-4Z,7Z,10,12,14,19Z-docosahexaenoic acid promoted this process. Incubation of macrophages with 16-glutathionyl, 17-hydroxy-4Z,7Z,10,12,14,19Z-docosahexaenoic acid in the presence of bacteria led to a dose-dependent increase in macrophage phagolysosomal acidification (FIG. 30B and n=3; P<0.05).

Macrophage clearance of apoptotic cells and cellular debris is a key step in the resolution of inflammation (1, 8). Next investigated was whether 16-glutathionyl, 17-hydroxy-4Z,7Z,10,12,14,19Z-docosahexaenoic acid promoted macrophage clearance of apoptotic PMNs. Incubation of macrophages with this product led to a dose-dependent increase in the ability of human macrophages to uptake apoptotic human PMNs (FIG. 30C). Incubation of macrophages with 16-cysteinylglycinyl, 17-hydroxy-4Z,7Z,10,12,14,19Z-docosahexaenoic acid, 16-cysteinyl, 17-hydroxy-4Z,7Z,10,12,14,19Z-docosahexaenoic acid, 8-glutathionyl, 7,17-dihydroxy-4Z,9,11,13Z,15E,19Z-docosahexaenoic acid and 8-cysteinylglycinyl, 7,17-dihydroxy-4Z,9,11,13Z,15E,19Z-docosahexaenoic acid also led to a dose-dependent increase in human macrophage phagocytosis of *E. coli*, phagolysosomal acidification, and efferocytosis (FIG. 30). Taken together, these results indicate that the novel sulfido-containing products possess potent tissue-regenerative and proresolving actions.

For human translation, the inventors profiled plasma from patients diagnosed with sepsis (see Table 2 and 3) and compared levels of the new sulfido-conjugated molecules to those of MCTRs (14) as well as proinflammatory cysteinyl LTs (4, 9). LC-MS-MS-based LM metabololipidomics gave 16-cysteinyl, 17-hydroxy-4Z,7Z,10,12,14,19Z-docosahexaenoic acid, 13-glutathionyl, 14-hydroxy-4Z,7Z,9,11,16Z,19Z-docosahexaenoic acid (MCTR1), 13-cysteinylglycinyl, 14-hydroxy-4Z,7Z,9,11,16Z,19Z-docosahexaenoic acid (MCTR2), 13-cysteinyl,14-hydroxy-4Z,7Z,9,11,16Z,19Z-docosahexaenoic acid (MCTR3), and LTE4 (Table 3). MRM quantification demonstrated that MCTR3 was the more abundant sulfido-conjugated mediator identified in these plasma samples and was at levels comparable with those of $LTE_4$ (Table 4).

TABLE 4

SPM sulfido-conjugate levels in human and mouse tissues

| Product | 24 h Mouse infected spleens (pg/mg) | 24 h Resolving mouse exudates (pg/lavage) | Human autopsy spleen (pg/100 mg) | Human sepsis plasma (pg/ml) |
|---|---|---|---|---|
| PCTR1 | 19.4 ± 4.8 | 3.9 ± 2.6 | 83.1 ± 24.5 | a |
| PCTR2 | a | 3.4 ± 2.8 | a | a |
| PCTR3 | 23.3 ± 4.4 | a | 124.5 ± 51.7 | 1.5 ± 0.8 |
| RCTR1 | a | 5.8 ± 2.7 | 36.0 ± 11.2 | a |
| RCTR2 | a | a | a | a |
| RCTR3 | a | a | a | a |
| MCTR1 | 10.0 ± 4.1 | 1.8 ± 0.7 | 13.6 ± 5.7 | 3.1 ± 0.9 |
| MCTR2 | 22.2 ± 17.5 | 2.4 ± 1.1 | 22.9 ± 6.3 | a |
| MCTR3 | 53.0 ± 14.9 | 13.4 ± 3.7 | 33.1 ± 6.2 | 8.7 ± 2.5 |
| $LTC_4$ | 43.3 ± 15.4 | 8.3 ± 2.2 | 240.7 ± 73.5 | a |
| $LTD_4$ | a | 4.9 ± 1.3 | 49.3 ± 26.7 | a |
| $LTE_4$ | a | a | a | 12.9 ± 2.9 |
| | n − 3 mice | n − 6 mice | n − 3 patients | n − 10 patients |

Samples were extracted using solid-phase extraction columns with an automated extractor, and each was eluted with hexane, methylformate, and methanol. The methanol fractions were then taken from LC-MS-MS. Products were identified (see Materials and Methods) and quantified using MRM and calibration curves with an $r^2$ of 0.99. Results are the mean ± SEM. Lavage volume = 5 ml each mouse. "Below limits, ~1 pg.

In the present report, the inventors identified novel 17-series sulfido-containing molecules that were proresolving and tissue regenerative. These molecules were identified with human spleens and activated phagocytes as well as with mouse spleens and inflammatory exudates during *E. coli* peritonitis. They were produced via 17-lipoxygenation of DHA that was subsequently converted to monohydroxy or dihydroxy peptide conjugates. Incubation of these products with surgically injured planaria gave accelerated tissue regeneration. They also stimulated macrophage efferocytosis of apoptotic PMNs and phagocytosis of bacteria. Together, these results establish the structures of new 17-series sulfido-conjugates, their actions in tissue regeneration, and resolution of infections.

During infections, the host mounts a cellular response to contain and clear the invading pathogens (20). At the site of infection, neutrophils are the first responders, where they phagocytose and clear bacteria. Neutrophils also produce mediators in the resolution phase, including resolvins and protectins, that regulate macrophage responses (8, 20). Herein, identified with both healthy human neutrophils and apoptotic cells a novel family of sulfido-conjugated products (FIGS. 25 and 28). Their production was temporally regulated, possibly reflecting the temporal shift in leukocyte populations at the site of infections (11, 15). Human macrophages and PMNs were found to convert 17-HpD to sulfido-conjugates. Of note, specific product levels were found to differ between human apoptotic PMNs, healthy PMNs and macrophages, suggesting that the biosynthesis of these mediators is distinctly regulated in human leukocyte subtypes and during distinct stages of the inflammatory response (FIGS. 25 and 28).

The spleen plays a critical role in host response to both sterile and infectious challenges (8, 20). The 17-series sulfido-conjugates were identified during the course of self-limited infections in both mouse spleens and infectious exudates (FIGS. 22 and 23), suggesting a role for these products in regulating host responses to the invading pathogen at both the site of infections and in lymphoid tissues. These sulfido-conjugated molecules were also identified with human spleens (FIG. 24), suggesting that findings made with mice may also be relevant to humans.

LT-modifying agents have utility in select clinical conditions where the biology of the cysteinyl LTs, such as their regulation of smooth muscle contraction and amplification of the inflammatory response, is important (4, 21). FIG. 22, shows that levels of 17-series sulfido-conjugates were higher than those of arachidonic acid-derived cysteinyl LTs, indicating that their biosynthesis is distinctly regulated from those of the arachidonic acid-derived $LTC_4$, $LTD_4$, and $LTE_4$. This is in line with published findings demonstrating selective mobilization and utilization of DHA to produce proresolving mediators, namely RvD1, PD1, and 17-HD, that display potent host-protective actions in lymphoid organs (22, 23).

During self-limited inflammation, proresolving mediators ensure the activation of mechanisms that are key in preventing exuberant host responses, the clearance of offending pathogens, and the return to homeostasis (8). Accumulation of apoptotic cells at the site of inflammation can result in the release of intracellular material and amplification of the inflammatory response as the apoptotic cells progress to necrosis, a process also observed in trauma patients (20, 24). Thus, clearance of spent cells and other cellular debris is key in the resolution of inflammation and catabasis. The molecules identified herein were found to potently and dose-dependently promote human macrophage clearance of apoptotic cells (FIG. 30). In addition to clearing apoptotic cells, macrophages are also important in clearing invading pathogens. By comparison to PD1 and RvD2, the sulfido-conjugated products, at picomolar-to-nanomolar concentrations, increased uptake of E. coli in a dose-dependent manner. The actions of proresolving mediators on macrophages are characteristically bell-shaped dose responses (11, 14, 25). The results obtained herein with the sulfido-conjugated mediators also gave dose-dependent actions with features similar to those of a bell-shaped dose response (FIG. 30). Of note, maximal activity for increased E. coli phagocytosis by human macrophages was obtained at lower concentrations than with apoptotic cells. This suggests that these mediators may activate different intracellular pathways when promoting the phagocytosis of bacteria versus that of apoptotic cells. These sulfido-conjugated mediators were found to also increase phagolysosomal acidification during bacterial phagocytosis, which is a fundamental process in bacterial killing and clearance (20). In line with these findings, administration of human apoptotic neutrophils, found to carry the new sulfido-conjugated molecules, promoted macrophage phagocytosis and clearance of bacteria during E. coli infections in vivo (FIG. 28). Identification of these novel products in apoptotic cells at levels commensurate with their biologic actions (FIG. 30) suggests that they may exert a protective role when apoptotic PMNs are at sites of infections (FIG. 25).

Reestablishment of barrier function and repair of damaged tissues are critical in ensuring the return to homeostasis following both sterile and/or infectious injury (20). Planaria have emerged as a useful system to assess organ and tissue regeneration because these pathways are conserved throughout evolution (18). The inventors have recently identified a number of mediators that promote tissue regeneration in planaria (8, 14). MaR1 and RvE1 were the first mediators identified to promote tissue regeneration in these organisms (8). In a search to uncover mechanisms in tissue regeneration, the inventors recently identified a new family of mediators, coined MCTR. MCTRs are produced by regenerating planaria as well as in human milk and resolving infectious exudates, and promote tissue regeneration (14). Acceleration of tissue regeneration in planaria was also obtained with 16-glutathionyl, 17-hydroxy-4Z,7Z,10,12,14,19Z-docosahexaenoic acid and 16-cysteinylglycinyl, 17-hydroxy-4Z,7Z,10,12,14,19Z-docosahexaenoic acid or with 8-glutathionyl, 7,17-dihydroxy-4Z,9,11,13Z,15E,19Z-docosahexaenoic acid and 8-cysteinylglycinyl, 7,17-dihydroxy-4Z,9,11,13Z,15E,19Z-docosahexaenoic acid. These findings indicate that these sulfido-conjugated mediators may he shared signals in controlling the complex processes involved in resolution of inflammation, tissue regeneration, and the return to homeostasis. These results also highlight the primordial origins of local acting mediators, including resolvins, protectins, and MCTRs. Indeed, these ω-3 mediators have now been identified in a number of species ranging from planaria, to Peruvian anchovies, salmon, mice, and humans (8, 14, 26).

LM biosynthesis involves stereospecific enzymatic conversion of precursor fatty acids (1). DHA is precursor to 17-series sulfido-conjugates because incubation of deuterium-labeled DHA with mouse spleens gave products with the expected 5 Da shift in their m/z ratio (Table 3). Human macrophages and PMNs incubated with DHA also gave 17-series sulfido-conjugates (n=3), and assessment of apoptotic PMN product profiles demonstrated that these cells converted endogenous DHA to these molecules.

The biosynthetic pathways for the novel sulfido-conjugated products are proposed in FIG. 31. This takes into account results from the present analysis with the mechanisms proposed for the biosynthesis of MCTR (14), protectins, and D-series resolvins (10), and the arachidonate pathway including cysteinyl LTs (27, 28). In this proposed scheme, DHA is first converted via 17-lipoxygenation to 17-HpD. This intermediate can undergo a second lipoxygenation at the carbon 7 position yielding 7S,17S-dihydro (peroxy)-4Z,8E,10Z,13Z,15E,19Z-docosahexaenoic acid. This product can then be enzymatically converted to an allylic epoxide that is in turn enzymatically converted to 8-glutathionyl, 7,17-dihydroxy-4Z,9,11,13Z,15E,19Z-docosahexaenoic acide. The addition of glutathione to an allylic epoxide is governed by glutathione S-transferase enzymes in the biosynthesis of MGM (14) and cysteinyl LTs (4, 6). This 8-glutathionyl, 7,17-dihydroxy-4Z,9,11,13Z,15Z,19Z-docosahexaenoic acid can then be converted by GGTs to 8-cysteinylglycinyl, 7,17-dihydroxy-4Z,9,11,13Z,15E,19Z-docosahexaenoic acid and subsequently to 8-cysteinyl, 7,17-dihydroxy-4Z,9,11,13Z,15E,19Z-docosahexaenoic acid.

The 17-HpD is also enzymatically converted to a 16(17)-epoxide intermediate (29) then to 16-glutathionyl, 17-hydroxy-4Z,7Z,10,12,14,19Z-docosahexaenoic acid, GGT enzymes then convert this product to 16-cysteinylglycinyl, 17-hydroxy-4Z,7Z,10,12,14,19Z-docosahexaenoic acid and then to 16-cysteinyl, 17-hydroxy-4Z,7Z,10,12,14,19Z-docosahexaenoic acid. The interrelationships between products carrying glutathionyl, cysteinylglycinyl, and cysteinyl in the proposed biosynthetic pathways are also supported by product-precursor relationships obtained with DHA, 17-HpD, a GGT inhibitor, and human macrophages (FIG. 27). Of note, because mammalian lipoxygenases insert molecular oxygen predominantly in the S-stereochemistry, it is proposed that the stereochemistry for the hydroxy groups at the 7 and 17 positions is retained in the biosynthesis of the novel products. It is conceivable that the R-containing diastereomers of these products may also be of biologic relevance in the resolution of inflammation and tissue regeneration. In addition, given that glutathione S-transferase enzymes in the biosynthesis of cysteinyl LTs stereoselectively add glutathione to the ally tic epoxide in an R configuration in the carbon 6 position of arachidonate (6, 30), it is likely that the stereochemistry at carbon 8 and 16 in the new pathways (FIG. 31) is retained in the R configuration.

The inventors coin the tetraene-containing molecules as resolvin conjugate in tissue regeneration (RCTR; FIG. 31) because they display potent tissue-regenerative actions and share their biosynthetic pathway, structural features, as well as proresolving actions with the D-series resolvins (8, 10)). Similarly, the triene-containing molecules are referred to herein as protectin conjugate in tissue regeneration (PCTR) because they share biosynthetic pathway, structural features, and biologic actions with the DHA-derived protectins as well as display potent tissue-regenerative actions. Together, these results demonstrate that ω-3 EFAs can be converted via subsequent lipoxygenase activity to an allylic epoxide intermediate. This intermediate is in turn converted to potent bioactive signaling molecules via either enzymatic hydrolysis (8) or conjugation.

In summation, using key bioactions in resolution and tissue regeneration as well as LC-MS-MS-based LM metabololipidomics, elucidation of the structure of 2 novel bioactive families of 17-series sulfido-conjugates was carried out. These products displayed host-protective, proresolving, and tissue-regenerative actions in both vertebrates and invertebrates as repairers. Specifically, the new peptide-containing molecules promoted phagocytosis of bacteria and efferocytosis of apoptotic cells by macrophages, were present in human sepsis, and accelerated tissue regeneration in planaria. In 1930, EFA deficiencies were shown to result in uncontrolled infections and death (31). Elucidation of these mediators and pathways as well as the determination of their potent bioactions (FIG. 31) provide mechanistic evidence for the host-protective actions for the precursor DHA. In addition, these findings expand the scope and biologic roles for peptide LMs and afford signals in the regulation of host responses to infections and tissue injury.

In summary, using a systematic approach, the inventors identified conserved chemical signals from planaria, mice and human tissues that are anti-inflammatory, proresolving and tissue regenerative. These new peptide-lipid conjugate molecules accelerate resolution of E. coli infection, stimulate phagocytic functions, tissue regeneration in planaria and tissue repair in mice, thereby fulfilling criteria as immunoresolvents, namely agents that stimulate resolution of inflammation (12). The proposed biosynthesis of these mediators occurs via lipoxygenation of DHA, producing 14-hydro (peroxy)-docosahexaenoic acid and an epoxide intermediate (FIG. 19) that is converted to SC. This step in planaria relies on GST enzyme(s), giving 13-glutathionyl,14-hydroxy-docosahexaenoic acid (SCI) and 13-cysteinylglycinyl, 14-hydroxy-docosahexaenoic acid (SCII; FIG. 12), and opens the characterization of other peptide-lipid conjugates in the SPM genus. Along these lines FIG. 20 illustrates the identification of key sulfido conjugates from the protectin (left panels) and D-series resolvin (right panels) pathways. These findings also suggest EPA from the 5(6) epoxide intermediate and other n-3 essential fatty acids are converted to bioactive conjugates. Compounds identified in D-series resolvins and E-series resolvins are shown in FIG. 32 while compounds of the protectin biosynthetic pathway are shown in FIG. 33. Members of these pathways may also be converted to bioactive conjugates. The families of these potential candidates are illustrated schematically in FIG. 34.

As discussed above, members of the disclosed family of oxylipin conjugates include but are not limited to docosapentaenoic acid (C22:5n-6) (DPAn-6) and its isomer DPAn-3, docosatetraenoic acid (C-22:4n-6)(DTAn-6); docosahexaenoic acid (C-22:6n-3) (DHA); eicosapentaenoic acid (C20:5n-3)(EPA); and arachidonic acid (C20:4n-6),

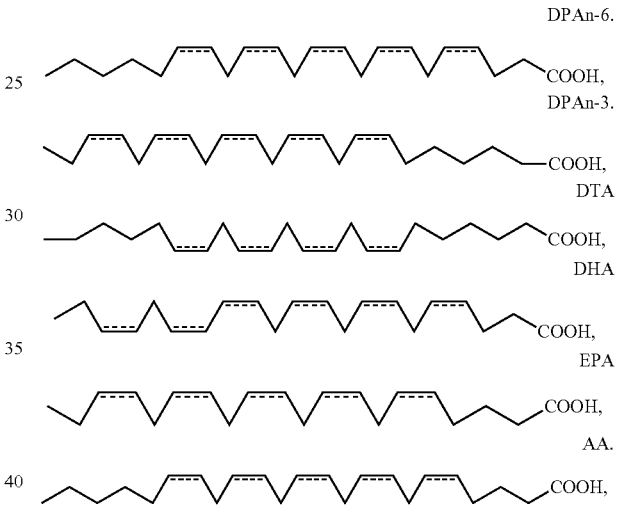

As discussed above and illustrated in FIGS. 31-34, various SPM are synthesized from the oxlipin precursors shown above. Without being held to any theory, it is thought the auxochrome conjugation of the amino acid or peptide moiety is conjugated to the oxylipin at the site of attack of a double bond during oxygenation. Thus, the identification of bioactive oxylipins may provide a useful reservoir of SPM's from which to identify further bioactive conjugates.

The synthesis of stable mimetics will provide tools for investigating pro-resolving anti-inflammatory pathways and tissue regeneration as well as the potential tier new therapeutics (see FIG. 34). The specific peptide-lipid conjugates, identified herein as SCI and SCII (FIG. 19)(corresponding to MCTR1 and MCTR2), carry a carbon-14-position alcohol and are biosynthesized via the maresin-epoxide intermediate; thus, they belong to the maresin (macrophage mediators in resolving inflammation) family (19). Given that these previously undescribed signals regulate the cardinal signs of resolution; i.e. clearance of debris and infections by phagocytes, tissue regeneration and regulation of pro-inflammatory chemical mediators, the inventors coin these SC molecules as maresin conjugates in tissue regeneration (MCTR). Together these findings provide new signals and pathways in host responses to injury, acute inflammation and infectious exudates that are resolution moduli promoting homeostasis.

The following paragraphs enumerated consecutively from 1 through 51 provide for various additional aspects of the present invention. In one embodiment, in a first paragraph:

1. A purified compound comprising:
an oxylipin or oxylipin derivative conjugated by an auxochrome to an amino acid or peptide derivative or a pharmaceutically acceptable salt of the compound.

2. The purified compound of paragraph 1, wherein the oxilipin is derived from eicosapentaenoic acid, docosahexaenoic acid, docosapentaenoic acid, docosatetraenoic acid or arachidonic acid.

3. The purified compound of paragraphs 1 and 2, wherein the auxochrome is: S, NH, $CH_2$, or O.

4. The purified compound of paragraphs 1 through 3, wherein the amino acid or peptide derivative is: glutathione, cysteine, methoionine, glycine, homocysteine, taurine, S-adenosylmethionine, 5. The purified compound of paragraphs 1 through 4, having the general formula 1-X:

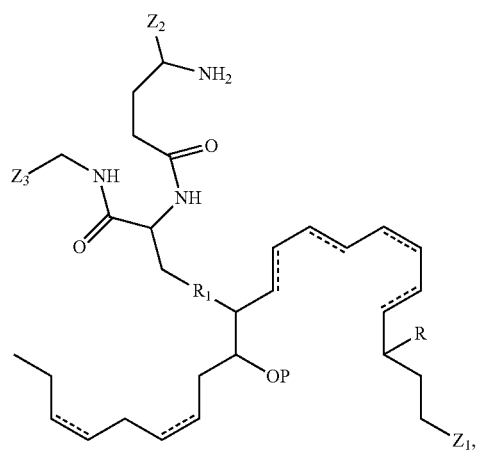

(I)

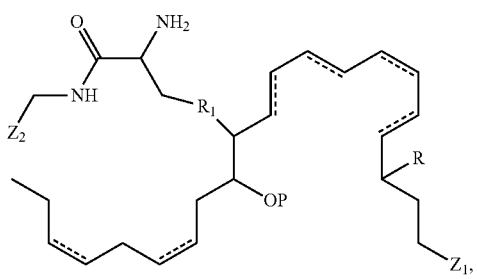

(II)

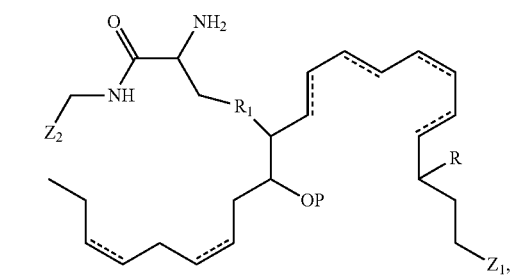

(III)

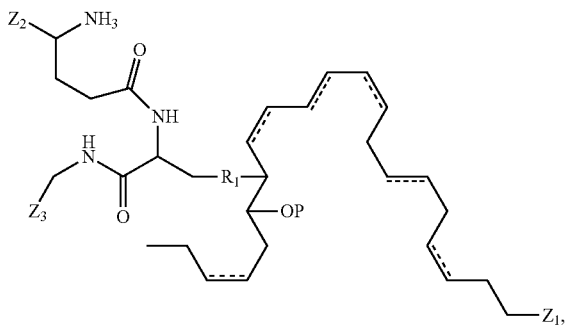

(IV)

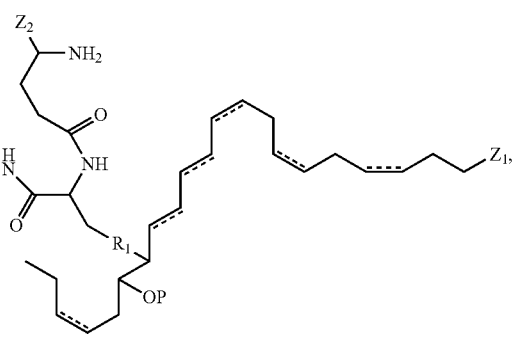

(V)

(VI)

(VII)

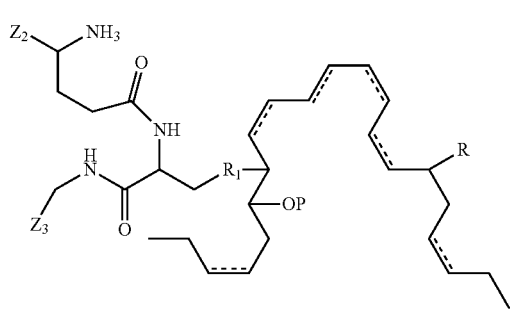

-continued

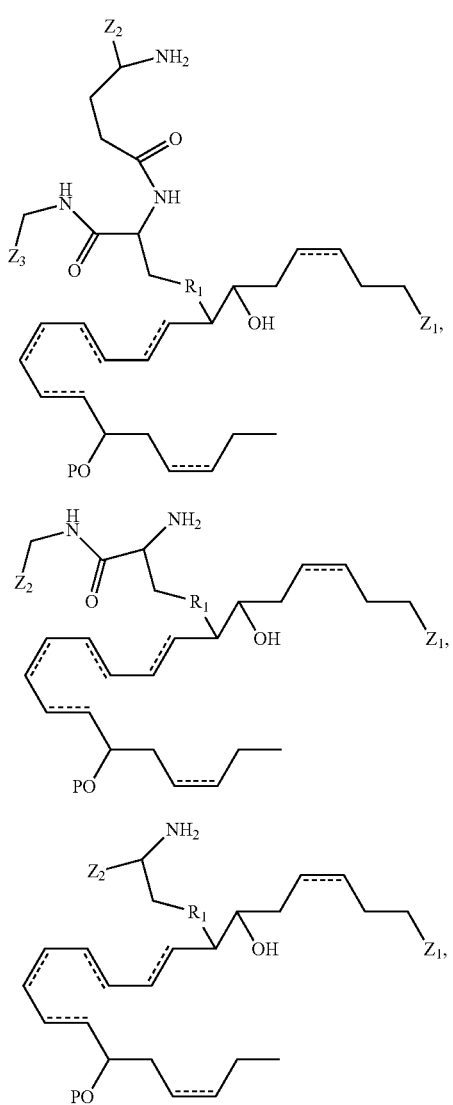

wherein each P individually is a protecting group or a hydrogen atom;

wherein ══ is a double bond;

wherein each double bond is independently in the E or Z configuration;

wherein $Z_1$, $Z_2$ and $Z_3$, when present, individually is $C(O)OR^d$, —$C(O)NR^cR^c$, —C(O)H, —$C(NH)NR^cR^c$, —C(S)H, —C(S)ORd, —$C(S)NR^cR^c$, or —CN; each $R^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each $R^c$, is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^b$ is independently selected from =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^d$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ or —$[NR^aC(NR^a)]_nNR^cR^c$;

each n, independently is an integer from 0 to 3; and each $R^d$, independently is a protecting group or $R^a$;

wherein R, when present, is independently selected from hydrogen, hydroxyl, (C1-C6)alkyl, (C3-C8), cyclohexyl, (C4-C11)cycloalkylalkyl, (C5-C10)aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

wherein $R^1$ is independently selected from: S, NH, $CH_2$, or O;

or a pharmaceutically acceptable salt or ester thereof.

6. The purified compound of paragraphs 1 through 5, wherein the compound has the general structure of formula XI-XX:

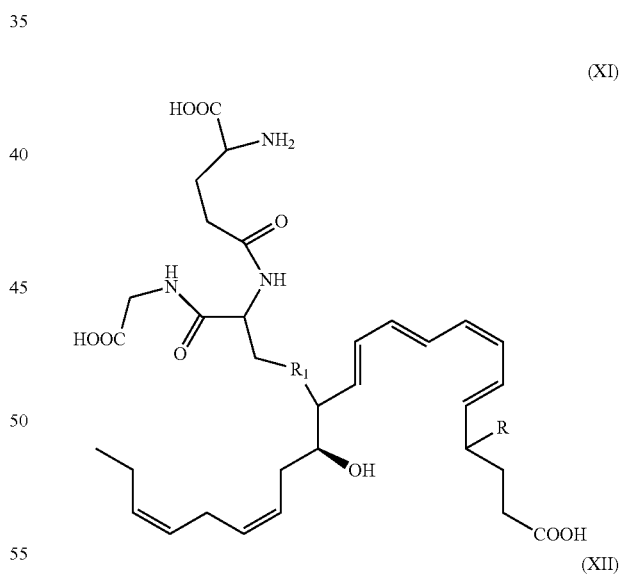

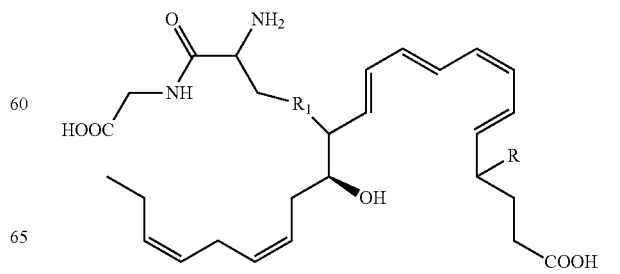

(XIII)
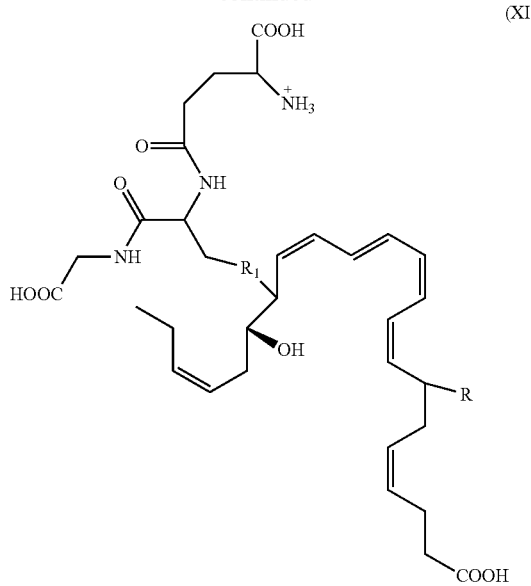
(XVI)
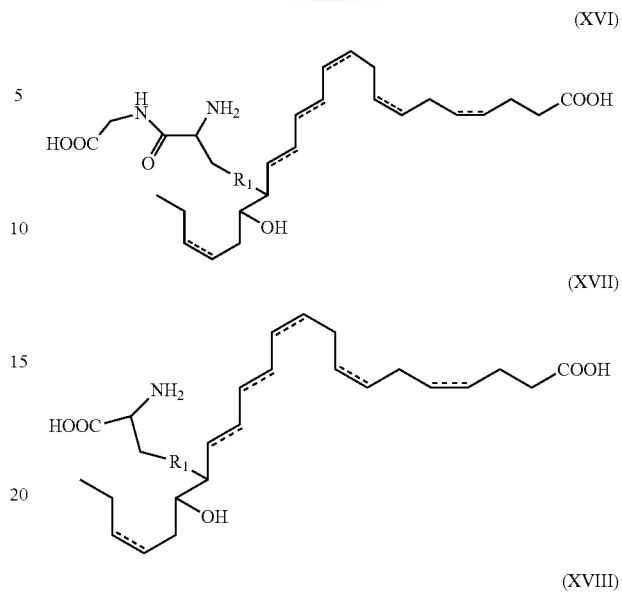
(XVII)
(XVIII)
(XIV)
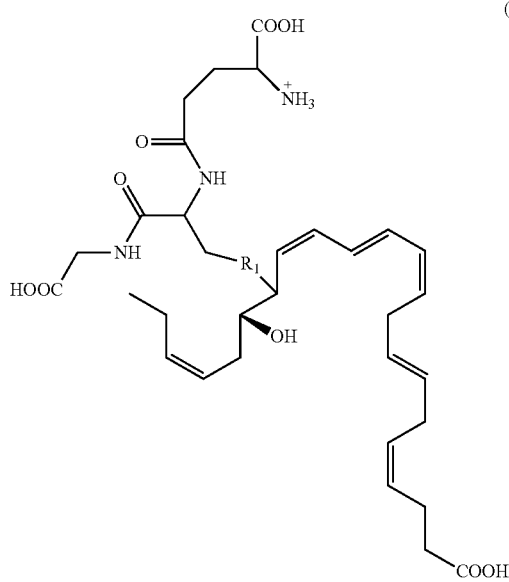
(XIX)
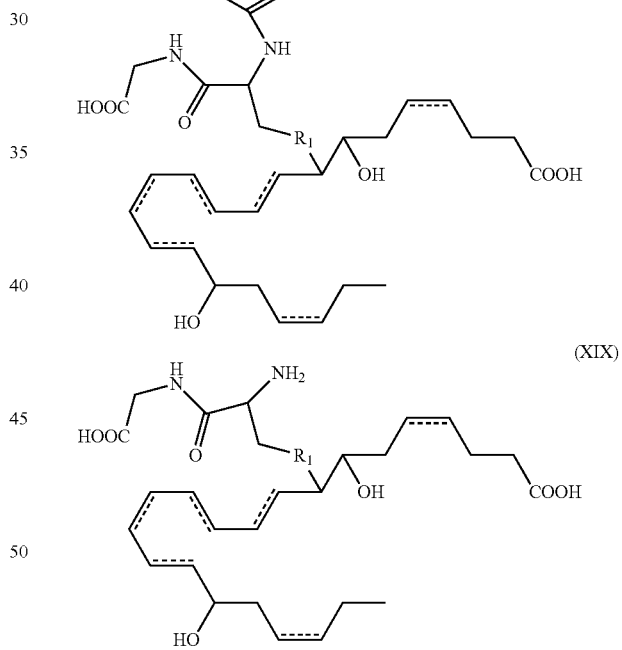
(XV)
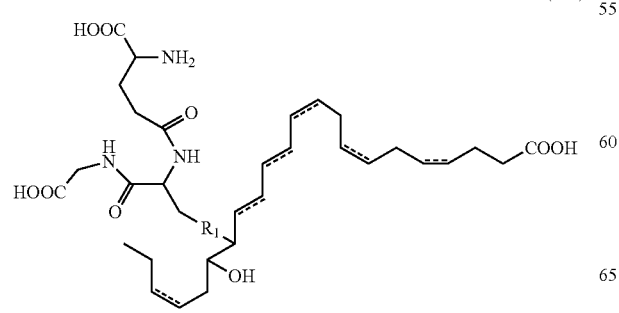
(XX)
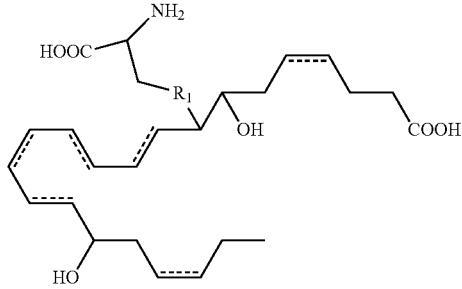

wherein R, when present, is independently selected from hydrogen, hydroxyl, (C1-C6)alkyl, (C3-C8), cyclohexyl, (C4-C11)cycloalkylalkyl, (C5-C10)aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl 4-11 membered cycloheteroalkylalkyl, 5-10 membered heteroaryl or 6-16 membered heteroarylalkyl;

wherein $R_1$ is independently selected from: S, NH, $CH_2$, or O;

or a pharmaceutically acceptable salt or ester thereof.

7. The purified compound of paragraphs 1 through 6, wherein the compound is:

13-glutathionyl, 14-hydroxy-docosahexaenoic acid; 13-cysteinylglycinyl, 14-hydroxy-docosahexaenoic acid; 13-cysteinyl, 14-hydroxy-docosahexaenoic acid; 17-hydroxy, 16-glutathionyldocosahexaenoic acid, 17-hydroxy, 16-cysteinylglycinyl docosahexaenoic acid; 17-hydroxy, 16-cysteinyl docosahexaenoic acid; 7,17-hydroxy, 8-glutathionyl docosahexaenoic acid; 7,17-hydroxy, 8-cysteinylglycinyl docosahexaenoic acid; and 7,17-hydroxy, 8-cysteinyl docosahexaenoic acid; and pharmaceutically acceptable salts or esters thereof.

8. A composition comprising the compound of any of the preceding paragraphs and a pharmaceutically acceptable carrier.

9. A method of treating inflammation or an inflammatory disease comprising administering to a subject in need thereof a compound or composition according to any of paragraphs 1-8.

11. A method for enhancing tissue regeneration comprising, administering to a subject in need thereof a compound or composition according to any of paragraphs 1-8.

12. A method for treating, ameliorating and resolving an infection comprising, administering to a subject in need thereof a compound or composition according to any of paragraphs 1-8.

13. A method of treating, limiting or preventing second organ reflow and ischemia/reperfusion injury comprising administering to a subject in need thereof a compound or composition according to any of paragraphs 1-8.

14. A method of promoting tissue repair or regeneration in a subject in need thereof comprising, administering a compound or composition of any of paragraphs 1-8.

15. A method of stimulating macrophage phagocytosis in a subject in need thereof comprising, administering a compound or composition according to any of paragraphs 1-8.

16. A method of promoting tissue repair in a subject in need thereof comprising, administering a compound or composition according to any of paragraphs 1-8.

17. A method of reducing pro-inflammatory eicosanoids systemically in a subject in need thereof comprising administering a compound or composition according to paragraphs 1-8.

18. A method of protecting, limiting or inhibiting neutrophil mediated tissue damage comprising, administering to a subject in need thereof a compound or composition according to any of paragraphs 1-8.

19. A method of stimulating the production of reactive oxygen species in macrophage and neutrophils comprising administering to a subject in need thereof a compound or composition according to any of paragraphs 1-8.

20. A method of decreasing or limiting leukocyte migration into tissues in a subject in need thereof comprising, administering a compound or composition according to any of paragraphs 1-8.

21. A method of stimulating efferocytosis comprising, administering to a subject in need thereof an effective amount of a compound or composition according to any of paragraphs 1-8.

As described herein, various exemplary embodiments of compounds, compositions and methods according to this invention can be used prophylactically to treat individuals that suffer with inflammation or are at risk of suffering from an inflammatory response or disease associated with inflammation or an inflammatory response. In addition, various exemplary embodiments of methods according to this invention can be used prophylactically to inhibit inflammation and/or to avoid the risks associated with infection and inflammation, such as, but not limited to cardiovascular diseases, cancer, diabetes, asthma, tissue regeneration and the like.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Nathan C (2012) Fresh approaches to anti-infective therapies. *Sci. Transl. Med.* 4(140):140sr142.
2. Ward P A (2012) New approaches to the study of sepsis. *EMBO molecular medicine* 4(12):1234-1243,
3. Serhan C N & Savill J (2005) Resolution of inflammation: the beginning programs the end. *Nat. Immunol.* 6:1191-1197.
4. Bannenberg G L, Aliberti J, Hong S, Sher A, & Serhan C N (2004) Exogenous pathogen and plant 15-lipoxygenase initiate endogenous lipoxin $A_4$ biosynthesis. *J. Exp. Tied.* 199:515-523.
5. Nakamura M & Shimizu T ('2011) Leukotriene receptors. *Chem. Rev.* 111(10):6231-6298.
6. Samuelsson B (2012) Role of basic science in the development of new medicines: examples from the eicosanoid field. *J. Biol. Chem.* 287:10070-10080.
7. Fullerton J N, O'Brien A J, & Gilroy D W (2014) Lipid mediators in immune dysfunction after severe inflammation. *Trends in immunology* 35:12-21.
8. Tabas I & Glass C K (2013) Anti-inflammatory therapy in chronic disease: challenges and opportunities. *Science* 339(6116):166-172.
9. Serhan C N (2014) Pro-resolving lipid mediators are leads for resolution physiology. *Nature* 510(7503):92-101.
10. Haeggstrom J Z & Funk C D (2011) Lipoxygenase and leukotriene pathways: biochemistry, biology, and roles in disease. *Chem. Rev.* 111(10):5866-5898.
11. Chiang N, et al. (2012) Infection regulates pro-resolving mediators that lower antibiotic requirements. *Nature* 484 (7395):524-528.
12. Serhan C N, et al. (2012) Macrophage proresolving mediator maresin 1 stimulates tissue regeneration and controls pain. *FASEB journal official publication of the Federation of American Societies for Experimental Biology* 26(4):1755-1765.

13. Serhan C N, et al, (2009) Maresins: novel macrophage mediators with potent antiinflammatory and proresolving actions. *The Journal of experimental medicine* 206(1):15-23.
14. Sanchez Alvarado A (2006) Planarian regeneration: its end is its beginning. *Cell* 124(2):241-245.
15. Calder P C, et al. (2006) Early nutrition and immunity—progress and perspectives. *Br. J. Nutr.* 96(4):774-790.
16. Umesono Y, et al. (2013) The molecular logic for planarian regeneration along the anterior-posterior axis. *Nature* 500(7460):73-76.
17. Gordon S & Mantovani A (2011) Diversity and plasticity of mononuclear phagocytes. *Eur. J. Immunol.* 41(9):2470-2472.
18. Stables M J, et al, (2011) Transcriptomic analyses of murine resolution-phase macrophages. *Blood* 118(26):e192-208.
19. Serhan C N, et al. (2009) Maresins: novel macrophage mediators with potent anti-inflammatory and pro-resolving actions. *J. Exp. Med,* 206:15-23.
20. Deng B, et al. (2014) Maresin biosynthesis and identification of maresin 2, a new anti-inflammatory and pro-resolving mediator from human macrophages. *PloS one* 9(7):e102362.
21. Dalli J. et al. (2013) The novel 13S,14S-epoxy-maresin is converted by human macrophages to maresin1 (MaR1), inhibits leukotriene A4 hydrolase (LTA4H), and shifts macrophage phenotype. *FASEB J* 27:2573-2583.
22. Samuelsson B (1983) Leukotrienes: mediators of immediate hypersensitivity reactions and inflammation. *Science* 220(4597):568-575.
23. Martinez Molina D, et al. (2007) Structural basis for synthesis of inflammatory mediators by human leukotriene C4 synthase. *Nature* 448(7153):613-616.
24. Outing L, Bernstrom K, & Hammarstrom S (1981) Formation of leukotrienes E4 and E5 in rat basophilic leukemia cells. *European journal of biochemistry/FEBS* 120(1):41-45.
25. Majno G & Joris I (2004) *Cells, Tissues, and Disease: Principles of General Pathology* (Oxford University Press, New York) 2nd Ed p 1005.
26. Pipparelli A, et al. (2013) ROCK inhibitor enhances adhesion and wound healing of human corneal endothelial cells. *PloS one* 8(4):e62095.
27. Sato T & Clevers H (2013) Growing self-organizing mini-guts from a single intestinal stem cell: mechanism and applications. *Science* 340(6137):1190-1194.
28. Rouhana L, et al. (2013) RNA interference by feeding in vitro-synthesized double-stranded RNA to planarians: methodology and dynamics. *Dev. Dyn.* 242(6):718-730.
29. King R S & Newmark P A (2013) In situ hybridization protocol for enhanced detection of gene expression in the planarian Schmidtea mediterranea. *BMC Dev. Biol.* 13:8.
30. Dalli J & Serhan C N (2012) Specific lipid mediator signatures of human phagocytes: microparticles stimulate macrophage efferocytosis and pro-resolving mediators. *Blood* 120(15):e60-72.

---

What is claimed is:
1. A purified compound comprising one of the formulas as followed:
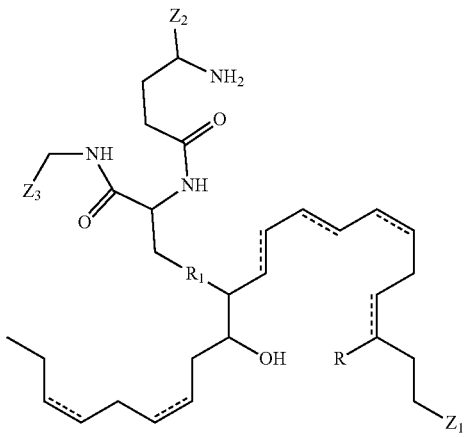
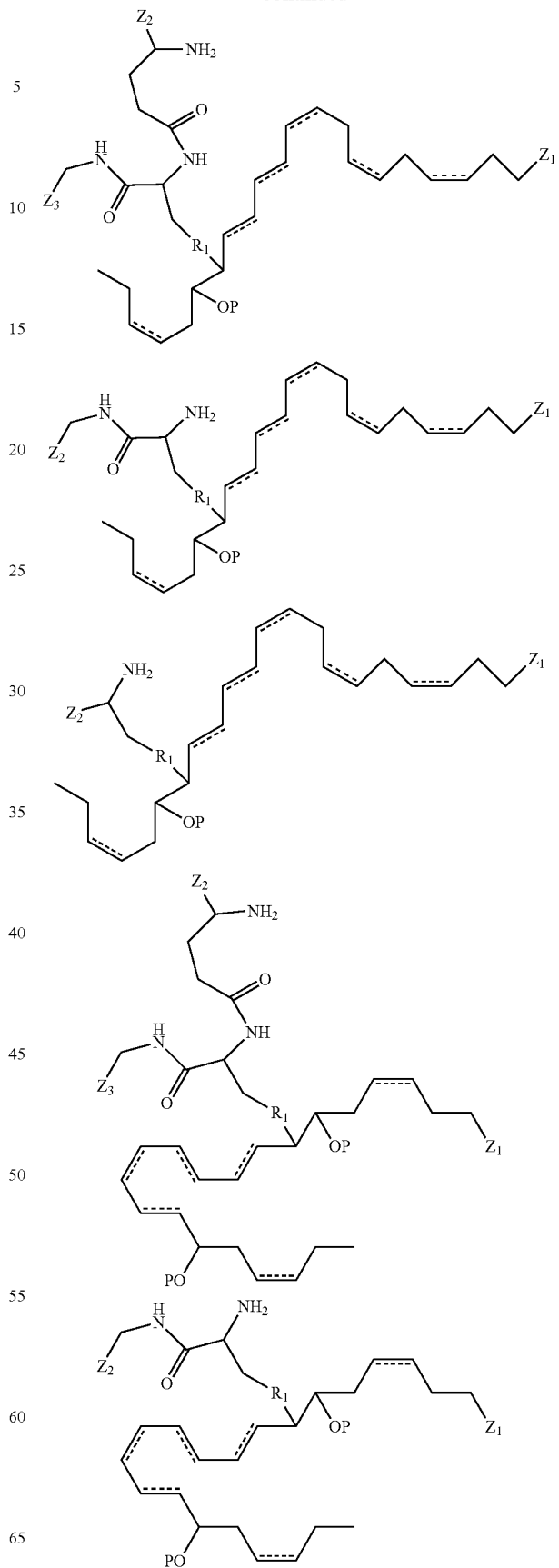

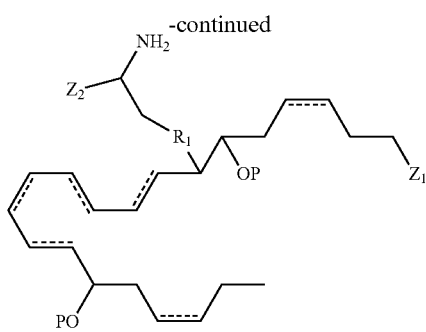

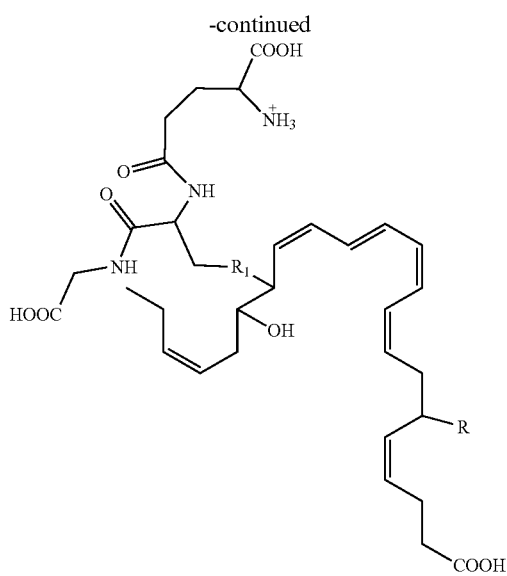

wherein each P individually is a protecting group or a hydrogen atom;

wherein ═══ is a double bond;

wherein each double bond is independently in the E or Z configuration;

wherein $Z_1$, $Z_2$ and $Z_3$, when present, individually is $C(O)OR^d$, or —C(O)H, each $R^a$, is independently selected from hydrogen, and $(C_1-C_6)$ alkyl; and each $R^d$, independently is a protecting group or $R^a$;

wherein R, when present, is independently selected from hydrogen, hydroxyl, and $(C_1-C_6)$ alkyl;

wherein $R_1$ is independently selected from: S, NH, $CH_2$, or O;

or a pharmaceutically acceptable salt or ester thereof.

2. The purified compound of claim 1, wherein the compound has the general structure of formula as followed:

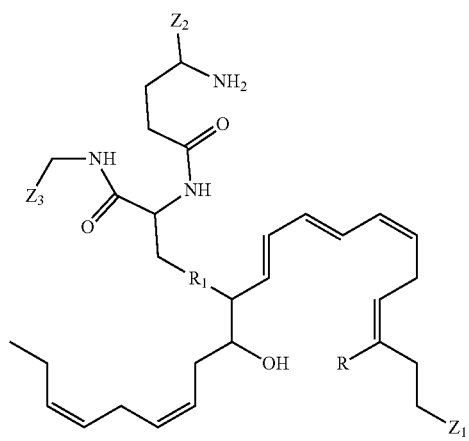

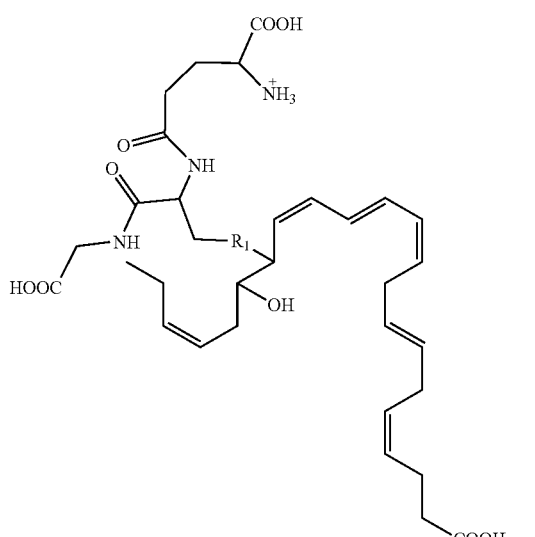

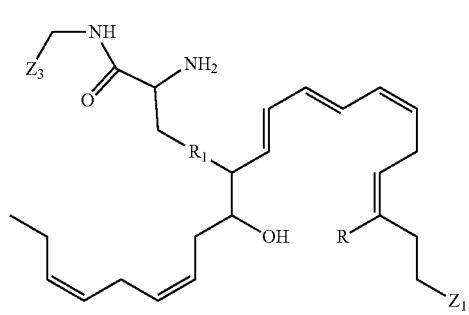

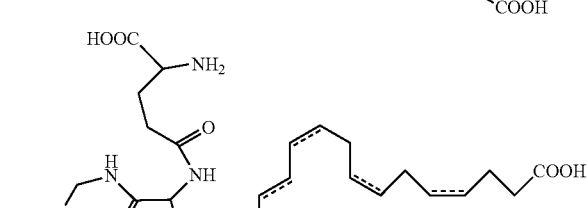

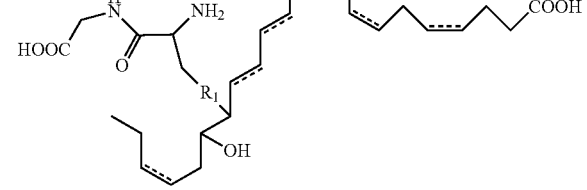

-continued

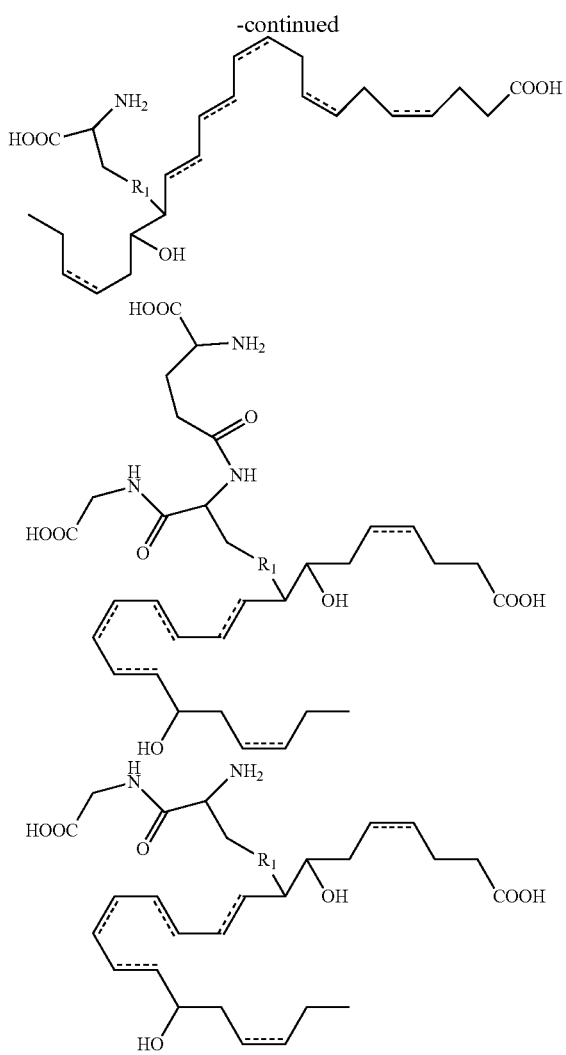

-continued

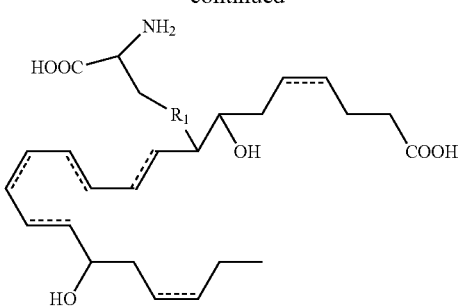

wherein R, when present, is independently selected from hydrogen, hydroxyl, and $(C_1\text{-}C_6)$ alkyl;

wherein $R_1$ is independently selected from: S, NH, $CH_2$, or O;

or a pharmaceutically acceptable salt or ester thereof.

3. A purified compound, wherein the compound is: 13-glutathionyl-14-hydroxy-docosahexaenoic acid; 13-cysteinylglycinyl-14-hydroxy-docosahexaenoic acid; 13-cysteinyl-14-hydroxy-docosahexaenoic acid; 7,17-dihydroxy-16-glutathionyl-docosahexaenoic acid; 17-hydroxy-16-glutathionyldocosahexaenoic acid; 17-hydroxy-16-cysteinylglycinyl docosahexaenoic acid; 17-hydroxy-16-cysteinyl docosahexaenoic acid; 7, 17-dihydroxy-8-glutathionyl docosahexaenoic acid; 7, 17-dihydroxy-8-cysteinylglycinyl docosahexaenoic acid; and 7, 17-dihydroxy-8-cysteinyl docosahexaenoic acid; and pharmaceutically acceptable salts or esters thereof.

4. A composition comprising the compound of claim 1 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 11,135,228 B2 | |
| APPLICATION NO. | : 15/517016 | |
| DATED | : October 5, 2021 | |
| INVENTOR(S) | : Charles N. Serhan, Jesmond P. Dalli and Nan Chiang | |

It is certified that error appears in the above-identified patent and that said Letters Patent is hereby corrected as shown below:

In the Specification

STATEMENT REGARDING FEDERALLY SPONSORED RESEARCH Should read:
The work leading to this invention was supported, in part, by National Institutes of Health (NIH) grant GM095467. The United States Government may have certain rights in this invention.

Signed and Sealed this
Twelfth Day of July, 2022

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 24
<212> TYPE: DNA
<213> ORGANISM: artificial
<220> FEATURE:
<223> OTHER INFORMATION: forward primer

<400> SEQUENCE: 1
accaccaact gtttagctcc ctta                                    24

<210> SEQ ID NO 2
<211> LENGTH: 24
<212> TYPE: DNA
<213> ORGANISM: artificial
<220> FEATURE:
<223> OTHER INFORMATION: PCR primer

<400> SEQUENCE: 2
gatggtccat caacagtctt ttgc                                    24

<210> SEQ ID NO 3
<211> LENGTH: 21
<212> TYPE: DNA
<213> ORGANISM: artificial
<220> FEATURE:
<223> OTHER INFORMATION: PCR primer

<400> SEQUENCE: 3
ttgctctctt tacgctccgg t                                       21

<210> SEQ ID NO 4
<211> LENGTH: 20
<212> TYPE: DNA
```

```
<213> ORGANISM: artificial
<220> FEATURE:
<223> OTHER INFORMATION: PCR primer

<400> SEQUENCE: 4
cgcatagttc cctgcatggt                                               20

<210> SEQ ID NO 5
<211> LENGTH: 24
<212> TYPE: DNA
<213> ORGANISM: artificial
<220> FEATURE:
<223> OTHER INFORMATION: PCR primer

<400> SEQUENCE: 5
tcacaaactc caccgcagta cttt                                          24

<210> SEQ ID NO 6
<211> LENGTH: 27
<212> TYPE: DNA
<213> ORGANISM: artificial
<220> FEATURE:
<223> OTHER INFORMATION: PCR primer

<400> SEQUENCE: 6
ggtatggatt agcattattg aattgtg                                       27

<210> SEQ ID NO 7
<211> LENGTH: 27
<212> TYPE: DNA
<213> ORGANISM: artificial
<220> FEATURE:
<223> OTHER INFORMATION: PCR primer

<400> SEQUENCE: 7
cactgatatc tacttcacga aagccag                                       27

<210> SEQ ID NO 8
<211> LENGTH: 25
<212> TYPE: DNA
<213> ORGANISM: artificial
<220> FEATURE:
<223> OTHER INFORMATION: PCR primer

<400> SEQUENCE: 8
aaggcatcca gttcatttcc taaat                                         25

<210> SEQ ID NO 9
<211> LENGTH: 29
<212> TYPE: DNA
<213> ORGANISM: artificial
<220> FEATURE:
<223> OTHER INFORMATION: PCR primer

<400> SEQUENCE: 9
cgtaggcaat acttacatca ctagacaaa                                     29

<210> SEQ ID NO 10
<211> LENGTH: 23
<212> TYPE: DNA
<213> ORGANISM: artificial
<220> FEATURE:
<223> OTHER INFORMATION: PCR primer

<400> SEQUENCE: 10
tgtctctccg acaaatgcaa ttt                                           23
```

```
<210> SEQ ID NO 11
<211> LENGTH: 21
<212> TYPE: DNA
<213> ORGANISM: artificial
<220> FEATURE:
<223> OTHER INFORMATION: PCR primer

<400> SEQUENCE: 11
tgttggctga agaagtgcaa g                                              21

<210> SEQ ID NO 12
<211> LENGTH: 20
<212> TYPE: DNA
<213> ORGANISM: artificial
<220> FEATURE:
<223> OTHER INFORMATION: PCR primer

<400> SEQUENCE: 12
ttcacccata agccaatgct                                                20

<210> SEQ ID NO 13
<211> LENGTH: 45
<212> TYPE: DNA
<213> ORGANISM: artificial
<220> FEATURE:
<223> OTHER INFORMATION: TEMPLATE

<400> SEQUENCE: 13
ggatcctaat acgactcact ataggagtgg caatcaccac caaat                    45

<210> SEQ ID NO 14
<211> LENGTH: 45
<212> TYPE: DNA
<213> ORGANISM: artificial
<220> FEATURE:
<223> OTHER INFORMATION: TEMPLATE

<400> SEQUENCE: 14
ggatcctaat acgactcact ataggagtgg caatcaccac caaat                    45

<210> SEQ ID NO 15
<211> LENGTH: 23
<212> TYPE: DNA
<213> ORGANISM: ARTIFICIAL
<220> FEATURE:
<223> OTHER INFORMATION: PRIMER

<400> SEQUENCE: 15
ggctcctttg ttaggttact gga                                            23

<210> SEQ ID NO 16
<211> LENGTH: 20
<212> TYPE: DNA
<213> ORGANISM: artificial
<220> FEATURE:
<223> OTHER INFORMATION: PRIMER

<400> SEQUENCE: 16
agtggcaatc accaccaaat                                                20
```